US008217073B2

(12) United States Patent
Weiner et al.

(10) Patent No.: US 8,217,073 B2
(45) Date of Patent: *Jul. 10, 2012

(54) PYRROLE DERIVATIVES AS THERAPEUTIC COMPOUNDS

(75) Inventors: Warren S. Weiner, Salt Lake City, UT (US); Rachel M. Slade, Salt Lake City, UT (US); Yevgeniya I. Klimova, Sandy, UT (US); Ruth J. Walton, Bountiful, UT (US); Mark B. Anderson, Oakland, CA (US)

(73) Assignee: Myrexis, Inc., Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/775,253

(22) Filed: May 6, 2010

(65) Prior Publication Data

US 2010/0216862 A1 Aug. 26, 2010

Related U.S. Application Data

(63) Continuation of application No. 12/057,140, filed on Mar. 27, 2008, now Pat. No. 7,714,022, which is a continuation-in-part of application No. PCT/US2006/037903, filed on Sep. 27, 2006.

(60) Provisional application No. 60/721,415, filed on Sep. 27, 2005, provisional application No. 60/786,556, filed on Mar. 27, 2006.

(51) Int. Cl.
*A61K 31/40* (2006.01)
*C07D 207/30* (2006.01)
(52) U.S. Cl. ........................................ 514/427; 548/563
(58) Field of Classification Search .................. 514/427; 548/563
See application file for complete search history.

(56) References Cited

U.S. PATENT DOCUMENTS

| 3,174,854 | A | | 3/1965 | Stumpf et al. |
| 5,077,142 | A | | 12/1991 | Sakon et al. |
| 5,124,482 | A | | 6/1992 | Butler et al. |
| 5,908,858 | A | * | 6/1999 | Kimura et al. ............... 514/427 |
| 5,935,990 | A | | 8/1999 | Khanna et al. |
| 6,953,855 | B2 | | 10/2005 | Mazurov et al. |
| 7,714,022 | B2 | | 5/2010 | Weiner et al. |
| 2003/0096813 | A1 | | 5/2003 | Cao et al. |
| 2003/0130165 | A1 | | 7/2003 | Reitz et al. |
| 2004/0180889 | A1 | | 9/2004 | Suto et al. |
| 2005/0182125 | A1 | | 8/2005 | Lockhart et al. |
| 2008/0249158 | A1 | | 10/2008 | Weiner et al. |
| 2009/0253768 | A1 | | 10/2009 | Klein et al. |
| 2010/0216862 | A1 | | 8/2010 | Weiner et al. |

FOREIGN PATENT DOCUMENTS

| AU | 2007294553 A1 | 3/2008 |
| EP | 0799823 A1 | 10/1997 |
| EP | 1389626 A1 | 2/2004 |
| EP | 1928827 A | 6/2008 |
| EP | 2059238 A2 | 5/2009 |
| GB | 1263940 A | 2/1972 |
| JP | 11180871 A | 7/1999 |
| WO | 97/16442 A1 | 5/1997 |
| WO | 00/19994 A1 | 4/2000 |
| WO | 02/085909 A1 | 10/2002 |
| WO | 02/089793 A1 | 11/2002 |
| WO | 03/073999 A2 | 9/2003 |
| WO | 2004/006836 A2 | 1/2004 |
| WO | 2004/058249 A1 | 7/2004 |
| WO | 2004/058269 A1 | 7/2004 |
| WO | 2004/110998 A1 | 12/2004 |
| WO | WO/2005/054191 | * 6/2005 ................ 548/415 |
| WO | 2005/080328 A1 | 9/2005 |
| WO | 2007/038684 A2 | 4/2007 |
| WO | 2007/038684 A3 | 9/2007 |

OTHER PUBLICATIONS

Aisen, Paul S., "Evaluation of Selective COX-2 Inhibitors for the Treatment of Alzheimer's Disease", Journal of Pain and Symptom Management, vol. 23, No. 4S, Apr. 2002, pp. 35-40.
Chong, Zhao Z., et al., "Oxidative Stress in the Brain: Novel Cellular Targets that Govern Survival During Neurodegenerative Disease", Progress in Neurobiology, vol. 75, 2005, pp. 207-246.
Katritzky, Alan R., et al., "Preparation of 1,2-Diaryl (heteroaryl) pyrroles and -3-methylpyrroles from N-Allylbenzotriazole, J. Org. Chem", vol. 65, 2000, pp. 8074-8076.
Bach, John Robert, "Amyotrophic Lateral Sclerosis : Prolongation of Life by Noninvasive Respiratory Aids", FCCP, American College of Chest Physicians, Jul. 2002, pp. 92-98.
Weisskopf et al., "Prospective Study of Occupation and Amyotrophic Lateral Sclerosis Mortality", American Journal of Epidemiology, vol. 162, No. 12, 2005, pp. 1146-1152.
Wang et al., "Vascular Endothelial Growth Factor Overexpression Delays Neurodegeneration and Prolongs Survival in Amyotrophic Lateral Sclerosis Mice", Journal of Neuroscience, vol. 27, No. 2, Jan. 10, 2007, pp. 304-307.
Braye et al., "New Unsaturated Heterocyclic Systems. I", European Research Associates, Journal of the American Chemical Society, vol. 83, Nov. 5, 1961, pp. 4406-4413.
Colotta et al., "Tricyclic heteroaromatic systems. [1]benzopyranopyrrol-4-ones and [1]benzopyrano-1,2,3-triazol-4-ones as benzodiazepine receptor ligands. Synthesis and structure-activity relationships", Journal of Medicinal Chemistry, American Chemical Society, vol. 33, No. 9, 1990, pp. 2646-2651.
Langridge et al. "Merostabilization vs. Linnett Stabilization in the Control of Regioselectivity of Pyrrole Formation by (4+2) cyclization", Journal of Organic Chemistry, American Chemical Society, vol. 50, No. 26, Dec. 1985, pp. 5503-5507.

(Continued)

*Primary Examiner* — Rebecca Anderson
*Assistant Examiner* — Samantha Shterengarts
(74) *Attorney, Agent, or Firm* — Kelly A. Echols; Herbert L. Ley, III

(57) ABSTRACT

Novel pyrrole derivatives are disclosed as $A\beta_{42}$-lowering agents for the treatment and prevention of neurodegenerative disorders characterized by the formation or accumulation of amyloid plaques comprising the $A\beta_{42}$ peptide.

10 Claims, No Drawings

OTHER PUBLICATIONS

Mattson et al., "Thiazolium-Catalyzed Additions of Acylsilanes: A General Strategy for Acyl Anion Addition Reactions", Journal of Organic Chemistry, vol. 71, No. 15 Jul. 21, 2006, pp. 5715-5724. —Abstract Only submitted.

McKinnon, D. M., "The Feist Synthesis of Pyrrole-3-Carboxyllc Esters", Canadian Journal of Chemistry, vol. 43, pp. 2628-2631.

Mortensen, Deborah S. et al., "Synthesis and Biological Evaluation of a Novel Series of Furans: Ligands Selective for Estrogen Receptor Alpha", Journal of Medicinal Chemistry, vol. 44, No. 23 Oct. 16, 2001, pp. 3838-3848.

Novikov et al., "1,3-Dipolar Cycloaddition of Azomethine Ylides Derived From Imines and Difluorocarbene to Alkynes: A New Active Pb-Mediated Approach to 2-Fluoropyrrole Derivatives", Journal of the Chemical Society, Perkin Transactions 1, Jan. 27, 2000, pp. 231-237.

Padwa et al., "A Convenient Synthesis of N-Substituted 2,4-Diaryl-Pyrroles", The Journal of Organic Chemistry, vol. 33, No. 1 Jan. 1968, pp. 454-455.

Praprotnik et al., "Filament Heterogeneity Within the Dystrophic Neurites of Senile Plaques Suggests Blockage of Fast Axonal Transport in Alzheimer's Disease", Acta Neuropathologica, Volume. 91, No. 3, 1996, pp. 226-235.

Wasserman et al., "Stereospecific Reactions of the Diphenacyl Halides", Journal of Organic Chemistry vol. 19, No. 4, Apr. 1954, pp. 515-521.

* cited by examiner

PYRROLE DERIVATIVES AS THERAPEUTIC COMPOUNDS

CROSS-REFERENCE TO RELATED APPLICATIONS

This application is a continuation of U.S. application Ser. No. 12/057,140, filed Mar. 27, 2008, now U.S. Pat. No. 7,714, 022 which is a continuation-in-part of International Application PCT/US06/37903, filed Sep. 27, 2006, which claims the benefit of U.S. Provisional Application No. 60/786,556, filed Mar. 27, 2006 and U.S. Provisional Application No. 60/721, 415, filed Sep. 27, 2005; all four of which are incorporated by reference herein in their entirety.

FIELD OF THE INVENTION

The invention relates to therapeutic compounds—their synthesis and use in treating diseases. In particular, the present invention is in the field of medicinal chemistry and relates to compounds that lower $A\beta_{42}$ peptide concentrations in vivo, by reducing the amount of $A\beta_{42}$ peptide produced or secreted by cells. Such compounds are potentially useful for the treatment and prevention of Alzheimer's and other neurodegenerative diseases in which excessive quantities of $A\beta_{42}$ peptide are secreted and accumulate in amyloid plaques in brain tissue.

BACKGROUND OF THE INVENTION

Dementia is a brain disorder that seriously affects a person's ability to carry out normal daily activities. Among older people, Alzheimer's disease (AD) is the most common form of dementia and involves parts of the brain that control thought, memory, and language. Despite intensive research throughout the world, the causes of AD are still unknown and there is no cure. AD most commonly begins after the age of 60 with the risk increasing with age. Younger people can also get AD, but it is much less common. It is estimated that 3 percent of men and women ages 65 to 74 have AD. Almost half of those ages 85 and older may have the disease. AD is not a normal part of aging. AD is a complex disease that can be caused by genetic and environmental factors.

In 1906, Dr. Alois Alzheimer, noticed changes in the brain tissue of a woman who had died of an unusual mental illness. In her brain tissue, he found abnormal clumps (now known as amyloid plaques) and tangled bundles of fibers (now known as neurofibrillary tangles) which, today, are considered the pathological hallmarks of AD. Other brain changes in people with AD have been discovered. For example, with AD, there is a loss of nerve cells in areas of the brain that are vital to memory and other mental abilities. Scientists have also found that there are lower levels of chemicals in the brain that carry complex messages back and forth between nerve cells. AD may disrupt normal thinking and memory by blocking these messages between nerve cells.

Plaques and tangles are found in the same brain regions that are affected by neuronal and synaptic loss. Neuronal and synaptic loss is universally recognized as the primary cause in decline of cognitive function. The number of tangles is more highly correlated with cognitive decline than amyloid load in patients with AD (Albert *PNAS* 93:13547-13551 (1996)). The cellular, biochemical, and molecular events responsible for neuronal and synaptic loss in AD are not known. A number of studies have demonstrated that amyloid can be directly toxic to neurons (Iversen et al. *Biochem. J.* 311:1-16 (1995); Weiss et al. *J. Neurochem.* 62:372-375 (1994); Lorenzo et al. *Ann NY Acad. Sci.* 777:89-95 (1996); Storey et al. *Neuropathol. Appl. Neurobiol.* 2:81-97 (1999)), resulting in behavioral impairment. The toxicity of amyloid or tangles is potentially aggravated by activation of the complement cascade (Rogers et al. *PNAS* 21:10016-10020 (1992); Rozemuller et al. *Res. Immunol.* 6:646-9 (1992); Rogers et al. *Res Immunol.* 6:624-30 (1992); Webster et al. *J. Neurochem.* 69(1):388-98 (1997)). This suggests involvement of inflammatory processes in AD and neuronal death seen in AD (Fagarasan et al. *Brain Res.* 723(1-2):231-4. (1996); Kalaria et al. *Neurodegeneration.* 5(4):497-503 (1996); Kalaria et al. *Neurobiol Aging.* 17(5):687-93 (1996); Farlow *Am J Health Syst Pharm.* 55 Suppl. 2:S5-10 (1998)).

Evidence that amyloid β protein (Aβ) deposition causes some forms of AD was provided by genetic and molecular studies of some familial forms of AD (FAD). (See, e.g., Ii *Drugs Aging* 7(2):97-109 (1995); Hardy *PNAS* 94(6):2095-7 (1997); Selkoe *J. Biol. Chem.* 271(31):18295-8 (1996)). The amyloid plaque buildup in AD patients suggests that abnormal processing of Aβ may be a cause of AD. Aβ is a peptide of 39 to 42 amino acids and forms the core of senile plaques observed in all Alzheimer cases. If abnormal processing is the primary cause of AD, then familial Alzheimer's disease (FAD) mutations that are linked (genetically) to FAD may induce changes that, in one way or another, foster Aβ deposition. There are 3 FAD genes known so far (Hardy et al. *Science* 282:1075-9 (1998); Ray et al. (1998)). Mutations in these FAD genes can result in increased Aβ deposition.

The first of the 3 FAD genes codes for the Aβ precursor, amyloid precursor protein (APP) (Selkoe *J. Biol. Chem.* 271 (31):18295-8 (1996)). Mutations in the APP gene are very rare, but all of them cause AD with 100% penetrance and result in elevated production of either total Aβ or $A\beta_{42}$, both in model transfected cells and transgenic animals. The other two FAD genes code for presenilin 1 and 2 (PS1, PS2) (Hardy *PNAS* 94(6):2095-7 (1997)). The presenilins contain 8 transmembrane domains and several lines of evidence suggest that they are involved in intracellular protein trafficking. Other studies suggest that the presenilins function as proteases. Mutations in the presenilin genes are more common than in the APP genes, and all of them also cause FAD with 100% penetrance. Similar to APP mutants, studies have demonstrated that PS1 and PS2 mutations shift APP metabolism, resulting in elevated $A\beta_{42}$ production (in vitro and in vivo).

Aβ formation is another target for affecting AD progression since Aβ amyloid plaques are a central pathological hallmark of the disease. Recently, it was suggested that certain NSAIDs are capable of lowering the level of $A\beta_{42}$. United States Patent Application 2002/0128319 to Koo et al. discloses the use of an $A\beta_{42}$ lowering amount of NSAID for treating AD. R-Flurbiprofen, which negligibly inhibits COX activity, was shown in Koo et al. to lower $A\beta_{42}$ in a transgenic mouse model and CHO cells. The hope is that by lowering the level of $A\beta_{42}$, the formation of the amyloid plaques central to the disease would be retarded.

A clinical trial using a therapy designed to eliminate Aβ plaques from disease patients failed despite strong evidence of efficacy in animal models (Pieffer et al. *Science* 298:1379 (2002)). The Aβ-lowering therapy that worked in animal models caused serious problems in humans. In view of the clinical studies, Atwood et al. (*Science* 299:1014 (2003)) noted that "Mounting evidence indicates that this deposition of amyloid-β may be a neuroprotective response to injury" and "These results demonstrate yet again the futility of removing a protein, amyloid-β, which has ubiquitous tissue expression, without first understanding its function(s)." Additionally, secretase inhibitors, which were designed to alter processing of APP, have turned out to be toxic compounds not likely to be suitable for chronic human use. Thus, it is not clear if reducing Aβ or Aβ$_{42}$ is a realistic treatment/prevention option. Indeed, as noted recently, mutations in PS-1 associated with AD may cause the disease not through altering Aβ processing but rather by affecting calcium homeostasis (Mattson, *Nature* 442:385-386 (2003)).

Several epidemiological studies have reported an association between long-term use of NSAIDs, such as ibuprofen and aspirin, with reduced risk for certain malignancies and neurodegenerative processes characterized by dementia of the Alzheimer's type. A variety of explanations have been given for the reduced cancer and AD risk associated with long-term NSAID use. The primary action of NSAIDs appears to be inhibition of cyclooxygenase (COX) activity. Thus, a leading hypothesis is that NSAIDs reduce risk for certain cancers and AD by affecting the COX enzymes. Other explanations include mediation of apoptosis, modulation of growth factors, and modulation of the nuclear factor kappa B pathway (NF-κB).

U.S. Pat. No. 5,192,753 to Rogers et al. discloses the use of NSAIDs to treat AD through the inhibition of cyclooxygenase and therefore inhibition of prostaglandin synthesis. U.S. Pat. No. 5,643,960 to Brietner et al. discloses the use of COX inhibiting NSAIDs to delay the onset of AD symptoms. U.S. Pat. No. 6,025,395 to Brietner et al. relates to the use of COX inhibiting NSAIDs.

Statins have also been implicated as potential AD therapeutics by retrospective epidemiological studies. See Petanceska et al., *J. Mol. Neurosci.*, 19:155-61 (2002). These retrospective studies indicate that statin users have a lower prevalence of developing AD. Since many possible explanations can account for the lower prevalence of AD in statin users aside from the use of statin, and combined with the fact that no statins have been approved for an AD indication, it is not certain if (and how/when) they can be used to treat AD.

In the United States alone, four million adults suffer from AD. Not only is AD significantly impacting the lives of countless families today, it is threatening to become even more of a problem as the baby boom generation matures. The economic burden of AD is estimated to cost over $100 billion a year and the average lifetime cost per patient is estimated to be $174,000. Unfortunately, there is no cure available for AD. Of the five drugs currently being used in the US for the treatment of AD, four of them—tacrine (Cognex®), donepezil (Aricept®), rivastigmine (Exelon®), and galantamine (Reminyl®)—are inhibitors of acetylcholinesterase. Another drug, memantine, was recently approved for treating moderate-to-severe AD. More recently it was reported that memantine showed efficacy in treating mild-to-moderate AD. Memantine is a NMDA receptor antagonist.

The drugs currently used for treating AD, including memantine and the acetylcholine esterase inhibitors, are marginally efficacious and have undesirable side-effects. Thus, there is a large unmet need for better and safer drugs for the treatment or prevention, or for the delay of onset, or reversal, of symptoms of AD and other neurodegenerative diseases characterized by the deposition of amyloid plaques comprising the Aβ$_{42}$ peptide.

Cerebral amyloid angiopathy (CAA)—also known as cerebrovascular amyloidosis, congophilic angiopathy, and dysphoric angiopathy—is characterized by the deposition of β-amyloid in the media and adventitia of small- and medium-sized arteries (and less frequently, veins) of the cerebral cortex and leptomeninges. Widely recognized as a component of other disorders in which β-amyloid is deposited in the brain, such as AD and Down Syndrome, CAA is not associated with systemic amyloidosis, which is caused by the aggregation of proteins other than β-amyloid. Although CAA is recognized as one of the morphologic hallmarks of AD, it is often found in the brains of elderly patients who are otherwise neurologically healthy, and show no signs of dementia. However, while often asymptomatic, CAA can result in, and present as, intracranial hemorrhage (ICH), dementia, or transient neurologic events, with ICH being the most commonly observed effect of CAA. While the vast majority of CAA cases are sporadic, at least two familiar forms are known (i.e., hereditary cerebral hemorrhage with amyloidosis [HCHWA]-Dutch type and HCHWA-Icelandic type).

CAA is recognized by its characteristic pathophysiology. Specifically, the deposition of β-amyloid damages the media and adventitia of cortical and leptomeningeal vessels, leading to thickening of the basal membrane, stenosis of the vessel lumen, and fragmentation of the internal elastic lamina. This can result in fibrinoid necrosis and micro-aneurysm formation, predisposing a patient to ICH. Impaired elimination and accumulation of soluble and insoluble β-amyloid peptide likely underlies the pathogenesis and explains the link between CAA and AD.

At present, CAA can only be accurately diagnosed postmortem, hence its true incidence and prevalence is hard to quantify. However, estimates can be made based on autopsies and the incidence of ICH events. For example, a series of 400 autopsies found evidence of CAA in the brains of 18.3% of men and 28% of women aged 40-90 years. In a series of 117 autopsies of brains of patients with confirmed AD, 83% had evidence of CAA. The prevalence of CAA increases with advancing age; in some autopsy series it has been found in 5% of the brains of individuals in the seventh decade (aged 60-69), but in 50% of the brains of individuals older than 90 years.

CAA is estimated to account for up to 15% of all ICH in patients older than 60 years of age, and up to 50% of nontraumatic lobar ICH in patients older than 70 years, which, in turn, accounts for approximately 15-20 cases per 100,000 people per year. CAA and CAA-related hemorrhage are particularly common in elderly individuals with AD and middle-aged patients with Down syndrome.

The growing appreciation of the incidence of CAA in elderly individuals, both with and without AD, and in middle-aged Down syndrome patients indicates that there is a large unmet need for safe and effective drugs for the treatment, prevention, delay of onset, or reversal, of symptoms of CAA in such patients. Drugs that effectively lower Aβ$_{42}$ peptide concentrations in the brains of such patients, thereby slowing or stopping the deposition of β-amyloid in the media and adventitia of small- and medium-sized arteries (and less frequently, veins) of the cerebral cortex and leptomeninges, should meet this need in these patients.

Individuals with trisomy 21, or Down syndrome (DS), develop a clinical syndrome of dementia that has the same neuropathological characteristics as described in AD patients without DS. The principle difference in AD neuropathology between individuals with DS and those without DS, is the age of onset. It is estimated that 10-25% of patients with DS develop AD-like dementia at age 40-49, 20-50% develop AD-like dementia at age 50-59, and 60-75% develop AD-like dementia when older than 60 years. AD-like dementia decreases survival in people with DS who are older than 45 years, but not ever person with DS will develop symptoms of AD-like dementia, even if, upon autopsy, their brain reveals the neuropathologic changes commonly associated with AD.

The first evidence for a link between DS and AD came when Blenner and Wong reported the isolation and identification of the same β-amyloid peptide in the meningeal vessels of individuals with either DS or AD. Glenner & Wong *Biochem. Biophys. Res. Commun.* 122:1131-1135 (1984). Subsequent mapping of the gene encoding the amyloid β precursor protein (APP) to chromosome 21 suggested that the extra copy of the APP gene possessed by trisomy-21 (DS) patients resulted in elevated expression of APP, which, in turn, resulted in increased levels of β-amyloid peptide and accelerated accumulation of β-amyloid plaques. Recently, the link between APP over-expression, and Aβ amyloidosis, in both DS and AD patients, has been further strengthened by the discovery of several independent duplications of the APP locus on chromosome 21 in French families with a variable, autosomal dominant phenotype between the pure AD phenotype seen in most families with APP mutations, and the cerebral hemorrhage phenotype of Dutch angiopathy associated with the APP E693Q (Dutch) mutation. These findings highlight the importance of APP gene dosage and provide strong support for the amyloid hypothesis, which postulates that accumulation of β-amyloid in the brain drives the neuropathogenesis seen in both AD and DS patients. Rovelet-Lecrux, et al. *Nat. Genet.* 38:24-26 (2006).

As improved health care leads to more and more DS patients surviving into middle age and beyond, there is a increasing need for safe, effective drugs to treat, slow or prevent the onset of dementia that almost inevitably occurs in aging DS patients. Drugs that effectively lower $A\beta_{42}$ peptide concentrations in the brains of such patients, and thereby slow or stop the aggregation of β-amyloid plaques in these patients' brains, should meet this need, and should reduce the incidence of dementia in aging DS patients.

BRIEF SUMMARY OF THE INVENTION

The present invention is in the field of medicinal chemistry and relates to novel compounds that decrease the secretion of the amyloid plaque forming peptide, $A\beta_{42}$, by mammalian cells, especially neurons. The compounds are useful for the treatment or prevention, or for the delay of onset or reversal, of symptoms of mild cognitive impairment (MCI), AD and other neurodegenerative diseases characterized by the formation or accumulation of amyloid plaques comprising the $A\beta_{42}$ peptide. The compounds are also useful for the treatment of CAA.

In particular, compounds are disclosed as potential $A\beta_{42}$-lowering agents for the treatment and prevention of neurodegenerative disorders and include compounds of Formula I:

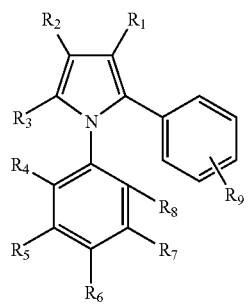

(I)

and pharmaceutically acceptable salts, esters, hydrates or solvates thereof, wherein:

$R_1$ is a hydrogen atom, halogen (Cl, F, Br, I), hydroxy, alkyl, substituted alkyl, alkoxy, substituted alkoxy, or —$CO_2R_{10}$, and $R_{10}$ is a hydrogen atom, alkyl or substituted alkyl;

$R_2$ is a hydrogen atom, halogen (Cl, F, Br, I), hydroxy, alkyl, substituted alkyl, alkoxy, substituted alkoxy, or phenyl, optionally substituted with 0-5 phenyl substituents;

$R_3$ is a hydrogen atom, halogen (Cl, F, Br, I), hydroxy, alkyl, substituted alkyl, alkoxy, or substituted alkoxy when $R_2$ is phenyl, substituted or not, or, when $R_2$ is not phenyl $R_3$ is —$CH_2CH_2$-phenyl optionally substituted with 0-5 phenyl substituents;

$R_4$ is a hydrogen atom, halogen (Cl, F, Br, I), hydroxy, alkyl, substituted alkyl, alkoxy, or substituted alkoxy;

$R_5$ is a hydrogen atom, halogen (Cl, F, Br, I), hydroxy, alkyl, substituted alkyl, alkoxy, or substituted alkoxy;

one of $R_6$ and $R_7$ is —$(CH_2)_nCO_2H$ or —$O(CH_2)$—$CO_2H$, wherein n is an integer from 0 to 4, or —$(CH_2)_m$O$(CH_2)_pCO_2H$, wherein m is an integer from 1 to 2 and p is an integer from 1 to 2, while the other of $R_6$ and $R_7$ is a hydrogen atom, halogen (Cl, F, Br, I), hydroxy, alkyl, substituted alkyl, alkoxy, or substituted alkoxy;

$R_8$ is a hydrogen atom, halogen (Cl, F, Br, I), hydroxy, alkyl, substituted alkyl, alkoxy, or substituted alkoxy;

$R_9$ is 0-5 phenyl substituents, such as halogen (i.e., F, Cl, Br and I), hydroxy, or haloalkyl (such as trifluoromethyl).

The present invention also encompasses the use of the compounds of the invention for therapy, and specifically for the preparation of pharmaceutical compositions that can be used for the treatment, prevention, or delay of onset or reversal of symptoms of AD and other neurodegenerative diseases and disorders, such as MCI and CAA, that respond favorably to reductions in $A\beta_{42}$ levels, in patients in need of such treatment. In particular, the compositions and methods of the present invention can be used to treat, prevent, or delay the onset of or reverse the symptoms of such diseases and disorders as AD, MCI, dementia associated with DS, and CAA, which are characterized by the formation or accumulation of amyloid plaques or deposits, comprising the $A\beta_{42}$ peptide, in the brains of patients in need of such treatment.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION OF THE INVENTION

The present invention provides novel compounds that, when contacted with mammalian cells, especially neurons, decrease the secretion of the amyloid plaque forming peptide, $A\beta_{42}$. These compounds have utility as therapeutics for use in the treatment, prevention, or delay of onset or reversal of symptoms of AD, MCI and DS-associated dementia, and other neurodegenerative diseases and disorders, such as CAA, that respond favorably to reductions in $A\beta_{42}$ levels, in patients in need of such treatment. In particular, the compounds of the present invention can be used to treat, prevent, or delay the onset of or reverse the symptoms of such diseases and disorders as AD, MCI, CAA, and dementia in DS patients, which are characterized by the formation or accumulation of amyloid plaques, comprising the $A\beta_{42}$ peptide, in the brains of patients in need of such treatment.

The present invention also provides pharmaceutical compositions or medicaments comprising one or more therapeutic compounds of the present invention and a pharmaceutically acceptable excipient or carrier. Such pharmaceutical compositions are formulated in order to deliver a therapeutically effective, or prophylactically effective, amount of the compound to a patient in need of such treatment.

The present invention also provides therapeutic methods that make use of the therapeutic compounds and compositions of the present invention for the treatment, prevention, or delay of onset or reversal of symptoms of AD, MCI and DS-associated dementia, and other neurodegenerative diseases and disorders, such as CAA, that respond favorably to reductions in $A\beta_{42}$ levels. In particular, the therapeutic methods of the present application can be used to treat, prevent, or delay the onset of or reverse the symptoms of such diseases and disorders as AD, MCI, CAA, and DS-associated dementia, which are characterized by the formation or accumulation of amyloid plaques, comprising the $A\beta_{42}$ peptide, in the brains of patients in need of such treatment.

The present invention and various embodiments thereof are described in more detail following these definitions.

Definitions

As used herein, the terms pertaining to the compounds of the invention have the meanings set forth below.

"Alkyl" is a straight chain or branched, cyclic or noncyclic, saturated or unsaturated alkyl containing from 1 to 12 carbon atoms (also referred to herein as "$C_{1-12}$ alkyl"). Similarly, a "lower alkyl" is as defined above, but contains from 1 to 6 carbon atoms (also referred to herein as a "$C_{1-6}$ alkyl"). Representative saturated straight chain alkyls include methyl, ethyl, n-propyl, n-butyl, n-pentyl, n-hexyl, and the like; while saturated branched alkyls include isopropyl, sec-butyl, isobutyl, tent-butyl, isopentyl, and the like. Representative saturated cyclic alkyls include cyclopropyl, cyclobutyl, cyclopentyl, cyclohexyl, and the like. Unsaturated alkyls contain at least one double or triple bond between adjacent carbon atoms (referred to as an "alkenyl" or "alkynyl," respectively). Representative straight chain and branched alkenyls include ethylenyl, propylenyl, 1-butenyl, 2-butenyl, isobutenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1 butynyl, and the like. Representative unsaturated cyclic alkyls include cyclopentenyl and cyclohexenyl, and the like.

"Alkoxy" is an alkyl having at least one alkyl hydrogen atom replaced with an oxygen atom, such as methoxy, ethoxy, n-propoxy, n-butoxy, n-pentoxy, isopropoxy, sec-butoxy and the like. "Lower alkoxy" has same meaning, but utilizing lower alkyl in place of alkyl.

"Aminoalkyl" is a straight chain or branched, cyclic or noncyclic, saturated or unsaturated alkyl containing from 1 to 12 carbon atoms with at least one alkyl hydrogen atom or carbon atom replaced with —NH$_2$ or —NH—, respectively (also referred to herein as "$C_{1-12}$ aminoalkyl").

"Aryl" is an aromatic carbocyclic moiety contain from 6 to 12 carbon atoms (also referred to herein as a "$C_{6-12}$ aryl"), such as phenyl and naphthyl.

"Aryloxy" is an aryl having at least one aryl hydrogen atom replaced with an oxygen atom, such as phenoxy and the like.

"Arylalkyl" is an alkyl having at least one alkyl hydrogen atom replaced with an aryl moiety, such as benzyl, —(CH$_2$)$_2$phenyl, —(CH$_2$)$_3$phenyl, —CH(phenyl)$_2$, and the like.

"Arylalkoxy" is an arylalkyl having at least one alkyl hydrogen replaced with an oxygen atom, such as benzoxy and the like. "Alkylaryloxy" is an arylalkyl having at least one aryl hydrogen replaced with an oxygen atom, such as hydroxy benzyl and the like.

"Heterocycle" means a 5- to 7-membered monocyclic, or 7- to 10-membered bicyclic, heterocyclic ring which is either saturated, unsaturated, or aromatic, and which contains from 1 to 4 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring. The heterocycle may be attached via any heteroatom or carbon atom. Heterocycles include heteroaryls as defined below. Thus, in addition to the heteroaryls listed below, heterocycles also include morpholinyl, pyrrolidinonyl, pyrrolidinyl, piperidinyl, hydantoinyl, valerolactamyl, oxiranyl, oxetanyl, aziridinyl, azetidinyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl and the like.

"Heterocyclealkyl" means an alkyl having at least one alkyl hydrogen atom replaced with a heterocycle moiety, such as —CH$_2$(heterocycle), —(CH$_2$)$_2$(heterocycle) and the like.

"Heteroaryl" means an aromatic heterocycle ring of 5- to 10 members and having at least one heteroatom selected from nitrogen, oxygen and sulfur, and containing at least 1 carbon atom, including both mono- and bicyclic ring systems. Representative heteroaryls are pyridyl, furyl, benzofuranyl, thiophenyl, benzothiophenyl, quinolinyl, pyrrolyl, indolyl, oxazolyl, benzoxazolyl, imidazolyl, benzimidazolyl, thiazolyl, benzothiazolyl, isoxazolyl, pyrazolyl, isothiazolyl, pyridazinyl, pyrimidinyl, pyrazinyl, triazinyl, cinnolinyl, phthalazinyl, quinazolinyl and the like.

"Heteroarylalkyl" means an alkyl having at least one alkyl hydrogen atom replaced with a heteroaryl moiety, such as —CH$_2$pyridinyl, —CH$_2$pyrimidinyl, and the like.

The term "substituted" as used herein means any of the above groups—that is, alkyl, aryl, arylalkyl, heterocycle, heterocyclealkyl, heteroaryl or heteroarylalkyl—wherein at least one hydrogen atom is replaced with a substituent. In the case of an oxo substituent (=O), two hydrogen atoms are replaced. A "substituent" in this regard is halogen (such as F, Cl, Br and I), oxo, hydroxy, haloalkyl (such as trifluoromethyl), alkyl, aryl, heteroaryl, heterocycle, —OR, —C(=O)R, —C(=O)OR, —C(=O)NRR, —NRR, —NRC(=O)R, —NRC(=O)OR, —NRC(=O)NRR, —OC(=O)R, —OC(=O)OR, —OC(=O)NRR, —SH, —SR, —SOR, —SO$_2$R, —SO$_2$NR$_2$, —NRSO$_2$R, —NR$_2$SO$_2$R, —Si(R)$_3$, or —OP(OR)$_3$, wherein each occurrence of R is the same or different and independently a hydrogen atom, alkyl, substituted alkyl, aryl, substituted aryl, arylalkyl, substituted arylalkyl, heterocycle, substituted heterocycle, heterocyclealkyl or substituted heterocyclealkyl, or wherein any two R groups attached to the same nitrogen atom, taken together with the nitrogen atom to which they are attached, form a heterocyclic ring or a substituted heterocyclic ring.

The term "phenyl substituent" has the same meaning as defined above for "substituent," except that it does not include an oxo substituent.

As used herein, the term "preventing," when used in the context of "preventing a disease or disorder," refers to both not allowing a symptom to increase or worsen, as well as reducing or slowing the rate of increase or worsening of the symptoms of the disease or disorder. For example, a symptom can be measured as the amount of particular disease marker, i.e., $A\beta_{42}$ peptide present in a patient tissue sample, or the density or number of amyloid plaques comprising the $A\beta_{42}$ peptide, in a patient's brain. In another example, the symptom can be cognitive or behavioral decline in a patient. Preventing an increase, according to the definition provided herein, means that the amount of symptom (e.g., $A\beta_{42}$ peptide, amyloid plaques, or cognitive or behavioral decline) does not increase or worsen, or that the rate at which it increases or worsens is reduced.

As used herein, the terms "treating a neurodegenerative disease," "treating Alzheimer's disease," "treating AD," "treating cerebral amyloid angiopathy," "treating CAA," "treating mild cognitive impairment," "treating MCI," or, "treading DS-associated dementia," refer to a slowing of the progression of the disease or disorder, or its symptoms, or a reversal of the disease or disorder, or its symptoms. For example, "treating AD" includes not only treating a disease, but reducing or reversing a symptom or symptoms of that disease.

As used herein, the terms "preventing a neurodegenerative disease," "preventing Alzheimer's disease," "preventing cerebral amyloid angiopathy," or "preventing DS-associated dementia," refer to a slowing of the onset of the disease or the symptoms thereof. The phrases "preventing Alzheimer's disease," "preventing cerebral amyloid angiopathy," or "preventing DS-associated dementia," can include stopping the onset of the disease or the symptoms thereof, or reversing the symptoms of the disease once they are manifest.

As used herein, the term "$A\beta_{42}$-lowering" refers the capability of a compound or composition to reduce the amount of $A\beta_{42}$ peptide present and/or being produced or secreted by cells, either in vitro, or in a patient. Levels of $A\beta_{42}$ peptide, and levels of amyloid plaques containing the $A\beta_{42}$ peptide, can be determined by a variety of assays known in the art, and can be determined in patient tissue samples in vitro, in cell culture media, or within living patients. Specific methods of determining $A\beta_{42}$ levels are described in the examples below, and in the references cited herein.

In certain embodiments of the present invention, the "$A\beta_{42}$-lowering" activity of the compound or composition is determined or monitored in tissue samples taken from patients. These tissue samples may include, but are not limited to, serum, plasma, CSF, and brain tissue from biopsies. In other embodiments, the "$A\beta_{42}$-lowering" activity of the compound or composition is determined or monitored by assaying for amyloid plaques containing the $A\beta_{42}$ peptide within the bodies of living patients using non-invasive imaging techniques, including, but not limited to, positron emission tomography (PET) combined with radioligand tracers that specifically bind amyloid plaques. Such techniques were the subject of a review by Mathis et al. (See Mathis et al., *Curr Pharm Des.* 10:1469-92 (2004)). Advances in such techniques, as well as specific methods used, have been described more recently in Klunk et al., *Ann. Neurol.* 55:306-319 (2004); Price et al., *J. Cereb. Blood Flow Metab.* 25:1528-1547 (2005); Lopresti et al., *J. Nucl. Med.* 46:1959-1972 (2005); and Fagan et al., *Ann. Neurol.* 59:512-519 (2006); which are all incorporated by reference herein in their entirety.

As used herein, the terms "Alzheimer's Disease" or "AD," have specific meaning, in accordance with standard medical practice. Further, the terms "Mild Cognitive Impairment," and "MCI," have specific meaning, in accordance with standard medical practice, as does the term "dementia associated with Down Syndrome," or "DS-associated dementia." Nevertheless, the diagnosis of AD, MCI, or DS-associated dementia, or even cognitive decline in general, can be made using any known method in the art. Typically, AD is diagnosed using a combination of clinical and pathological assessments. For example, progression or severity of AD can be determined using: Mini Mental State Examination (MMSE) as described by Mohs et al. *Int Psychogeriatr* 8:195-203 (1996); Alzheimer's Disease Assessment Scale-cognitive component (ADAS-cog) as described by Galasko et al. *Alzheimer Dis Assoc Disord,* 11 suppl 2:S33-9 (1997); the Alzheimer's Disease Cooperative Study Activities of Daily Living scale (ADCS-ADL) as described by McKhann et al. *Neurology* 34:939-944 (1984); and the NINCDS-ADRDA criteria as described by Folstein et al. *J. Psychiatr. Res.* 12:189-198 (1975). In addition, methods that allow for evaluating different regions of the brain and estimating amyloid plaque and neurofibrillary tangle abundance can be used. These methods are described by Braak et al. *Acta Neuropathol* 82:239-259 (1991); Khachaturian *Arch. Neuro.* 42:1097-1105 (1985); Mirra et al. (1991) *Neurology* 41:479-486; and Mirra et al. *Arch Pathol Lab Med* 117:132-144 (1993); and, as mentioned above, non-invasive methods utilizing PET scanning have been reviewed in Mathis et al., *Curr Pharm Des.* 10:1469-92 (2004).

As used herein, the terms "cerebral amyloid angiopathy" or "CAA" refer to the pathological deposition of β-amyloid in the media and adventitia of small- and medium-sized arteries (and less frequently, veins) of the cerebral cortex and leptomeninges, which, as noted previously, is often associated with ICH. Further, the term "cerebral amyloid angiopathy" or "CAA" have specific meaning, in accordance with standard medical practice, and are diagnosed by methods established in the art.

As noted above, the present invention provides methods for treating, or preventing, or delaying the onset of, or reversing the symptoms of neurodegenerative diseases and disorders characterized by the deposition or accumulation of amyloid plaques or deposits comprising the $A\beta_{42}$ peptide. These methods can be applied in any such neurodegenerative disease or disorder, but have clear application in AD, at all stages of its progression, can also potentially be applied in MCI and DS-associated dementia. These methods also have clear application in CAA, where the deposition or accumulation of amyloid plaques or deposits comprising the $A\beta_{42}$ peptide is also observed.

All such methods have in common the lowering of $A\beta_{42}$ levels in patients in need of such treatment through the reduction in cellular secretion of the $A\beta_{42}$ peptide. While not wishing to be bound by theory, it is believed that by lowering the cellular secretion of the $A\beta_{42}$ peptide in an individual by administering an effective amount of a composition described herein, neurodegenerative diseases such as AD, MCI, CAA, and DS-associated dementia can be treated or prevented, or the symptoms of such diseases can be delayed, alleviated or even eliminated.

Generally, the invention relates to the concept that compounds of Formulae I-VI can be used to lower the cellular secretion of the $A\beta_{42}$ peptide. Thus, diseases characterized by increased levels of $A\beta_{42}$, or by the accumulation or deposition of amyloid plaques or deposits comprising the $A\beta_{42}$ peptide, can be treated or prevented with the methods of the invention, which are specifically designed to lower the cellular secretion of the $A\beta_{42}$ peptide, prevent an increase in the cellular secretion of the $A\beta_{42}$ peptide, or prevent an increase in the deposition or formation of $A\beta_{42}$ peptide-containing amyloid plaques, and/or reduce the rate of deposition of such plaques, in a patient.

Importantly, however, the methods in the present invention may also be used prophylactically in patients at risk of developing neurodegenerative diseases and disorders characterized by the deposition or accumulation of amyloid plaques or deposits comprising the $A\beta_{42}$ peptide. Such patients may be identified by any acceptable method in the art, such as through genotyping by any suitable method, or by analysis of their family's history of disease, or through pedigree analysis. Methods of determining the genotype of an individual include nucleic acid sequencing, selective hybridization, allele-specific amplification, and the like. For patients found to be at risk by such methods, the methods of the present invention may be used to prevent or delay the onset of symptoms of neurodegenerative diseases and disorders characterized by the deposition or accumulation of amyloid plaques or deposits comprising the $A\beta_{42}$ peptide.

Further, while $A\beta_{42}$ appears to be central to Alzheimer's disease pathogenesis, and $A\beta_{42}$ is a major component of the amyloid plaques that are a hallmark of AD, it has been observed that $A\beta_{42}$ levels in cerebrospinal fluid (CSF), are actually decreased in patients with AD. This decrease has been hypothesized to reflect an ability of established amyloid plaques to act as a "sink" for $A\beta_{42}$, thereby hindering the transport of $A\beta_{42}$ from the extracellular matrix where the polypeptide is normally secreted into the CSF (Fagan et al., *Ann. Neurol.* 59:512-519 (2006)). Recent experiments in which in vivo amyloid plaque load has been quantified in the brains of living patients using positron emission tomography imaging in combination with the amyloid-binding agent Pittsburgh Compound-B has confirmed an inverse correlation between amyloid deposition into plaques and CSF $A\beta_{42}$ levels (Fagan et al., *Ann. Neurol.* 59:512-519 (2006) and Fagan et al. *Arch. Neurol.* 64:343-349 (2007)). Furthermore, these studies have revealed that even the very mildest symptomatic stage of AD (i.e., MCI) exhibits the same inverse correlation between amyloid plaque load and CSF $A\beta_{42}$ levels as more advanced AD, and the same inverse correlation exists regardless of the presence of dementia (Fagan et al. *Arch. Neurol.* 64:343-349 (2007)).

Consequently, it has been suggested that brain amyloid imaging and CSF $A\beta_{42}$ levels may potentially serve as antecedent biomarkers of (preclinical) AD (Fagan et al., *Ann. Neurol.* 59:512-519 (2006)). As the skilled artisan would readily appreciate, such antecedent biomarkers can be used to identify patients in need of prophylactic treatment with the compounds of the present invention.

Therapeutic Compounds

The present invention includes compounds of Formula I:

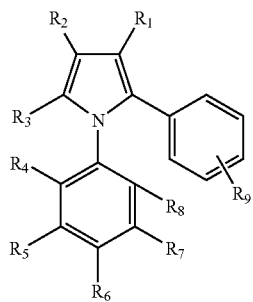

(I)

or pharmaceutically acceptable salts, esters, hydrates or solvates thereof:

$R_1$ is a hydrogen atom, halogen (Cl, F, Br, I), hydroxy, alkyl, substituted alkyl, alkoxy, substituted alkoxy, or —(CH$_2$)$_q$CO$_2$R$_{10}$, wherein q is an interger from 0 to 4 and $R_{10}$ is a hydrogen atom, alkyl or substituted alkyl;

$R_2$ is a hydrogen atom, halogen (Cl, F, Br, I), hydroxy, alkyl, substituted alkyl, alkoxy, substituted alkoxy, or phenyl, optionally substituted with 0-5 phenyl substituents;

$R_3$ is a hydrogen atom, halogen (Cl, F, Br, I), hydroxy, alkyl, substituted alkyl, alkoxy, or substituted alkoxy when $R_2$ is phenyl, or, when $R_2$ is not phenyl $R_3$ is —CH$_2$CH$_2$-phenyl optionally substituted with 0-5 phenyl substituents;

$R_4$ is a hydrogen atom, halogen (Cl, F, Br, I), hydroxy, alkyl, substituted alkyl, alkoxy, or substituted alkoxy;

$R_5$ is a hydrogen atom, halogen (Cl, F, Br, I), hydroxy, alkyl, substituted alkyl, alkoxy, or substituted alkoxy;

one of $R_6$ and $R_7$ is —(CH$_2$)$_n$CO$_2$R$_{11}$ or —O(CH$_2$)$_n$CO$_2$R$_{11}$, wherein n is an integer from 0 to 6, preferably 0 to 4 (e.g., 0, 1, 2, 3, or 4), and $R_{11}$ is a hydrogen atom, alkyl or substituted alkyl; or is —(CH$_2$)$_m$O(CH$_2$)$_p$CO$_2$R$_{11}$, wherein m is an integer from 0 to 4 (e.g., 0, 1, 2, 3, or 4), and p is an integer from 1 to 6, preferably 1 to 4 (e.g., 1, 2, 3, or 4), and $R_{11}$ is a hydrogen atom, alkyl or substituted alkyl; while the other of $R_6$ and $R_7$ is a hydrogen atom, halogen (Cl, F, Br, I), hydroxy, alkyl, substituted alkyl, alkoxy, or substituted alkoxy;

$R_8$ is a hydrogen atom, halogen (Cl, F, Br, I), hydroxy, alkyl, substituted alkyl, alkoxy, or substituted alkoxy; and $R_9$ is 0-5 independent phenyl substituents, such as halogen (e.g., F, Cl, Br or I), hydroxy, or haloalkyl (e.g., trifluoromethyl).

In some embodiments of the present invention, $R_1$ is a hydrogen atom; halogen (e.g., Cl, F, Br, I), hydroxyl, $C_{1-6}$ alkyl (e.g., methyl, ethyl, propyl, isopropyl or butyl or isobutyl) optionally substituted with 1 to 3 halogen (e.g., Cl, F, Br, I) or hydroxyl; $C_{1-6}$ alkoxy; or —(CH)$_q$CO$_2$R$_{10}$, wherein $R_{10}$ is a hydrogen atom or $C_{1-6}$ alkyl, and q is an integer of 0 to 4 (e.g., 0, 1, 2, 3 or 4).

In some other embodiments, $R_1$ is a hydrogen atom; or —(CH)$_q$CO$_2$R$_{10}$, wherein $R_{10}$ is $C_{1-6}$ alkyl, and q is an integer of 0 to 4 (0, 1, 2, 3 or 4).

In still other embodiments, $R_1$ is a hydrogen atom; or —CO$_2$R$_{10}$, wherein $R_{10}$ is methyl or ethyl.

In some embodiments of the present invention, $R_2$ is a hydrogen atom, halogen (e.g., Cl, F, Br, I), hydroxyl, $C_{1-6}$ alkyl (e.g., methyl, ethyl, propyl, isopropyl or butyl or isobutyl) optionally substituted with 1 to 3 halogen (e.g., Cl, F, Br, I) or hydroxyl; $C_{1-6}$ alkoxy optionally substituted with 1 to 3 halogens (e.g., Cl, F, Br, I) or hydroxyls or amino groups; or phenyl, optionally substituted with 1-5 same or different substituents chosen from halogen (e.g., Cl, F, Br, I), $C_{1-6}$ alkyl optionally substituted with 1 to 3 halogens (e.g., Cl, F, Br, I) or hydroxyl, hydroxy, or —(CH)$_q$CO$_2$R$_{10}$ wherein $R_{10}$ is H, $C_{1-6}$ alkyl and q is an integer of 0 to 4 (0, 1, 2, 3 or 4).

In some other embodiments, $R_2$ is a hydrogen atom; $C_{1-6}$ alkyl (e.g., methyl, ethyl, propyl, isopropyl or butyl or isobutyl) optionally substituted with 1 to 3 halogen (e.g., Cl, F, Br, I) or hydroxyl; or phenyl, optionally substituted with 1-5 same or different substituents chosen from halogen (e.g., Cl, F, Br, I), $C_{1-6}$ alkyl optionally substituted with 1 to 3 halogen (e.g., Cl, F, Br, I).

In still other embodiments, $R_2$ is a hydrogen atom; or phenyl, optionally substituted with 1-5 same or different substituents chosen from halogen (e.g., Cl, F, Br, I), and $C_{1-6}$ alkyl optionally substituted with 1 to 3 halogen (e.g., Cl, F, Br, I).

In preferred embodiments, $R_2$ is a hydrogen atom or trifluoromethyl phenyl.

In some embodiments of the present invention, when $R_2$ is an optionally substituted phenyl, $R_3$ is a hydrogen atom; halogen (e.g., Cl, F, Br, I); hydroxyl; $C_{1-6}$ alkyl (e.g., methyl, ethyl, propyl, isopropyl, cyclopropyl, butyl or isobutyl or cyclohexoalkyl) optionally substituted with 1 to 3 halogen (e.g., Cl, F, Br, I) or hydroxyl; $C_{1-6}$ alkoxy optionally substituted with 1 to 3 halogen (e.g., Cl, F, Br, I) or hydroxyl or amino groups. When $R_2$ is not an optionally substituted phenyl, $R_3$ is —$CH_2CH_2$-phenyl, optionally substituted with 1-5 same or different substituents chosen from halogen (e.g., Cl, F, Br, I), $C_{1-6}$ alkyls optionally substituted with 1 to 3 halogen (e.g., Cl, F, Br, I) or hydroxyls, hydroxy, or —$(CH)_qCO_2R_{10}$, wherein $R_{10}$ is a hydrogen atom or a $C_{1-6}$ alkyl, and q is an integer of 0 to 4 (0, 1, 2, 3 or 4).

In still some other embodiments, when $R_2$ is an optionally substituted phenyl, $R_3$ is a hydrogen atom; $C_{1-6}$ alkyl (e.g., methyl, ethyl, propyl, isopropyl, cyclopropyl, butyl or isobutyl or cyclohexoalkyl) optionally substituted with 1 to 3 halogen (e.g., Cl, F, Br, I) or hydroxyl. When $R_2$ is not an optionally substituted phenyl, $R_3$ is —$CH_2CH_2$— phenyl optionally substituted with 1-5 same or different substituents chosen from halogen (e.g., Cl, F, Br, I), $C_{1-6}$ alkyl optionally substituted with 1 to 3 halogen (e.g., Cl, F, Br, I) or hydroxyl, hydroxy, or —$(CH)_qCO_2R_{10}$, wherein $R_{10}$ is a hydrogen atom or a $C_{1-6}$ alkyl, and q is an integer of 0 to 4 (e.g., 0, 1, 2, 3 or 4).

In preferred embodiments, when $R_2$ is an optionally substituted phenyl, $R_3$ is a hydrogen atom; or —$(CH)_qCO_2R_{10}$, wherein $R_{10}$ is a hydrogen atom or a $C_{1-6}$ alkyl, and q is an integer of 0 to 4 (e.g., 0, 1, 2, 3 or 4) (e.g., methyl, ethyl, propyl, isopropyl, cyclopropyl, butyl or isobutyl or cyclohexoalkyl). When $R_2$ is not an optionally substituted phenyl, $R_3$ is —$CH_2CH_2$-phenyl wherein the phenyl group is optionally substituted with 1-5 same or different substituents chosen from halogen (e.g., Cl, F, Br, I) or $C_{1-6}$ alkyl, optionally substituted with 1 to 3 halogen (e.g., Cl, F, Br, I).

In still other preferred embodiments, when $R_2$ is an optionally substituted phenyl, $R_3$ is a hydrogen atom or $C_{1-6}$ alkyl (e.g., methyl, ethyl, propyl, isopropyl, cyclopropyl, butyl or isobutyl or cyclohexoalkyl). When $R_2$ is not an optionally substituted phenyl, $R_3$ is —$CH_2CH_2$-phenyl.

In some embodiments of the present invention, $R_4$ is a hydrogen atom; halogen (e.g., Cl, F, Br, I); hydroxyl; $C_{1-6}$ alkyl (e.g., methyl, ethyl, propyl, isopropyl or butyl or isobutyl) optionally substituted with 1 to 3 halogen (e.g., Cl, F, Br, I) or hydroxyl; $C_{1-6}$ alkoxy optionally substituted with 1 to 3 halogen (e.g., Cl, F, Br, I), hydroxyl or amino groups.

In still some other embodiments, $R_4$ is a hydrogen atom; $C_{1-6}$ alkyl (e.g., methyl, ethyl, propyl, isopropyl or butyl or isobutyl) optionally substituted with 1 to 3 halogen (e.g., Cl, F, Br, I) or hydroxyl; or $C_{1-6}$ alkoxy optionally substituted with 1 to 3 halogen (e.g., Cl, F, Br, I) or hydroxyl.

In preferred embodiments, $R_4$ is a hydrogen atom; or $C_{1-6}$ alkoxy, preferably $C_{1-4}$ alkoxy (e.g., methoxy, ethoxy, propyloxy, etc.).

In some embodiments of the present invention, $R_5$ is a hydrogen atom; halogen (e.g., Cl, F, Br, I); hydroxyl; $C_{1-6}$ alkyl (e.g., methyl, ethyl, propyl, isopropyl or butyl or isobutyl) optionally substituted with 1 to 3 halogen (e.g., Cl, F, Br, I) or hydroxyl; $C_{1-6}$ alkoxy optionally substituted with 1 to 3 halogen (e.g., Cl, F, Br, I), hydroxyl, or amino groups.

In still some other embodiments, $R_5$ is a hydrogen atom; $C_{1-6}$ alkyl (e.g., methyl, ethyl, propyl, isopropyl or butyl or isobutyl) optionally substituted with 1 to 3 halogen (e.g., Cl, F, Br, I) or hydroxyl; or $C_{1-6}$ alkoxy optionally substituted with 1 to 3 halogen (e.g., Cl, F, Br, I) or hydroxyl.

In preferred embodiments, $R_5$ is a hydrogen atom; or $C_{1-6}$ alkoxy, preferably $C_{1-4}$ alkoxy (e.g., methoxy, ethoxy, propyloxy, etc.).

In some embodiments of the present invention, one of $R_6$ and $R_7$ is —$(CH_2)_nCO_2R_{11}$ or —$O(CH_2)_nCO_2R_{11}$, wherein n is an integer from 0 to 6, preferably 0 to 4 (e.g., 0, 1, 2, 3, or 4), and $R_{11}$ is a hydrogen atom, $C_{1-6}$ alkyl (e.g., methyl, ethyl, propyl, isopropyl or butyl or isobutyl) optionally substituted with 1 to 3 halogen (e.g., Cl, F, Br, I); or is —$(CH_2)_mO(CH_2)_pCO_2R_{11}$, wherein m is an integer from 0 to 4 (e.g., 0, 1, 2, 3, or 4), and p is an integer from 1 to 6, preferably 1 to 4 (e.g., 1, 2, 3, or 4), and $R_{11}$ is a hydrogen atom, $C_{1-6}$ alkyl (e.g., methyl, ethyl, propyl, isopropyl or butyl or isobutyl) optionally substituted with 1 to 3 halogen (e.g., Cl, F, Br, I); while the other of $R_6$ and $R_7$ is a hydrogen atom, halogen (Cl, F, Br, I), hydroxy, $C_{1-6}$ alkyl (e.g., methyl, ethyl, propyl, isopropyl or butyl or isobutyl) optionally substituted with 1 to 3 halogen (e.g., Cl, F, Br, I), $C_{1-6}$ alkoxy optionally substituted with 1 to 3 halogen (e.g., Cl, F, Br, I), hydroxyl, or amino groups.

In other embodiments, one of $R_6$ and $R_7$ is —$(CH_2)_nCO_2R_{11}$ or —$O(CH_2)_nCO_2R_{11}$, wherein n is an integer from 0 to 4 (e.g., 0, 1, 2, 3, or 4), and $R_{11}$ is a hydrogen atom, $C_{1-6}$ alkyl (e.g., methyl, ethyl, propyl, isopropyl or butyl or isobutyl) optionally substituted with 1 to 3 halogen (e.g., Cl, F, Br, I); or is —$(CH_2)_mO(CH_2)_pCO_2R_{11}$, wherein m is an integer from 0 to 4 (e.g., 0, 1, 2, 3, or 4), and p is an integer from 1 to 4 (e.g., 1, 2, 3, or 4), and $R_{11}$ is a hydrogen atom, $C_{1-6}$ alkyl (e.g., methyl, ethyl, propyl, isopropyl or butyl or isobutyl) optionally substituted with 1 to 3 halogen (e.g., Cl, F, Br, I); while the other of $R_6$ and $R_7$ is a hydrogen atom, halogen (Cl, F, Br, I), hydroxy, $C_{1-6}$ alkyl (e.g., methyl, ethyl, propyl, isopropyl or butyl or isobutyl) optionally substituted with 1 to 3 halogen (e.g., Cl, F, Br, I), $C_{1-6}$ alkoxy optionally substituted with 1 to 3 halogen (e.g., Cl, F, Br, I), hydroxyl, or amino groups.

In preferred embodiments, one of $R_6$ and $R_7$ is —$(CH_2)_nCO_2R_{11}$ or —$O(CH_2)$—$CO_2R_{11}$, wherein n is an integer from 0 to 4 (e.g., 0, 1, 2, 3, or 4), and $R_{11}$ is a hydrogen atom; or is —$(CH_2)_mO(CH_2)_pCO_2R_{11}$, wherein m is an integer from 0 to 4 (e.g., 0, 1, 2, 3, or 4), and p is an integer from 1 to 4 (e.g., 1, 2, 3, or 4), and $R_{11}$ is a hydrogen atom; while the other of $R_6$ and $R_7$ is a hydrogen atom, halogen (Cl, F, Br, I), hydroxy, $C_{1-6}$ alkyl (e.g., methyl, ethyl, propyl, isopropyl or butyl or isobutyl) optionally substituted with 1 to 3 halogen (e.g., Cl, F, Br, I), $C_{1-6}$ alkoxy optionally substituted with 1 to 3 halogen (e.g., Cl, F, Br, I), hydroxyl, or amino groups.

In still other preferred embodiments, one of $R_6$ and $R_7$ is —$(CH_2)_nCO_2R_{11}$ or —$O(CH_2)_nCO_2R_{11}$, wherein n is an integer from 0 to 4 (e.g., 0, 1, 2, 3, or 4), and $R_{11}$ is a hydrogen atom; or is —$(CH_2)_mO(CH_2)_pCO_2R_{11}$, wherein m is an integer from 0 to 4 (e.g., 0, 1, 2, 3, or 4), and p is an integer from 1 to 4 (e.g., 1, 2, 3, or 4), and $R_{11}$ is a hydrogen atom; while the other of $R_6$ and $R_7$ is a hydrogen atom.

In some embodiments of the present invention, $R_8$ is a hydrogen atom; halogen (e.g., Cl, F, Br, I); hydroxyl; $C_{1-6}$ alkyl (e.g., methyl, ethyl, propyl, isopropyl or butyl or isobutyl) optionally substituted with 1 to 3 halogen (e.g., Cl, F, Br, I) or hydroxyl; $C_{1-6}$ alkoxy optionally substituted with 1 to 3 halogen (e.g., Cl, F, Br, I), hydroxyl, or amino groups.

In other embodiments, $R_8$ is a hydrogen atom; $C_{1-6}$ alkyl (e.g., methyl, ethyl, propyl, isopropyl or butyl or isobutyl) optionally substituted with 1 to 3 halogen (e.g., Cl, F, Br, I) or hydroxyl; or $C_{1-6}$ alkoxy optionally substituted with 1 to 3 halogen (e.g., Cl, F, Br, I) or hydroxyl.

In preferred embodiments, $R_8$ is a hydrogen atom; or $C_{1-6}$ alkoxy, preferably $C_{1-4}$ alkoxy (e.g., methoxy, ethoxy, propyloxy, etc.).

In some embodiments of the present invention, $R_9$ and $R_{12}$ are independently from 0 to 5 (e.g., 0, 1, 2, 3, 4, or 5) phenyl substituents, which are independently selected from a hydrogen atom, halogen (e.g., Cl, F, Br, I), hydroxyl, $C_{1-6}$ alkyl (e.g., methyl, ethyl, propyl, isopropyl or butyl or isobutyl) optionally substituted with 1 to 3 halogen (e.g., Cl, F, Br, I) or hydroxyl groups, haloalkyl (e.g., trifluoromethyl), aryl, heteroaryl, heterocycle, —OR, —C(=O)R, —C(=O)OR, —C(=O)NRR, —NRR, —NRC(=O)R, —NRC(=O)OR, —NRC(=O)NRR, —OC(=O)R, —OC(=O)OR, —OC(=O)NRR, —SH, —SR, —SOR, —SO$_2$R, —SO$_2$NR$_2$, —NRSO$_2$R, —NR$_2$SO$_2$R, —Si(R)$_3$, or —OP(OR)$_3$, wherein each occurrence of R is the same or different and independently a hydrogen atom, $C_{1-6}$ alkyl (e.g., methyl, ethyl, propyl, isopropyl or butyl or isobutyl), substituted alkyl, aryl, substituted aryl, arylalkyl, substituted arylalkyl, heterocycle, substituted heterocycle, heterocyclealkyl or substituted heterocyclealkyl, or wherein any two R groups attached to the same nitrogen atom, taken together with the nitrogen atom to which they are attached, form a heterocyclic ring or a substituted heterocyclic ring.

In other embodiments of the present invention, $R_9$ and $R_{12}$ are independently from 0 to 5 (e.g., 0, 1, 2, 3, 4, or 5) phenyl substituents, which are independently selected from a hydrogen atom, halogen (e.g., Cl, F, Br, I), hydroxyl, $C_{1-6}$ alkyl (e.g., methyl, ethyl, propyl, isopropyl or butyl or isobutyl) optionally substituted with 1 to 3 halogen (e.g., Cl, F, Br, I) or hydroxyl groups, $C_{1-6}$ haloalkyl (e.g., trifluoromethyl), $C_{1-6}$ alkoxy, or aryl.

In still other embodiments of the present invention, $R_9$ and $R_{12}$ are independently from 0 to 5 (e.g., 0, 1, 2, 3, 4, or 5) phenyl substituents, which independently selected from a hydrogen atom, halogen (e.g., Cl, F, Br, I), hydroxyl, $C_{1-6}$ haloalkyl (e.g., trifluoromethyl), or $C_{1-6}$ alkoxy.

In preferred embodiments of the present invention, $R_9$ and $R_{12}$ are independently from 0 to 5 (e.g., 0, 1, 2, 3, 4, or 5) phenyl substituents, which are independently selected from a hydrogen atom, halogen (e.g., Cl, F, Br, I), hydroxyl, or $C_{1-4}$ haloalkyl (e.g., trifluoromethyl).

In one particular set of embodiments, $R_1$, $R_5$ and $R_8$ are hydrogen atoms, and the compounds, and pharmaceutically acceptable salts, esters, hydrates or solvates thereof, are in accordance with Formula II:

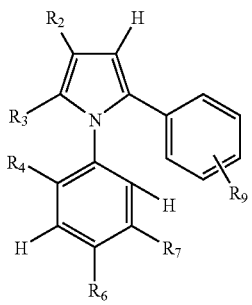

(II)

wherein $R_2$, $R_3$, $R_4$, $R_6$, $R_7$, and $R_9$ are as defined above.

In another particular set of embodiments of the present invention $R_2$ is phenyl, or substituted phenyl, and $R_3$ is either a hydrogen atom, halogen (Cl, F, Br, I), hydroxy, alkyl, substituted alkyl, alkoxy, or substituted alkoxy, such that, in this set of embodiments, the compounds, and pharmaceutically acceptable salts, esters, hydrates or solvates thereof correspond to Formula III:

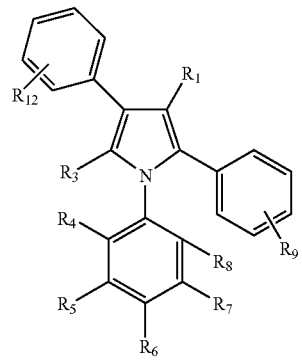

(III)

wherein $R_1$, $R_4$, $R_5$, $R_6$, $R_7$, $R_8$, $R_9$ and $R_{12}$ are as defined above.

In a subset of these embodiments, $R_1$, $R_5$ and $R_8$ are hydrogen atoms, and the compounds, and pharmaceutically acceptable salts, esters, hydrates or solvates thereof are in accordance with Formula IV:

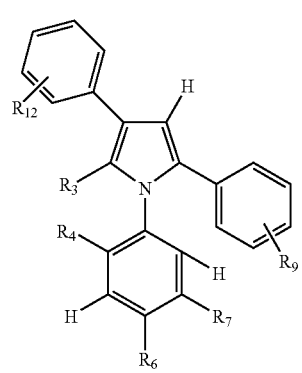

(IV)

wherein $R_3$, $R_4$, $R_6$, $R_7$, $R_9$ and $R_{12}$ are as defined above.

In another particular set of embodiments of the present invention $R_2$ is either a hydrogen atom, halogen (Cl, F, Br, I), hydroxy, alkyl, substituted alkyl, alkoxy, or substituted alkoxy, and $R_3$ is —CH$_2$CH$_2$-phenyl, such that, in this set of embodiments, the compounds, and pharmaceutically acceptable salts, esters, hydrates or solvates thereof correspond to Formula V:

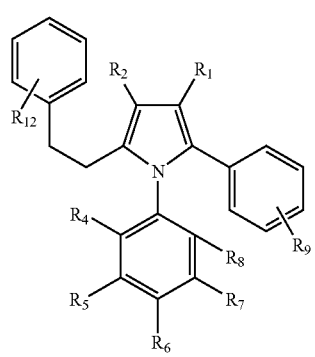

(V)

wherein $R_1$, $R_4$, $R_5$, $R_6$, $R_7$, $R_8$, $R_9$ and $R_{12}$ are as defined above.

In a subset of these embodiments, $R_1$, $R_5$ and $R_8$ are hydrogen atoms, and the compounds, and pharmaceutically acceptable salts, esters, hydrates or solvates thereof are in accordance with Formula VI:

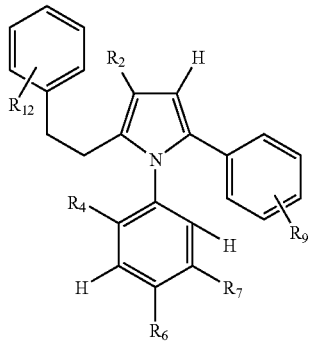

(VI)

wherein $R_2$, $R_4$, $R_6$, $R_7$, $R_9$, and $R_{12}$ are as defined above.

It should be noted that in most embodiments of the present invention, one of either of $R_6$ or $R_7$ is —$(CH_2)_nCO_2H$, or —$O(CH_2)$—$CO_2H$, wherein n is an integer from 0 to 4, or —$(CH_2)_mO(CH_2)_pCO_2H$, wherein m is an integer from 1 to 2 and p is an integer from 1 to 2, while the other of $R_6$ or $R_7$ is a hydrogen atom, halogen, hydroxy, alkyl, substituted alkyl, alkoxy, or substituted alkoxy. While not wishing to be bound by theory, the presence of a carboxyl group, in the form of a carboxylic acid substituent at one of these two positions ($R_6$ or $R_7$) may be important for the efficacy of the compound in inhibiting $A\beta_{42}$ secretion. As indicated, in certain embodiments of the present invention, the carboxylic acid substituent is linked directly to the aromatic ring at either $R_6$ or $R_7$. In other embodiments, the carboxylic acid substituent is linked through an ether linkage to the aromatic ring at either $R_6$ or $R_7$. In either case, the carboxylic acid group can be appended to either the $R_6$ or the $R_7$ position, although substitution at the $R_7$ position may be preferred.

It should also be noted that the carboxylic acid group appended to either the $R_6$ or the $R_7$ position can potentially be created by the hydrolytic cleavage of an ester. Consequently, in certain embodiments, the compounds of the present invention further include such esters of all compounds according to Formulae I-VI. (See, for example Compound #27 in Table 1, below.) Such esters can include methyl esters and ethyl esters, as well as other lower alkyl esters.

In other embodiments of the present invention, in all compounds according to Formulae I-VI, one of either $R_6$ or $R_7$ is substituted with a bioisostere of carboxylic acid, including: -L-C(=O)OH, -L-CH=CHC(=O)OH, -L-C(=O)NH$_2$, -L-C(=O)NH(C$_{1-3}$ alkyl), -L-C(=O)N(C$_{1-3}$ alkyl)$_2$, -L-S(=O)$_2$(C$_{1-3}$alkyl), -L-S(=O)$_2$NH$_2$, -L-S(=O)$_2$N(C$_{1-3}$ alkyl)$_2$, -L-S(=O)$_2$NH(C$_{1-3}$ alkyl), -L-C(=O)NHOH, -L-C(=O)CH$_2$NH$_2$, —LC(=O)CH$_2$OH, L-C(=O)CH$_2$SH, -L-C(=O)NHCN, -L-sulfo, -L-(2,6 difluorophenol), -L-phosphono, and -L-tetrazolyl;

wherein L can be saturated, partially saturated, or unsaturated, and is selected from the group consisting of —$(CH_2)_n$—$(CH2)_n$—, —$(CH_2)_nC(=O)(CH_2)_n$—, —$(CH_2)_nNH(CH_2)_n$—, —$(CH2)_nO(CH_2)_n$—, and —$(CH_2)_nS(CH_2)_n$, wherein each n is an integer independently selected from 0, 1, 2, 3, 4, 5, 6, 7, and 8, wherein each carbon can be optionally substituted with one or more $C_{1-3}$ alkyl or $C_{3-6}$ cycloalkyl. However, the compounds of the present invention specifically exclude the compound 4-[2-(4-Fluoro-phenyl)-4-phenyl-pyrrol-1-yl]-benzenesulfonamide (CAS REGISTRY No. 197904-68-0).

In certain embodiments, the present invention provides the specific compounds identified in Table 1, below.

TABLE 1

Exemplary Compounds

| Compound No. | Compound Structure | MW | Compound Name |
|---|---|---|---|
| 1 | 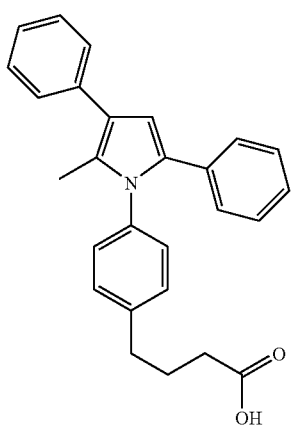 | 395.50 | 4-[4-(2-Methyl-3,5-diphenyl-pyrrol-1-yl)-phenyl]-butyric acid |

TABLE 1-continued

Exemplary Compounds

| Compound No. | Compound Structure | MW | Compound Name |
|---|---|---|---|
| 2 | 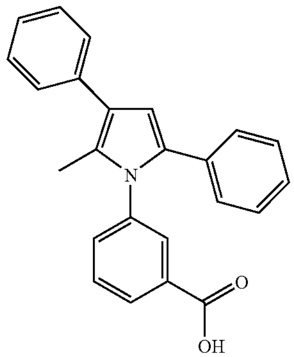 | 353.42 | 3-(2-Methyl-3,5-diphenyl-pyrrol-1-yl)-benzoic acid |
| 3 | 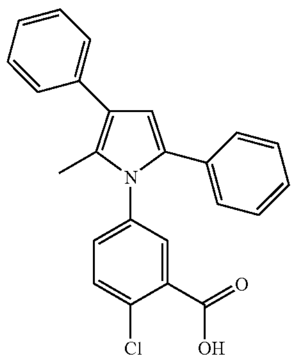 | 387.86 | 2-Chloro-5-(2-methyl-3,5-diphenyl-pyrrol-1-yl)-benzoic acid |
| 4 | 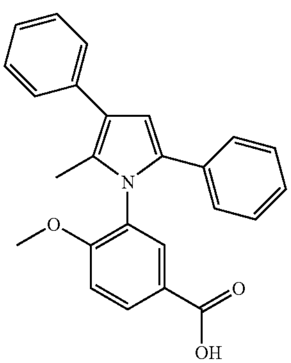 | 383.44 | 4-Methoxy-3-(2-methyl-3,5-diphenyl-pyrrol-1-yl)-benzoic acid |
| 5 | 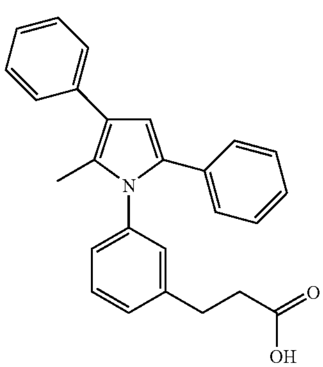 | 381.47 | 3-[3-(2-Methyl-3,5-diphenyl-pyrrol-1-yl)-phenyl]-propionic acid |

TABLE 1-continued

Exemplary Compounds

| Compound No. | Compound Structure | MW | Compound Name |
|---|---|---|---|
| 6 | 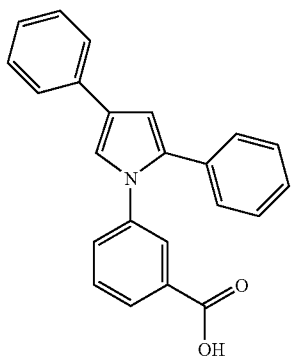 | 339.39 | 3-(2,4-Diphenyl-pyrrol-1-yl)-benzoic acid |
| 7 | 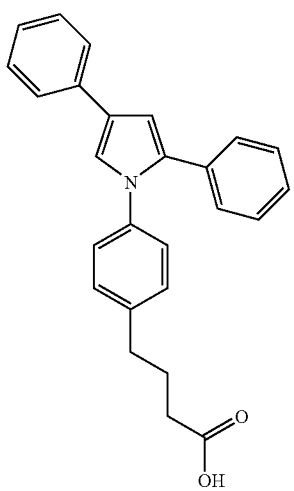 | 381.47 | 4-[4-(2,4-Diphenyl-pyrrol-1-yl)-phenyl]-butyric acid |
| 8 | 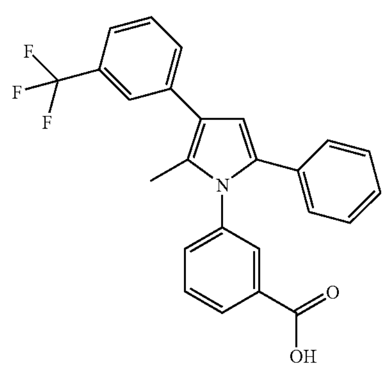 | 421.42 | 3-[2-Methyl-5-phenyl-3-(3-trifluoromethyl-phenyl)-pyrrol-1-yl]-benzoic acid |

TABLE 1-continued
Exemplary Compounds
| Compound No. | Compound Structure | MW | Compound Name |
|---|---|---|---|
| 9 | 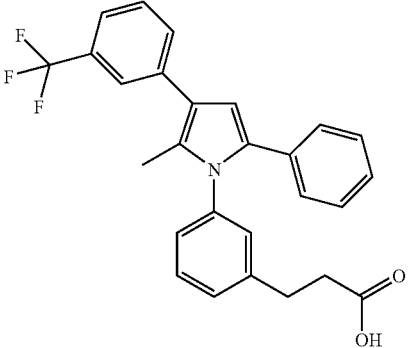 | 449.47 | 3-{3-[2-Methyl-5-phenyl-3-(3-trifluoromethyl-phenyl)-pyrrol-1-yl]-phenyl}-propionic acid |
| 10 | 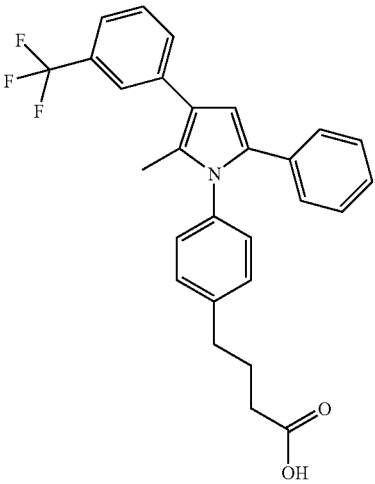 | 463.50 | 4-{4-[2-Methyl-5-phenyl-3-(3-trifluoromethyl-phenyl)-pyrrol-1-yl]-phenyl}-butyric acid |
| 11 | 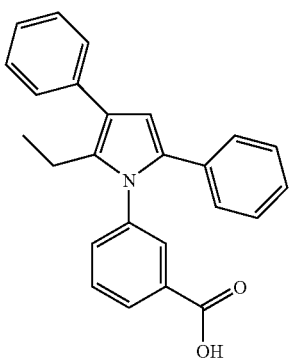 | 367.45 | 3-(2-Ethyl-3,5-diphenyl-pyrrol-1-yl)-benzoic acid |

TABLE 1-continued
Exemplary Compounds
| Compound No. | Compound Structure | MW | Compound Name |
|---|---|---|---|
| 12 | 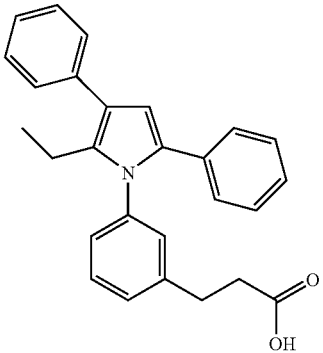 | 395.50 | 3-[3-(2-Ethyl-3,5-diphenyl-pyrrol-1-yl)-phenyl]-propionic acid |
| 13 | 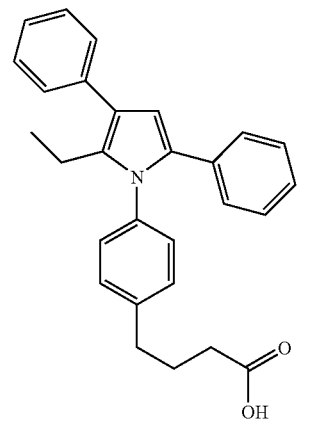 | 409.53 | 4-[4-(2-Ethyl-3,5-diphenyl-pyrrol-1-yl)-phenyl]-butyric acid |
| 14 | 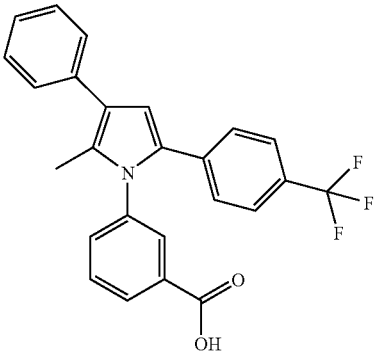 | 421.42 | 3-[2-Methyl-3-phenyl-5-(4-trifluoromethyl-phenyl)-pyrrol-1-yl]-benzoic acid |
| 15 | 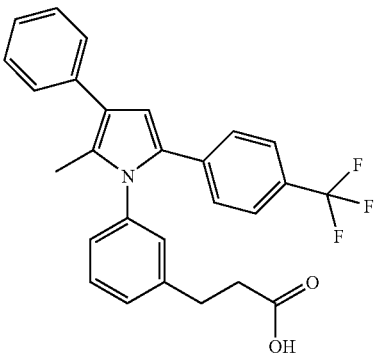 | 449.47 | 3-{3-[2-Methyl-3-phenyl-5-(4-trifluoromethyl-phenyl)-pyrrol-1-yl]-phenyl}-propionic acid |

TABLE 1-continued

Exemplary Compounds

| Compound No. | Compound Structure | MW | Compound Name |
|---|---|---|---|
| 16 | 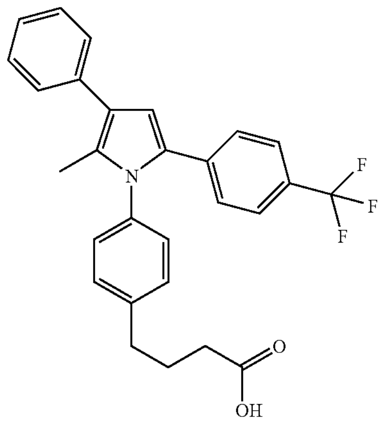 | 463.50 | 4-{4-[2-Methyl-3-phenyl-5-(4-trifluoromethyl-phenyl)-pyrrol-1-yl]-phenyl}-butyric acid |
| 17 | 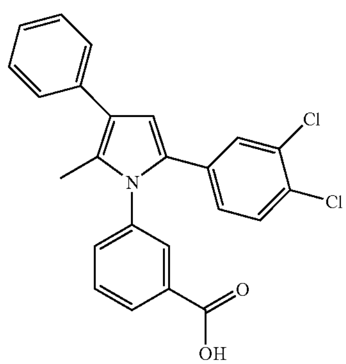 | 422.31 | 3-[5-(3,4-Dichloro-phenyl)-2-methyl-3-phenyl-pyrrol-1-yl]-benzoic acid |
| 18 | 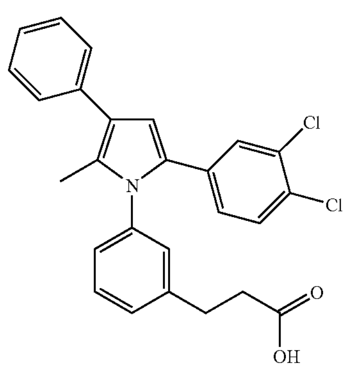 | 450.36 | 3-{3-[5-(3,4-Dichloro-phenyl)-2-methyl-3-phenyl-pyrrol-1-yl]-phenyl}-propionic acid |

TABLE 1-continued

Exemplary Compounds

| Compound No. | Compound Structure | MW | Compound Name |
|---|---|---|---|
| 19 | 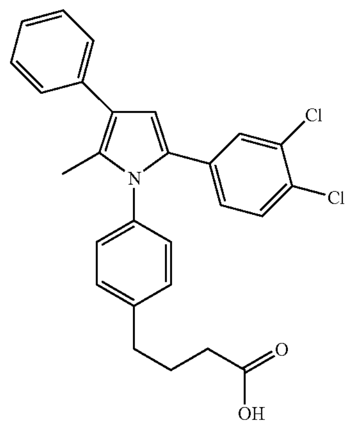 | 464.39 | 4-{4-[5-(3,4-Dichloro-phenyl)-2-methyl-3-phenyl-pyrrol-1-yl]-phenyl}-butyric acid |
| 20 | 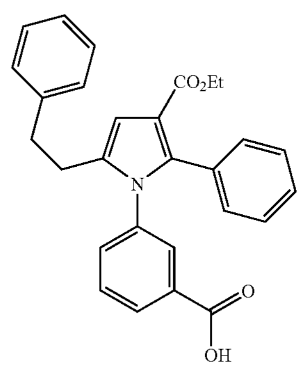 | 439.51 | 1-(3-Carboxy-phenyl)-5-phenethyl-2-phenyl-1H-pyrrole-3-carboxylic acid ethyl ester |
| 21 | 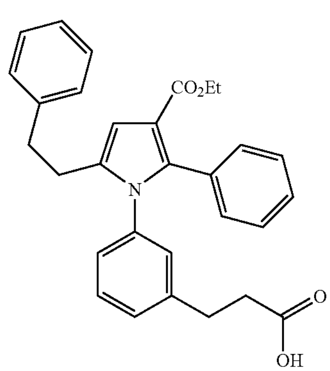 | 467.56 | 1-[3-(2-Carboxy-ethyl)-phenyl]-5-phenethyl-2-phenyl-1H-pyrrole-3-carboxylic acid ethyl ester |

TABLE 1-continued

| Exemplary Compounds | | | |
| --- | --- | --- | --- |
| Compound No. | Compound Structure | MW | Compound Name |
| 22 | | 481.59 | 1-[4-(3-Carboxy-propyl)-phenyl]-5-phenethyl-2-phenyl-1H-pyrrole-3-carboxylic acid ethyl ester |
| 23 | | 367.45 | 3-(2-Phenethyl-5-phenyl-pyrrol-1-yl)-benzoic acid |
| 24 | | 395.50 | 3-[3-(2-Phenethyl-5-phenyl-pyrrol-1-yl)-phenyl]-propionic acid |

TABLE 1-continued

Exemplary Compounds

| Compound No. | Compound Structure | MW | Compound Name |
|---|---|---|---|
| 25 | 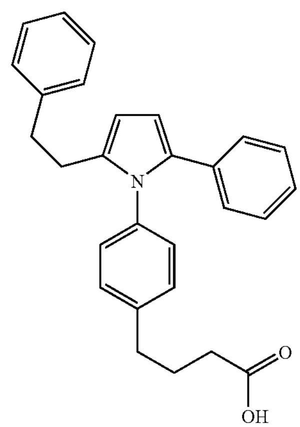 | 409.53 | 4-[4-(2-Phenethyl-5-phenyl-pyrrol-1-yl)-phenyl]-butyric acid |
| 26 | 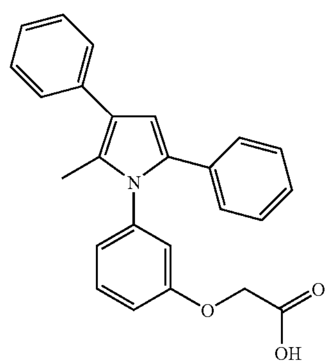 | 383.44 | [3-(2-Methyl-3,5-diphenyl-pyrrol-1-yl)-phenoxy]-acetic acid |
| 27 | 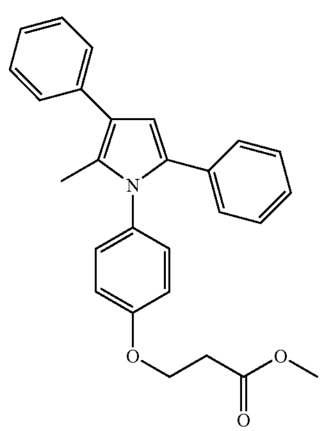 | 411.50 | 3-[4-(2-Methyl-3,5-diphenyl-pyrrol-1-yl)-phenoxy]-propionic acid methyl ester |

TABLE 1-continued
Exemplary Compounds
| Compound No. | Compound Structure | MW | Compound Name |
|---|---|---|---|
| 28 | 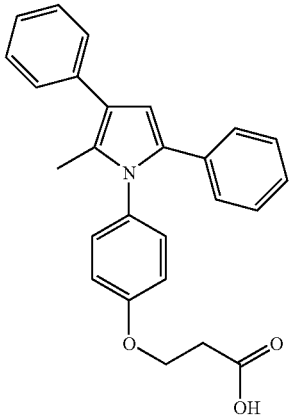 | 397.47 | 3-[4-(2-Methyl-3,5-diphenyl-pyrrol-1-yl)-phenoxy]-propionic acid |
| 29 | 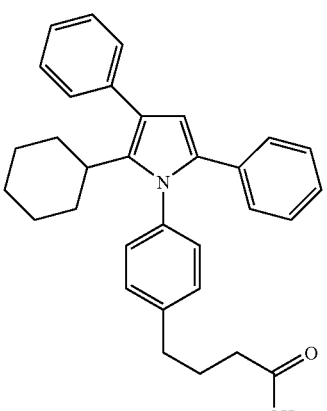 | 463.62 | 4-[4-(2-Cyclohexyl-3,5-diphenyl-pyrrol-1-yl)-phenyl]-butyric acid |
| 30 | 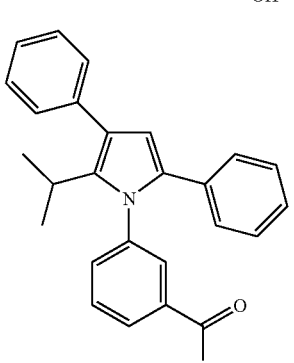 | 381.47 | 3-(2-Isopropyl-3,5-diphenyl-pyrrol-1-yl)-benzoic acid |
| 31 | 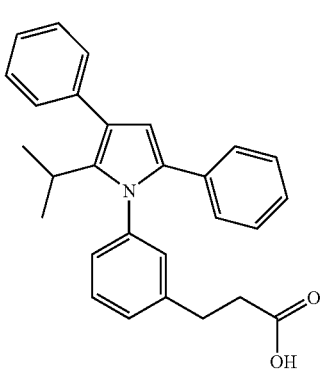 | 409.53 | 3-[3-(2-Isopropyl-3,5-diphenyl-pyrrol-1-yl)-phenyl]-propionic acid |

TABLE 1-continued

Exemplary Compounds

| Compound No. | Compound Structure | MW | Compound Name |
|---|---|---|---|
| 32 | 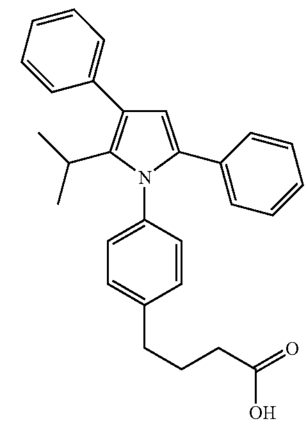 | 423.55 | 4-[4-(2-Isopropyl-3,5-diphenyl-pyrrol-1-yl)-phenyl]-butyric acid |
| 33 | 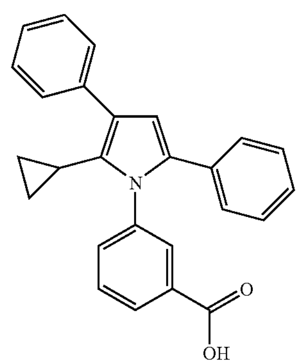 | 379.46 | 3-(2-Cyclopropyl-3,5-diphenyl-pyrrol-1-yl)-benzoic acid |
| 34 | 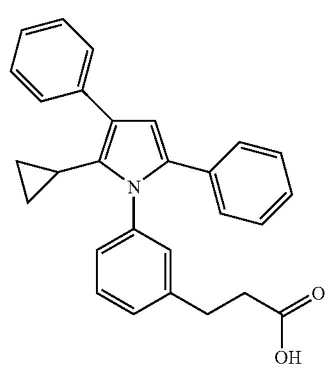 | 407.51 | 3-[3-(2-Cyclopropyl-3,5-diphenyl-pyrrol-1-yl)-phenyl]-propionic acid |

TABLE 1-continued

| Exemplary Compounds | | | |
|---|---|---|---|
| Compound No. | Compound Structure | MW | Compound Name |
| 35 | | 421.54 | 4-[4-(2-Cyclopropyl-3,5-diphenyl-pyrrol-1-yl)-phenyl]-butyric acid |
| 36 | | 409.53 | 3-[2-(2,2-Dimethyl-propyl)-3,5-diphenyl-pyrrol-1-yl]-benzoic acid |
| 37 | | 437.58 | 3-{3-[2-(2,2-Dimethyl-propyl)-3,5-diphenyl-pyrrol-1-yl]-phenyl}-propionic acid |

TABLE 1-continued

Exemplary Compounds

| Compound No. | Compound Structure | MW | Compound Name |
|---|---|---|---|
| 38 | 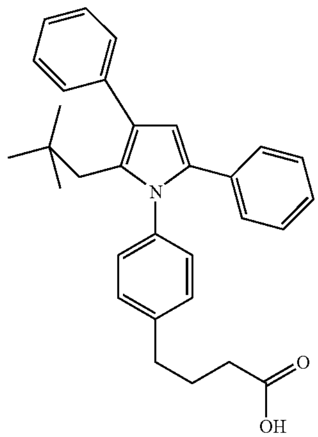 | 451.61 | 4-{4-[2-(2,2-Dimethyl-propyl)-3,5-diphenyl-pyrrol-1-yl]-phenyl}-butyric acid |
| 39 | 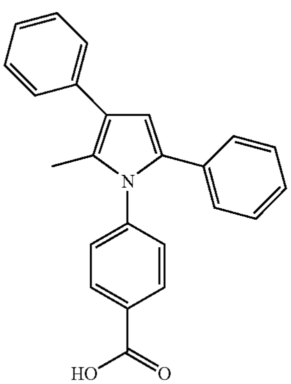 | 353.42 | 4-(2-Methyl-3,5-diphenyl-pyrrol-1-yl)-benzoic acid |

Without wishing to be bound by theory, it is believed that the compounds of the present invention can reduce the secretion of $A\beta_{42}$ peptide by cells within the brains of patients and thereby lower $A\beta_{42}$ peptide concentrations in the patients' brains, and reduce the rate of formation or deposition of amyloid plaques comprising the $A\beta_{42}$ peptide. In so doing, it is believed that the compounds of the present invention are useful for treating and/or preventing neurodegenerative diseases characterized by the deposition of amyloid plaques comprising the $A\beta_{42}$ peptide, according to the methods of the invention. Thus, in one aspect of this invention, which is described in detail below, methods of treating AD, MCI, CAA, or DS-associated dementia are provided comprising identifying a patient in need of such treatment, and administering to that patient an $A\beta_{42}$-lowering, effective amount of a compound of the present invention. Preferably, the compound that is used in the methods of the invention is capable of reducing $A\beta_{42}$ secretion by cells by at least 10, 20, 30, 40, or 50 percent, at a concentration of 100 μM in an assay of $A\beta_{42}$ secretion, such as described in the Examples below.

Preferred compounds for use in the methods of the invention are those that have an IC50, in an assay of $A\beta_{42}$ secretion as described in the Examples below, of 100 μM or less, more preferably 10 μM or less, and even more preferably 1 μM or less.

It is understood that while the compounds for use in the invention may exhibit the phenomenon of tautomerism, the formula drawings within this specification expressly depict only one of the possible tautomeric forms. It is therefore to be understood that within this specification the formulae are intended to represent any tautomeric form of the depicted compound, and the depicted compounds are not to be limited merely to a specific tautomeric form depicted by a formula drawing.

Some of the compounds for use in the invention may exist as single stereoisomers (i.e., essentially free of other stereoisomers), racemates, and/or mixtures of enantiomers and/or diastereomers. All such single stereoisomers, racemates and mixtures thereof are intended to be within the scope of the present invention. Preferably, the inventive compounds that are optically active are used in an optically pure form.

Additionally, the compounds of the present invention can have asymmetric centers and/or can exist in the form of cis or trans derivatives. The invention covers the racemates, mixtures of cis and trans compounds, and also covers optically active products with the cis derivatives and the trans derivatives taken independently. These pure products will be obtained by the methods known to those skilled in the art, in particular by chromatography, especially on chiral columns in the case of optical isomers.

Importantly, the Formulae presented above are intended to cover solvated as well as unsolvated forms of the identified structures. For example, Formulae I-VI include compounds of the indicated structure in both hydrated and non-hydrated forms. Other examples of solvates include the structures in combination with isopropanol, ethanol, methanol, DMSO, ethyl acetate, acetic acid, or ethanolamine.

In addition to compounds of the Formulae I-VI, and those compounds specifically identified in Table 1, the invention includes pharmaceutically acceptable prodrugs, pharmaceutically active metabolites, and pharmaceutically acceptable salts of such compounds.

A "pharmaceutically acceptable prodrug" is a compound that may be converted under physiological conditions or by solvolysis to the specified compound or to a pharmaceutically acceptable salt of such compound.

A "pharmaceutically active metabolite" is intended to mean a pharmacologically active product produced through metabolism in the body of a specified compound or salt thereof. Metabolites of a compound may be identified using routine techniques known in the art and their activities determined using tests such as those described herein.

Prodrugs and active metabolites of compound may be identified using routine techniques known in the art. See, e.g., Bertolini, G. et al., *J. Med. Chem.*, 40, 2011-2016 (1997); Shan, D. et al., *J. Pharm. Sci.*, 86 (7), 756-767; Bagshawe K., *Drug Dev. Res.*, 34, 220-230 (1995); Bodor, N.; *Advance in Drug Res.*, 13, 224-331 (1984); Bundgaard, H., *Design of Prodrugs* (Elsevier Press 1985); and Larsen, I. K., *Design and Application of Prodrugs, Drug Design and Development* (Krogsgaard-Larsen et al., eds., Harwood Academic Publishers, 1991).

"A pharmaceutically acceptable salt" is intended to mean a salt that retains the biological effectiveness of the free acids and bases of the specified compound and that is not biologically or otherwise undesirable. A compound for use in the invention may possess a sufficiently acidic, a sufficiently basic, or both functional groups, and accordingly react with any of a number of inorganic or organic bases, and inorganic and organic acids, to form a pharmaceutically acceptable salt. Exemplary pharmaceutically acceptable salts include those salts prepared by reaction of the compounds of the present invention with a mineral or organic acid or an inorganic base, such as salts including sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4 dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, gamma.-hydroxybutyrates, glycollates, tartrates, methane-sulfonates, propanesulfonates, naphthalene-1-sulfonates, naphthalene-2-sulfonates, and mandelates.

If the compound for use in the invention is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the inventive compound is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium. These substituents may optionally be further substituted with a substituent selected from such groups.

Pharmaceutical Compositions

The present invention also provides pharmaceutical compositions comprising a therapeutic $A\beta_{42}$-lowering compound according to the present invention and a pharmaceutically acceptable excipient or carrier. Such pharmaceutical compositions are formulated so as to deliver a therapeutically or prophylactically effective amount of the therapeutic compound to a patient in need of such treatment.

When the composition having a compound of Formulae I-VI is administered, according to the treatment regimens of the invention, to an individual desiring or needing such treatment, it provides an improvement or lessening of a decline in cognitive function, a biochemical disease marker, and/or amyloid plaque morphology and pathology associated with a neurodegenerative disorder characterized by the formation or accumulation of amyloid plaques. The pharmaceutical composition of the invention is formulated with one or more pharmaceutically acceptable salts, excipients, or carriers. The pharmaceutical composition can be delivered orally, preferably in a tablet or capsule dosage form, or by any other effective route.

In a specific embodiment of this aspect of the invention, the dosage is provided as a pharmaceutical composition that is composed of an effective amount of a compound of Formulae I-VI, a pharmaceutically acceptable salt, a release agent, a carrier or excipient, and additional optional ingredients.

Typically, compounds according to Formulae I-VI can be effective at an amount of from about 0.01 μg/kg, to about 100 mg/kg, per day based on total body weight. The active ingredient (or ingredients if more than one compound according to Formulae I-VI is used for therapy) may be administered all at one time, or may be divided into a number of smaller doses to be administered at predetermined intervals of time. The suitable dosage unit for each administration can be, e.g., from about 1 μg to about 2000 mg, preferably from about 5 μg to about 1000 mg. In the case of combination therapy (below), a therapeutically effective amount of one or more other therapeutic compounds can be administered in a separate pharmaceutical composition, or alternatively included in the pharmaceutical composition according to the present invention, which contains a compound according to Formulae I-VI. The pharmacology and toxicology of many of such other therapeutic compounds are known in the art. See e.g., *Physicians Desk Reference*, Medical Economics, Montvale, N.J.; and *The Merck Index*, Merck & Co., Rahway, N.J. The therapeutically effective amounts and suitable unit dosage ranges of such compounds used in art can be equally applicable in the present invention.

It should be understood that the dosage ranges set forth above are exemplary only and are not intended to limit the scope of this invention. The therapeutically effective amount for each active compound can vary with factors including but not limited to the activity of the compound used, stability of the active compound in the patient's body, the severity of the conditions to be alleviated, the total weight of the patient to be treated, the route of administration, the ease of absorption, distribution, and excretion of the active compound by the body, the age and sensitivity of the patient to be treated, and the like, as will be apparent to a skilled artisan. The amount of administration can be adjusted as such factors change over time.

Formulations

The pills, tablets, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

Soft gelatin capsules can be prepared in which capsules contain a mixture of the active ingredient and vegetable oil or non-aqueous, water miscible materials such as, for example, polyethylene glycol and the like. Hard gelatin capsules may contain granules of the active ingredient in combination with a solid, pulverulent carrier, such as, for example, lactose, saccharose, sorbitol, mannitol, potato starch, corn starch, amylopectin, cellulose derivatives, or gelatin.

Tablets for oral use are typically prepared in the following manner, although other techniques may be employed. The solid substances are ground or sieved to a desired particle size, and the binding agent is homogenized and suspended in a suitable solvent. The active ingredient and auxiliary agents are mixed with the binding agent solution. The resulting mixture is moistened to form a uniform suspension. The moistening typically causes the particles to aggregate slightly, and the resulting mass is gently pressed through a stainless steel sieve having a desired size. The layers of the mixture are then dried in controlled drying units for determined length of time to achieve a desired particle size and consistency. The granules of the dried mixture are gently sieved to remove any powder. To this mixture, disintegrating, anti-friction, and anti-adhesive agents are added. Finally, the mixture is pressed into tablets using a machine with the appropriate punches and dies to obtain the desired tablet size. The operating parameters of the tablet-forming machine are selected by the skilled artisan.

Therapeutic Methods

The present invention provides therapeutic methods for use in treating patients in need of such treatments. These methods generally comprise administration of an effective amount of an $A\beta_{42}$-lowering pyrrole derivative of the present invention to a patient in need of such treatment, through the administration of a pharmaceutical composition of the present invention.

As a first step, the therapeutic methods of present invention require the identification of patients in need of such treatment. This first step can be achieved by way of any of the appropriate techniques known in the art, including assessment of cognitive function, assays for biochemical markers, and/or determination of amyloid plaque number, density, size or morphology.

The decline in cognitive function observed in neurodegenerative diseases such as AD can be characterized by cognition tests. It is preferred that the lessening in decline in cognitive function is at least 25% as compared to individuals treated with placebo, more preferably at least 40%, and even more preferably at least 60%.

In certain embodiments, the present invention relates to a method of preventing AD, or significantly delaying the onset of its symptoms. According to this embodiment, a method for preventing AD is provided which comprises administering, to an individual in need of such treatment, a composition comprising a therapeutically effective amount of a compound according to Formulae I-VI. The method of this embodiment is useful for preventing or delaying the onset of the symptoms of AD, the onset of AD, and/or the progression of the disease. In these embodiments the patient in need of such treatment may be one who has yet to exhibit symptoms of AD, but is at risk of developing the disease. Alternatively, the patient to be treated may suffer from MCI, but who has yet to be clinically diagnosed with AD. Individuals at risk of developing AD can be identified by any acceptable method in the art. As noted above, such methods can include genotyping by any suitable method, analysis of family history of the disease, or through pedigree analysis. Methods of determining risk through genotyping include determining genotype by nucleic acid sequencing, selective hybridization, allele-specific amplification, and the like. Additionally, various biomarkers, such as $A\beta_{42}$ peptide concentrations in plasma or serum, or amyloid plaque number, density, size and morphology, can be used to assess whether an individual is at risk of developing a neurodegenerative disease that can be treated or prevented using the methods of the present invention.

The above various methods of the present invention can also be practiced by, or can comprise, treating cells in vitro or a warm-blood animal, particularly mammal, more particularly a human with an effective amount of a compound according to the present invention. As used herein, the phrase "treating . . . with . . . a compound" means either administering the compound to cells or an animal, or administering to cells or an animal the compound or another agent to cause the presence or formation of the compound inside the cells or the animal. Preferably, the methods of the present invention comprise administering to cells in vitro or to a warm-blood animal, particularly mammal, more particularly a human a pharmaceutical composition comprising an effective amount of a compound according to the present invention.

Patient Population

Any individual having, or suspected of having, a neurodegenerative disorder, such as AD, MCI, CAA, or DS-associated dementia can be treated using the compositions and methods of the present invention. Individuals who would particularly benefit from the compositions and methods of the invention include those individuals diagnosed as having mild to moderate AD according to a medically-accepted diagnosis, such as, for example the NINCDS-ADRDA criteria. Progression of the disease may be followed by medically accepted measure of cognitive function, such as, for example, the Mini-Mental State Exam (MMSE; see Mohs et al. *Int. Psychogeriatr.* 8:195-203 (1996)); ADAS-Cog (Alzheimer Disease Assessment Scale-Cognitive; see Galasko et al. *Alzheimer Dis. Assoc. Disord.* 11 suppl 2:S33-9 (1997)); Behavioral Pathology in Alzheimer's Disease Rating Scale (BEHAVE-AD); Blessed Test; CANTAB—Cambridge Neuropsychological Test Automated Battery; CERAD (The Consortium to Establish a Registry for Alzheimer's Disease) Clinical and Neuropsychological Tests (includes MMSE); Clock Draw Test; Cornell Scale for Depression in Dementia (CSDD); Geriatric Depression Scale (GDS); Neuropsychiatric Inventory (NPI); the 7 Minute Screen; the Alzheimer's Disease Cooperative Study Activities of Daily Living scale (ADCS-ADL; see McKhann et al. Neurology 34:939-944 (1984)); the DSM-IV (Diagnostic and Statistical Manual of Mental Disorders—Fourth Edition (DSM-IV), published by the American Psychiatric Association, Washington D.C., 1994); or the NINCDS-ADRDA criteria (see Folstein et al. *J. Psychiatr. Res.* 12:189-198 (1975)). Individuals diagnosed as having probable AD can be identified as having a mild-to-moderate form of the disease by an accepted measure of cognitive function such as the MMSE. In addition, methods that allow for evaluating different regions of the brain and estimating plaque and tangle frequencies can be used. These methods are described by Braak et al. *Acta Neuropathol* 82:239-259 (1991); Khachaturian *Arch. Neuro.* 42:1097-1105 (1985); Mirra et al. (1991) Neurology 41:479-486; and Mirra et al. *Arch Pathol Lab Med* 117:132-144 (1993). The severity of AD is generally determined by one of the initial tests provided above. For example, MMSE scores of 26-19 indicate mild AD, while scores from 18-10 indicate moderate AD.

Diagnoses of AD based on these tests are recorded as presumptive or probable, and may optionally be supported by one or more additional criteria. For example, a diagnosis of AD may be supported by evidence of a family history of AD; non-specific changes in EEG, such as increased slow-wave activity; evidence of cerebral atrophy on CT with progression documented by serial observation; associated symptoms such as depression, insomnia, incontinence, delusions, illusions, hallucinations, catastrophic verbal, emotional or physical outbursts, sexual disorders, weight loss, and/or attendant neurologic abnormalities, such as increased muscle tone, myoclonus or gait disorder, etc.

Additionally, amyloid deposits, generally associated with AD and CAA, may be detected through the use of positron emission tomography (PET) using an amyloid-specific tracer such as Pittsburgh Compound-B (PIB). See Klunk et al., *Ann. Neurol.* 55(3):306-309 (2004). Increased amyloid deposits in the frontal, parietal, temporal and occipital cortices, and in the striatum, relative to normal brain tissue, as visualized, for example by PIB, support a diagnosis of AD. Generally, a greater number and density of amyloid deposits indicates more advanced AD.

Additionally, the invention, is some embodiments, relates to identifying an individual who is experiencing a decrease in the ratio of $A\beta_{42}/A\beta_{40}$ ratio in cerebral spinal fluids (CSF) levels and treating said individual with a combination of the acetylcholine esterase inhibitor donepezil and the one or more second compounds, as described elsewhere in this application. Methods of monitoring CSF levels of $A\beta_{42}$ and $A\beta_{40}$ are known to the skilled artisan and described herein.

The invention encompasses the treatment of an individual having mild to moderate AD, to the extent that individual has AD, whether or not one or more non-AD neurodegenerative diseases or conditions are previously, concurrently or subsequently diagnosed.

The compounds and methods of the present invention are useful for individuals who have received prior medication for AD, as well as individuals who have received no prior medication for AD, and is useful for individuals currently receiving medication for AD other than a compound of the present invention, and for individuals not receiving medication for AD other than a compound of the present invention.

Individuals of any age may be treated by the methods of the invention, with the pharmaceutical compositions of the invention; however, the invention encompasses specific embodiments for treating or preventing AD in individuals between the ages of 45 and 100. In other various specific embodiments, individuals treated by the therapeutic or prophylactic methods of the invention may be from 55 to 70 years of age, 60 to 80 years of age, 55 to 65 years of age, 60 to 75 years of age, 65 to 80 years of age, 55 to 60 years of age, 60 to 65 years of age, 65 to 70 years of age, 70 to 75 years of age, 75 to 80 years of age, or 80 years old and older.

Thus, in one embodiment, the invention provides a method of treating an individual known or suspected of having AD comprising administering a therapeutically effective amount of a compound according to Formulae I-VI. In a specific embodiment, said individual is diagnosed as having mild to moderate AD. In another specific embodiment, the individual is diagnosed by a cognitive test as having mild-to-moderate AD. In yet another embodiment, said cognitive test is the Mini-Mental State Exam (MMSE). In another specific embodiment, said individual has a score in said MMSE of from 26 to 19, inclusive. In another more specific embodiment, said individual has a score in said MMSE of from 18 to 10, inclusive. In another specific embodiment, said individual has a score in said MMSE of from 26 to 10, inclusive. In another specific embodiment, said individual has a score in said MMSE of from 18 or more, 19 or more, 20 or more, 21 or more, 22 or more, 23 or more, 24 or more, or 25 or more.

In yet another embodiment, the invention provides a method of slowing cognitive decline in an individual suspected of having mild cognitive impairment (MCI) comprising administering to the individual a therapeutically effective amount of a compound according to Formulae I-VI. MCI is a clinical condition between normal aging and AD characterized by memory loss greater than expected for the particular age of the individual yet the individual does not meet the currently accepted definition for probable AD. See, e.g., Petersen et al. *Arch. Neurol.* 58:1985-1992 (2001); Petersen *Nature Rev.* 2:646-653 (2003); and Morris et al. *J Mol. Neuro.* 17:101-118 (2001). Thus, according to one aspect of the invention, an individual suspected of having or diagnosed with MCI is treated twice daily with a composition having from 400 mg to about 1200 mg per dose of a compound of the present invention, either alone, or in combination with a therapeutically effective amount of another suitable therapeutic compound, for at least 4 weeks, at least 4 months, preferably at least 8 months, and more desirably at least 1 year. Typically, patients having MCI first complain of or have a loss of memory. Preferably, a healthy individual personally associated with the patient can corroborate the memory deficit. Furthermore, general cognition is not sufficiently impaired to cause concern about more widespread cognitive disorder and although daily living activities may be affected that are not significantly impaired and the patients are not demented. Individuals having or suspected of having MCI that are not treated according to this embodiment can expect to experience a slow cognitive decline and/or progression to probable AD, mild AD, and or mild-to-moderate AD. When such individuals are treated according to the methods of the present invention, they can expect a lessening of the rate of progression of their cognitive decline, or even a stopping of their cognitive decline.

The decline in cognitive function in human patients can be characterized by cognition tests. It is preferred that the lessening in decline in cognitive function is at least 25% as compared to individuals treated with placebo, at least 40%, or at least 60%. For example, an individual treated with placebo having probably mild-to-moderate AD is expected to score approximately 5.5 points higher on the ADAS-cog test after a specified period of time (e.g., 1 year) whereas an individual treated with a composition of the invention for the same period of time will score only approximately 3.3 points higher on the ADAS-cog scale, i.e., will show 60% of the decline in cognitive function relative to untreated individuals, or 2.2 points higher i.e., will show 40% of the decline in cognitive function relative to untreated individuals, when treated for the same specified period of time.

In other embodiments, the invention provides a method of treating an individual known or suspected of having AD or MCI comprising administering an effective amount of a therapeutic compound of the present invention, wherein said individual is concurrently taking a second drug for the treatment of AD. In a further embodiment, said individual has been diagnosed as having mild to moderate AD. In a specific embodiment, said second drug being taken by that individual is an acetylcholinesterase (AChE) inhibitor. In a more specific embodiment, said AChE inhibitor is Galanthamine (galantamine, Reminyl); E2020 (Donepezil, Aricept); Physostigmine; Tacrine (tetrahydroaminoacridine, THA); Rivastigmine; Phenserine; Metrifonate (Promem); or Huperazine, or a combination of any of the foregoing. In another embodiment, said second drug is a drug other than an acetylcholinesterase inhibitor. In a preferred embodiment, the method or compositions of the invention are used in patients or individuals undergoing therapy with Aricept. The invention also encompasses methods of treating patients refractory to, or who no longer show improvement with, conventional AD therapy.

In another embodiment, the individual to be treated with a pharmaceutical composition of the present invention is concurrently taking a non-pharmaceutical substance for the treatment of AD along with a therapeutic compound of the present invention. In a specific embodiment, said non- pharmaceutical substance is an anti-oxidant. In a more specific example, said anti-oxidant is vitamin C or vitamin E. In an even more specific embodiment, said vitamin C is taken in a dose of 500-1000 mg per dose. In another even more specific embodiment, said vitamin E is taken in a dose of 400-800 IU per dose. In this regard, the invention encompasses the use of one or more such anti-oxidants as an adjunct to therapy for AD, and not primarily as a nutritional supplement.

In another embodiment, the invention provides a method of treating an individual diagnosed as having mild to moderate AD comprising administering an effective amount of a therapeutic compound of the present invention, wherein said individual has, prior to taking a therapeutic compound of the present invention, taken a second drug for the treatment of AD. In a specific embodiment, said second drug is an acetylcholinesterase (AChE) inhibitor. In a more specific embodiment, said ACE inhibitor is Galanthamine (galantamine, Reminyl); E2020 (Donepezil, Aricept); Physostigmine; Tacrine (tetrahydroaminoacridine, THA); Rivastigmine; Phenserine; Metrifonate (Promem); or Huperazine, or a combination of any of the foregoing. In another embodiment, said second drug is a drug other than an acetylcholinesterase inhibitor.

In another embodiment, said individual has, prior to taking a therapeutic compound of the present invention, taken a non-pharmaceutical substance for the treatment of AD. In a specific embodiment, said non- pharmaceutical substance is an anti-oxidant. In a more specific example, said anti-oxidant is vitamin C or vitamin E. In an even more specific embodiment, said vitamin C is taken in a dose of 500-1000 mg per dose. In another even more specific embodiment, said vitamin E is taken in a dose of 400-800 IU per dose. In this regard, the invention encompasses the use of one or more such anti-oxidants as an adjunct to therapy for AD, and not primarily as a nutritional supplement.

In yet another embodiment, the invention provides a method of slowing cognitive decline in an individual suspected of having mild cognitive impairment (MCI) comprising administering to the individual an effective amount of a therapeutic compound of the present invention. Mild cognitive impairment is a clinical condition between normal aging and AD characterized by memory loss greater than expected for the particular age of the individual yet the individual does not meet the currently accepted definition for probable AD. See, e.g., Petersen et al. *Arch. Neurol.* 58:1985-1992 (2001); Petersen *Nature Rev.* 2:646-653 (2003); and Morris et al. *J Mol. Neuro.* 17:101-118 (2001). Thus, according to this embodiment an individual suspected of having or diagnosed with MCI is treated twice daily with a composition having from 400 mg to about 800 mg of a therapeutic compound of the present invention per dose for at least 4 weeks, at least 4 months, preferably at least 8 months, and more desirably at least 1 year. Typically, patients having MCI first complain of or have a loss of memory. Preferably a healthy individual associated with the patient can corroborate the memory deficit. Furthermore, general cognition is not sufficiently impaired to cause concern about more widespread cognitive disorder and although daily living activities may be affected that are not significantly impaired and the patients are not demented. Individuals having or suspected of having MCI that are treated according to this embodiment can expect to slow cognitive decline and/or progression to probable AD.

In still another embodiment, the invention provides a method of slowing the progression of dementia in AD and DS patients comprising administering to the individual an effective amount of a therapeutic compound of the present invention. The effective amount of therapeutic compound will lead to a reduction in the level of $A\beta_{42}$ in the brains of the patients being treated, which, in turn, reduces the rate of deposition of $A\beta_{42}$ in β-amyloid plaques and a slows the progression of the dementia normally associated with the disease and disorder.

In still another embodiment, the invention provides a method of treating CAA, and reducing the likelihood of ICH, comprising administering to the individual an effective amount of a therapeutic compound of the present invention.

Administration of a pharmaceutical composition of the present invention can be via any route, and the pharmaceutical compositions of the present invention can correspond to any compositions envisioned by one of skill in the art, appropriate to the route of delivery.

Combination Therapy

The invention further provides a combination therapy strategy for treating or preventing AD, MCI, and CAA, and slowing the progression of dementia in DS. According to this aspect of the invention, an individual in need of treatment is administered a therapeutic amount of a compound of the present invention according to Formulae I-VI, and a compound selected from the group consisting of NSAIDs (non-steroidal anti-inflammatory drugs), COX-2 inhibitors (cyclooxygenase-2), β-secretase inhibitors, R-flurbiprofen, and γ-secretase inhibitors.

The methods of combination therapy provided are thought to provide a synergistic effect in reducing $A\beta_{42}$ levels and are thought to be especially effective for preventing AD and MCI, and slowing the progression of dementia in DS. The treatment regimens used in the combination therapy can involve administration of pharmaceutical compositions comprising a combination of active ingredients, or the concomitant administration of separate compositions, each comprising at least one active ingredient. Furthermore, the administration of the active ingredients can be performed at different times and/or via different routes. For example, a composition comprising at least one active ingredient can be administered in the morning, and a composition comprising at least one different active ingredient can be administered in the evening. Another example would involve the administration of a composition having at least one active ingredient orally while the second composition having at least on other active ingredient is administered intravenously.

In addition to the advantages described above, while not wishing to be bound by theory, it is believed that therapeutic compounds of Formulae I-VI are capable of slowing the rate of death of neurons. Accordingly, it is also believed that the compounds of Formulae I-VI act in vivo to treat and/or prevent AD and MCI, and slow the progression of dementia in DS, by slowing the rate of death of neurons that is present, or would be present, in the absence of such treatment.

Methods of Synthesis

In accordance with another aspect of the present invention, a synthesis method is provided, comprising providing a compound having a Formula (VII)

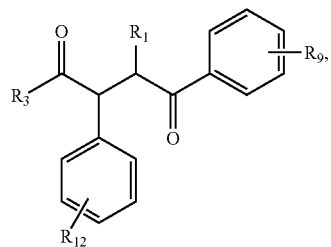

(VII)

and a compound having a Formula VIII

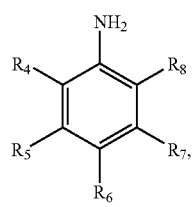

(VIII)

and reacting the two compounds under conditions to form a compound of Formula III, wherein $R_1$, $R_3$, $R_4$, $R_5$, $R_6$, $R_7$, $R_8$, $R_9$, and $R_{12}$ are as defined above. Detailed examples and conditions used, are provided in Examples 1-3 below.

In another aspect of the present invention, a synthesis method is provided for making a compound having Formula V, comprising providing a ketone compound having a Formula IX,

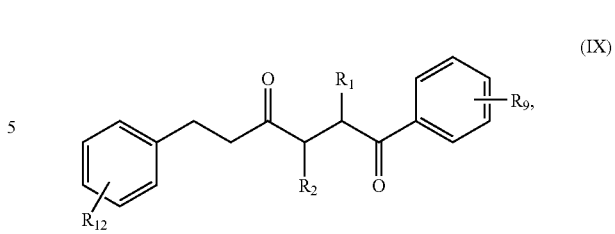

(IX)

and an aniline compound having a Formula VIII

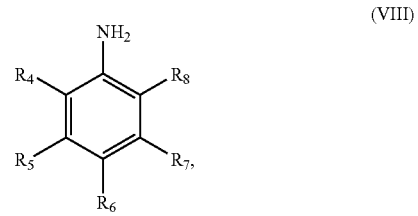

(VIII)

and reacting the two compounds under conditions to form a compound of Formula V, wherein $R_1$, $R_3$, $R_4$, $R_5$, $R_6$, $R_7$, $R_8$, $R_9$, and $R_{12}$ are as defined above. Detailed examples and conditions used, are provided in Examples 1-3 below.

EXAMPLES

Example 1

Synthesis of Representative Ketone/Aldehyde Starting Material Via Sila-Stetter Reaction

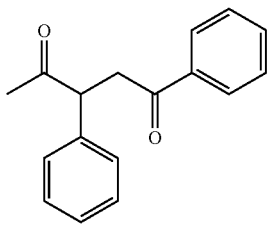

1,3-Diphenyl-pentane-1,4-dione: 1-Trimethylsilanyl-ethanone (1.15 mL; 8.02 mmol) followed by DBU (0.18 mL; 1.2 mmol) were added to a suspension of 3-ethyl-5-(2-hydroxyethyl)-4-methylthiazolium bromide (304 mg; 1.21 mmol) in dry THF (5 mL). The mixture was heated at 70° C. for 4 min, cooled near rt, then chalcone (833 mg; 4.00 mmol) and 2-propanol (1.22 mL; 15.9 mmol) were added. The reaction was degassed and reacted under nitrogen at 70° C. After 24 h, the reaction was concentrated on a rotary evaporator. Ethyl acetate (25 mL) was added and this washed with H2O (3×3 mL) and satd NaCl (2×3 mL). The organic portion was dried (MgSO4) and filtered through silica with an EtOAc wash. Crude product was adsorbed onto silica (2 g) then purified by MPLC (40 g of silica using a 0→20% EtOAc in hexanes gradient). Pure product was obtained as a clear, colorless viscous liquid (980 mg; 97%). 1H NMR (CDCl3) d 7.98-7.94 (m, 2H), 7.56 (m, 1H), 7.47-7.42 (m, 2H), 7.39-

7.27 (m, 5H), 4.44 (dd, J=3.6, 10.0 Hz, 1H), 4.02 (dd, J=10.0, 18.0 Hz, 1H), 3.14 (dd, J=3.6, 18.0 Hz, 1H); GC-MS 252 ([M]+).

Example 2

Representative Chalcone
((E)-1,3-diphenyl-propenone) Formation

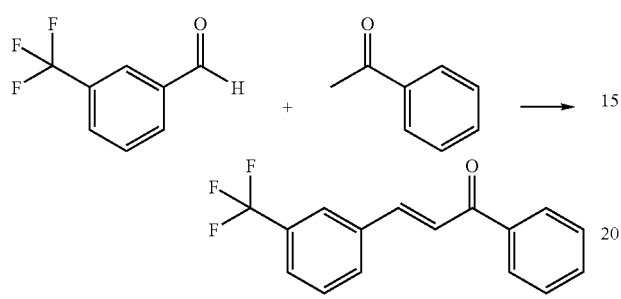

(E)-1-Phenyl-3-(3-trifluoromethyl-phenyl)-propenone: Aq. sodium hydroxide (1 M; 2.0 mL; 2.0 mmol) was added to a soln of 3-trifluoromethyl-benzaldehyde (592 mg; 3.40 mmol) and 1-phenyl-ethanone (400 µL; 3.42 mmol) in absolute ethanol (10 mL). After 3 h, the ppt was collected and washed with 5:1 EtOH:H2O, then dried in vacuo affording a cream-colored solid (652 mg; 69%). 1H NMR (CDCl3) δ 8.05 (m, 2H), 7.90 (m, 1H), 7.86-7.79 (m, 2H), 7.70-7.50 (m, 6H).

Example 3

Representative Stetter Reaction

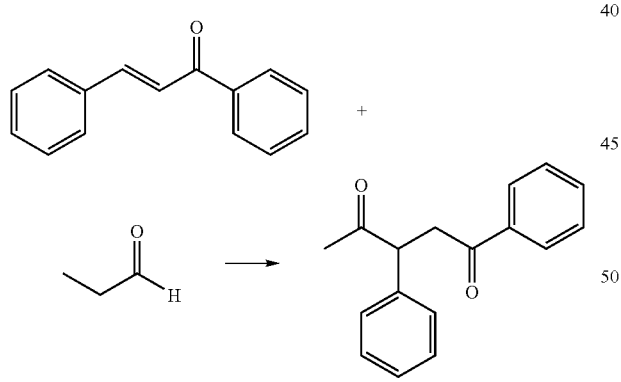

1,3-Diphenyl-hexane-1,4-dione: A mixture of (E)-1,3-diphenyl-propenone (1.042 g; 5.00 mmol), propionaldehyde (0.40 mL; 5.6 mmol), 3-ethyl-5-(2-hydroxyethyl)-4-methylthiazolium bromide (126 mg; 0.500 mmol) and triethylamine (0.42 mL; 3.0 mmol) in absolute ethanol (3.0 mL) was degassed then heated at 70° C. for 25 h. After an additional 1.5 h at 80° C., the organic volatiles were removed on a rotary evaporator. EtOAc (25 mL) was added and the solution washed with water (3×5 mL) and satd NaCl (2×5 mL); then dried (MgSO4), filtered through silica and washed through with EtOAc. Crude product was adsorbed onto silica (2.0 g) then purified by MPLC (40 g of silica using a 0→20% EtOAc in hexanes gradient). Pure product was obtained as a clear, pale tan liquid (760 mg; 57%). 1H NMR (CDCl3) δ 7.96 (m, 2H), 7.56 (m, 1H), 7.45 (m, 2H), 7.38-7.26 (m, 5H), 4.43 (dd, J=3.4, 10.2 Hz, 1H), 4.05 (dd, J=10.4, 18.0 Hz, 1H), 3.14 (dd, J=3.8, 18.2 Hz, 1H), 2.65 (m, 1H), 2.53 (m, 1H), 1.02 (t(app), J=7.2 Hz, 3H).

Example 4

Representative Pyrrole Formation—Synthesis of 4-[4-(2-Methyl-3,5-diphenyl-pyrrol-1-yl)-phenyl]-butyric acid

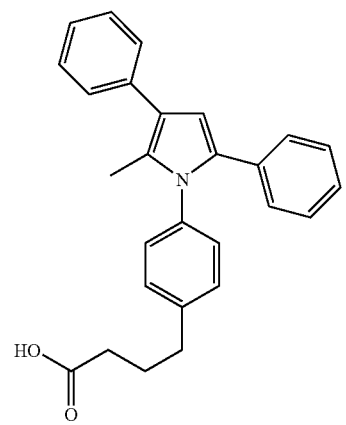

4-[4-(2-Methyl-3,5-diphenyl-pyrrol-1-yl)-phenyl]-butyric acid: A soln of 1,3-diphenyl-pentane-1,4-dione (104 mg; 0.412 mmol) and 4-(4-amino-phenyl)-butyric acid (89 mg; 0.497 mmol) in acetic acid (2 mL) was heated at 120° C. After 6 h, the reaction was concentrated on a rotary evaporator. Ethyl acetate (5 mL) was added and this washed with H2O (1×2 mL) and satd NaCl (1×3 mL). The organic portion was dried (MgSO4) and filtered through silica with an EtOAc wash. Crude product was adsorbed onto silica (0.3 g) then purified by MPLC (12 g of silica using a 0→50% EtOAc in hexanes gradient). Pure product was obtained as a white solid (115 mg; 71%). 1H NMR (CDCl3) d 7.54-7.49 (m, 2H), 7.44-7.38 (m, 2H), 7.26-7.07 (m, 10H), 6.56 (s, 1H), 2.72 (t, J=7.6 Hz, 2H), 2.40 (t, J=7.4 Hz, 2H), 2.25 (s, 3H), 2.00 (m, 2H); LC-MS (ESI−) 394 ([M−H]−).

Example 5

Additional Transformations

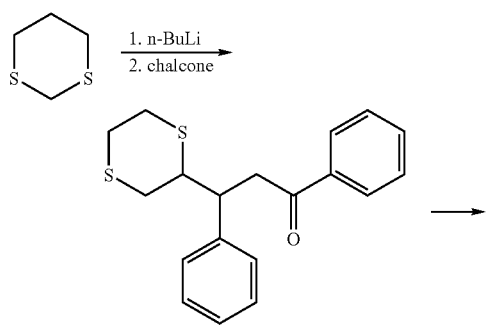

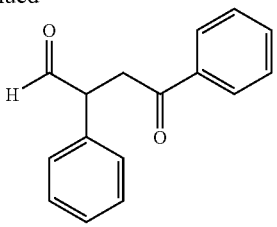

3-[1,3]Dithian-2-yl-1,3-diphenyl-propan-1-one: n-BuLi (2.5 M in hexanes; 7.50 mL; 18.8 mmol) was added over 2 min to [1,3]dithiane (1.876 g; 15.6 mmol) in dry THF (20 mL) at −78° C. The rxn warmed to −20° C. over 1.5 h then was cooled to −78° C. and chalcone (3.239 g; 15.6 mmol) was added in one portion. After 6 h the rxn was quenched with satd NH₄Cl. Aq/organic extractions were followed by partial purification by MPLC (silica eluting with a dichloromethane in hexanes gradient) affording a mixture of [1,2] and [1,4] addition products. $^1$H NMR (CDCl₃; partial spectrum for major product) δ 4.38 (d, J=6.8 Hz, 1H), 3.50 (dd, J=8.2, 17.4 Hz, 1H).

4—Oxo-2,4-diphenyl-butyraldehyde: CaCO₃ (483 mg; 4.83 mmol) followed by iodomethane (3.0 mL; 48 mmol) was added to a suspension of the above dithiane mixture (316 mg) in 8:1 (v:v) CH₃CN:H₂O (18 mL). After 21 h at rt, the rxn was concd on a rotary evaporator; partitioned/extracted with aq/EtOAc; dried (MgSO₄) and finally filtered through a plug of silica and washed through with EtOAc yielding a pale yellow liquid upon concentration. $^1$H NMR (CDCl₃) δ 9.81 (d, J=0.4 Hz, 1H), 7.99 (m, 2H), 7.60-7.24 (m, 8H), 4.46 (dd, J=4.8, 8.4 Hz, 1H), 3.96 (dd, J=8.8, 18.0 Hz, 1H), 3.23 (ddd, J=0.6, 5.0, 18.0 Hz, 1H) ; GC-MS 238 ([M]$^+$).

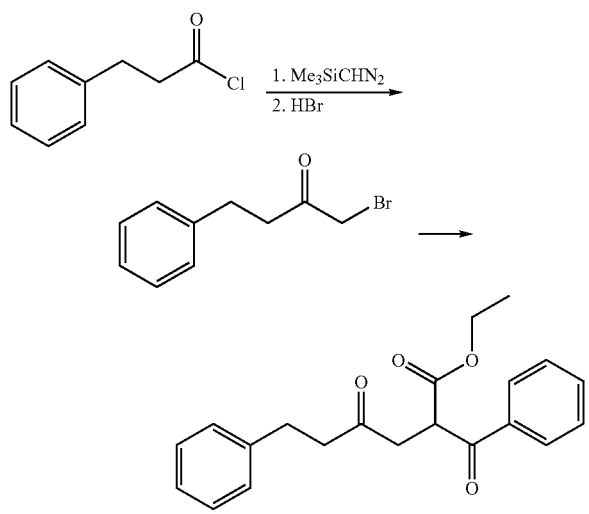

1-Bromo-4-phenyl-butan-2-one: (i) A soln of 3-phenyl-propionyl chloride (2.0 mL; 13.5 mmol) in dry THF (50 mL) was added over 6 min to a 0° C. soln of diazomethyl-trimethyl-silane (2.0 M in hexanes; 15 mL; 30 mmol) in dry THF (50 mL). After 3 h, the rxn was concd to a liquid. (ii) Aq. HBr (48%; ca. 2.5 eq) was added in one portion to a soln of this crude material in AcOH (30 mL) at 0° C. After 10 min the rxn was concd. EtOAc (50 mL) was added and the soln washed with water (2×15 mL), satd NaHCO3 (3×15 mL), water (1×15 mL) and satd NaCl (2×15 mL). After drying over MgSO4, filtering through a pad of silica with an EtOAc wash and concd to an oil, the crude material was purified by MPLC (SiO2 with a 0-->20% EtOAc in hexanes gradient) yielding bromomethyl ketone as an off-white solid (1.977 g; 65%). 1H NMR (CDCl3) δ 7.37-7.18 (m, 5H), 3.85 (s, 2H), 3.01-2.94 (m, 4H); GC-MS 226/228 ([M]+).

2-Benzoyl-4-oxo-6-phenyl-hexanoic acid ethyl ester: Neat 3-oxo-3-phenyl-propionic acid ethyl ester (95%; 0.80 mL; 4.4 mmol) was added over 1.5 min to a soln of KO-t-Bu (1.0 M in THF; 4.40 mL; 4.4 mmol) in THF (4.4 mL) at 0° C. After 20 min, the above solid bromomethyl ketone (910 mg; 4.0 mmol) was added in one portion. After an additional 2 h, the rxn was quenched with aq. citric acid. The organic volatiles were removed on a rotary evaporator then the product extracted into EtOAc (25 mL). The soln was washed with water (2×8 mL), satd NaCl (1×8 mL), dried over MgSO4, filtered through a plug of silica with an EtOAc wash and concd. The product was purified by MPLC (silica; 0-->35% EtOAc in hexanes gradient) yielding a clear, colorless liquid (1.199 g; 97%). 1H NMR (CDCl3) δ 8.02 (m, 2H), 7.60 (m, 1H), 7.49 (m, 2H), 7.28 (m, 2H), 7.22-7.15 (m, 3H), 4.93 (dd, J=6.4, 7.6 Hz, 1H), 4.13 (q, J=7.2 Hz, 2H), 3.19 (dd, J=7.6, 18.4 Hz, 1H), 3.12 (dd, J=6.4, 18.0 Hz, 1H), 2.94-2.82 (m, 4H), 1.15 (t, J=7.0 Hz, 3H).

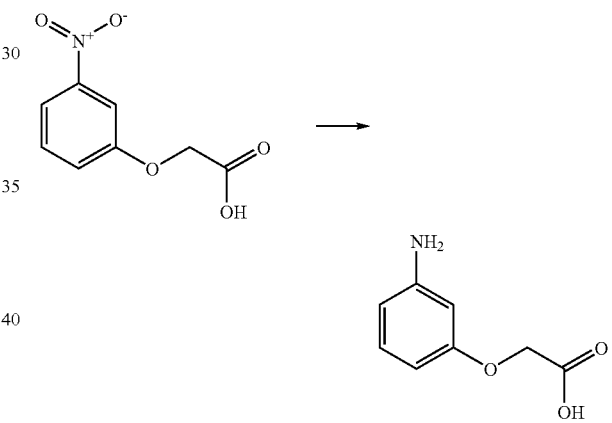

(3-Amino-phenoxy)-acetic acid: (3—Nitro-phenoxy)-acetic acid (1.978 g; 10.0 mmol) was reduced by catalytic hydrogenation (10% Pd—C; 45 psi H2) in AcOH-EtOH-MeOH then filtered through diatomaceous earth and concd yielding the title aniline. LC-MS 168 ([M+H]+).

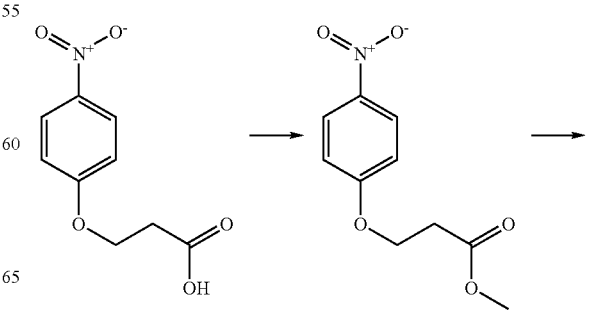

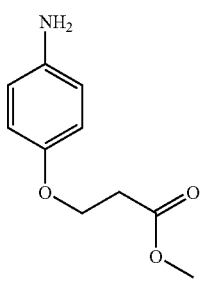

3-(4-Nitro-phenoxy)-propionic acid methyl ester: Neat AcCl (0.27 mL; 3.8 mmol) was added to a suspension of 3-(4-nitro-phenoxy)-propionic acid (1.591 g; 7.53 mmol) in dry MeOH (8.0 mL). A soln formed followed by a ppt. After sitting at 4° C. overnight, product was collected by filtration as a white microcrystalline solid (1.316 g; 78%). The mother liquor contained pure product by HPLC. LC-MS 226 ([M+H]+).

3-(4-Amino-phenoxy)-propionic acid methyl ester: The above nitroarene (1.597 g; 7.1 mmol) was reduced by catalytic hydrogenation (10% Pd—C (50 mg) in 10:1 abs. EtOH: AcOH (22 mL) under 1 atm of H2). After 16 h the rxn was concd. EtOAc was added and the rxn filtered through a pad of silica, then washed with satd NaHCO3, 50% satd NaCl and satd NaCl. The soln was dried over MgSO4, filtered through silica with an EtOAc wash and concd to a maroon liquid which solidified upon standing (1.316 g; 95%). LC-MS 196 ([M+H]+).

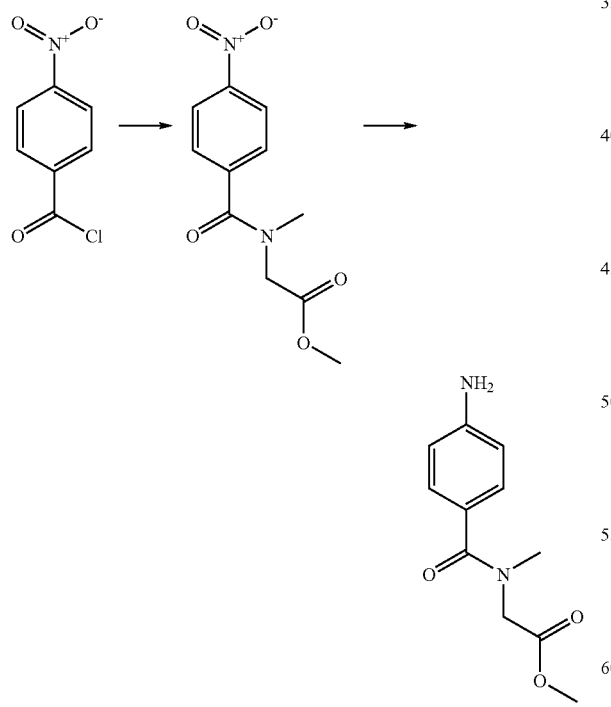

[Methyl-(4-nitro-benzoyl)-amino]-acetic acid methyl ester: 4-Nitro-benzoyl chloride (1.396 g; 7.52 mmol), methylamino-acetic acid methyl ester hydrochloride (1.264 g; 9.06 mmol) and triethyl-amine (2.40 mL; 17.2 mmol) were reacted in DCM (35 mL). After 2 days the rxn was washed with water (1×10 mL), 1 M HCl (2×10 mL), water (1×10 mL) and satd NaHCO3 (2×10 mL). After drying over MgSO4, filtration through silica with a 10:1 DCM:i-PrOH wash and concd, the product was purified by MPLC (silica; 0-->10% i-PrOH in DCM gradient) yielding a pale yellow-orange solid (1.394 g; 73%) as a mix of rotamers. 1H NMR (CDCl3; major rotamer) δ 8.31 (m, 2H), 7.66 (m, 2H), 4.31 (s, 2H), 3.82 (s, 3H), 3.03 (s, 3H).

[(4-Amino-benzoyl)-methyl-amino]-acetic acid methyl ester: The above nitroarene (136 mg; 0.539 mmol) was reduced by catalytic hydrogenation (10% Pd—C in AcOH (2 mL) under 1 atm of H2). The rxn was monitored by HPLC. After 25 h the rxn was filtered (0.45 μm) then used as is.

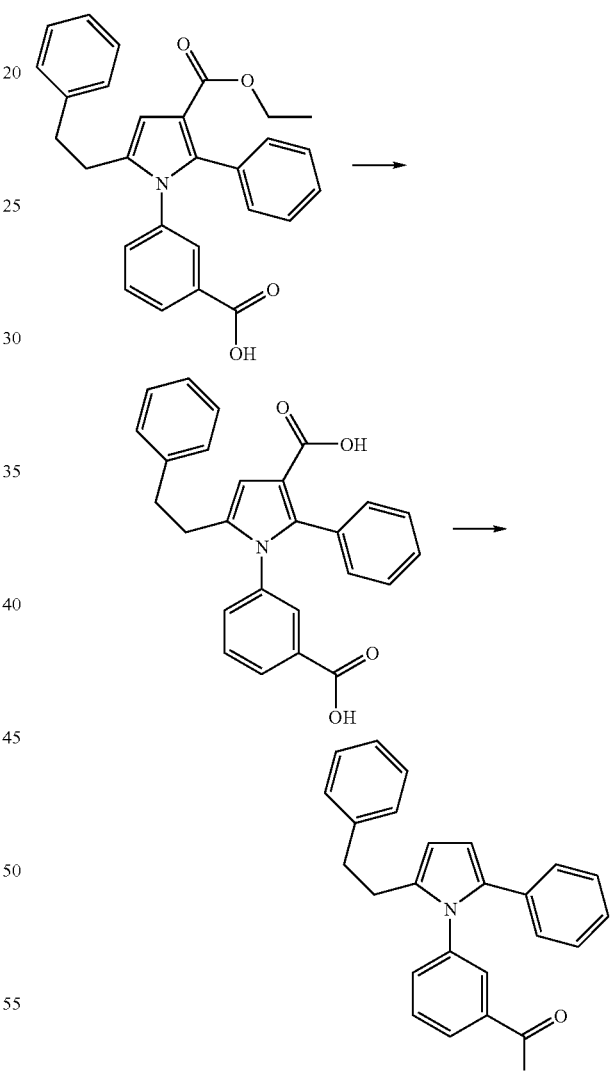

1-(3-Carboxy-phenyl)-5-phenethyl-2-phenyl-1H-pyrrole-3-carboxylic acid: Solid NaOH (90 mg; 2.3 mmol) was added to a soln of 1-(3-carboxy-phenyl)-5-phenethyl-2-phenyl-1H-pyrrole-3-carboxylic acid ethyl ester (157 mg; 0.357 mmol) in ethylene glycol (2.0 mL) at 160° C. After 1.6 h, the rxn was cooled then quenched with 1 M HCl (5 mL). The product was extracted into EtOAc (3×3 mL) and this soln was washed with water (3×3 mL) and satd NaCl (2×3 mL). After drying over MgSO4, filtration through silica with an EtOAc wash and concd, crude product was obtained. LC-MS 412 ([M+H]+).

3-(2-Phenethyl-5-phenyl-pyrrol-1-yl)-benzoic acid: A soln of the above diacid in TFA (5 mL) was heated in a microwave at 100° C. for 180 s. The rxn was concd. EtOAc (8 mL) was added and this washed with water (2×2 mL) and satd NaCl (2×2 mL); then dried over MgSO4, filtered through silica with an EtOAc wash, concd then purified by MPLC (silica; 0-->60% EtOAc in hexanes gradient) yielding product as an off-white solid (21 mg). 1H NMR (CDCl3+3 drops CD3OD) δ 8.03 (m, 1H), 7.93 (m, 1H), 7.40 (m, 1H), 7.26-7.01 (m, 11H), 6.39 (d, J=3.2 Hz, 1H), 6.19 (d, J=3.6 Hz, 1H), 2.83-2.72 (m, 4H).

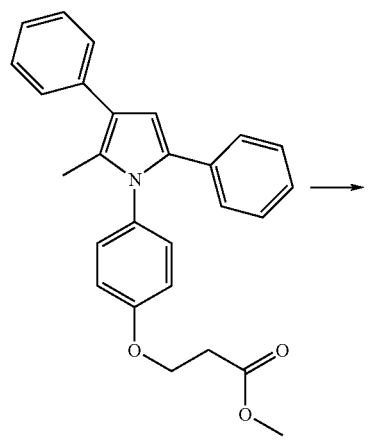

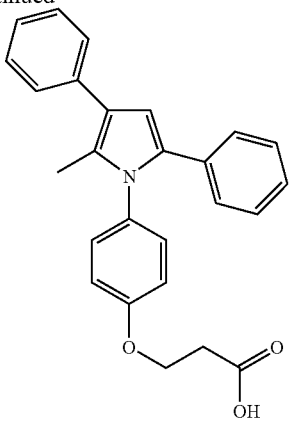

3-[4-(2-Methyl-3,5-diphenyl-pyrrol-1-yl)-phenoxy]-propionic acid: A mixture of 3-[4-(2-methyl-3,5-diphenyl-pyrrol-1-yl)-phenoxy]-propionic acid methyl ester (51 mg; 0.12 mmol) and LiOH (5.4 mg; 0.23 mmol) in THF (1.0 mL)/MeOH (0.5 mL)/H2O (0.4 mL) was heated at 40° C. for 4 h then quenched with aq. citric acid. Product was extracted into EtOAc then washed with water and satd NaCl; then dried over MgSO4, filtered through silica with an EtOAc wash, concd then purified by MPLC (silica; 0-->100% EtOAc in hexanes gradient) yielding product as a grey solid (9 mg). 1H NMR (CDCl3) δ 7.53-7.48 (m, 2H), 7.41 (m, 2H), 7.24 (m, 1H), 7.20-7.08 (m, 7H), 6.91 (m, 2H), 6.55 (s, 1H), 4.27 (t, J=6.4 Hz, 2H), 2.89 (t, J=6.2 Hz, 2H), 2.23 (s, 3H).

Example 6

Synthesis of Selected Example Compounds

Using the general reaction schemes and transformation reactions presented in the Examples above, compounds of the present invention can be synthesized from the starting materials identified in Table 2, below.

TABLE 2

Starting Materials and Example Compounds Synthesized

| Cmpd. No. | Compound Structure | Ketone/Aldehyde starting material | Aniline | 1H NMR, δ | MS |
|---|---|---|---|---|---|
| 1 | 2-methyl-3,5-diphenyl-1-(4-(3-carboxypropyl)phenyl)pyrrole | 1,3-diphenyl-2-acetyl-propan-1-one | 4-(3-aminophenyl)butanoic acid | CDCl3: 7.54-7.49 (m, 2H), 7.44-7.38 (m, 2H), 7.26-7.07 (m, 10H), 6.56 (s, 1H), 2.72 (t, J = 7.6 Hz, 2H), 2.40 (t, J = 7.4 Hz, 2H), 2.25 (s, 3H), 2.00 (m, 2H) | 394 ([M − H]−) |
| 2 | 2-methyl-3,5-diphenyl-1-(3-carboxyphenyl)pyrrole | 1,3-diphenyl-2-acetyl-propan-1-one | 3-aminobenzoic acid | DMSO-d6: 7.97 (m, 1H), 7.70 (m, 1H), 7.64-7.55 (m, 2H), 7.53-7.48 (m, 2H), 7.45-7.40 (m, 2H), 7.27-7.16 (m, 3H), 7.14-7.06 (m, 3H), 6.63 (s, 1H) | 352 ([M − H]−) |

TABLE 2-continued

Starting Materials and Example Compounds Synthesized

| Cmpd. No. | Compound Structure | Ketone/Aldehyde starting material | Aniline | 1H NMR, δ | MS |
|---|---|---|---|---|---|
| 3 | (2,5-diphenyl-2-methylpyrrol-1-yl)-chloro-benzoic acid structure | 1,4-diphenyl-pentane-1,3-dione | 5-amino-2-chlorobenzoic acid | CDCl3: 7.96 (d, J = 2.4 Hz, 1H), 7.52-7.46 (m, 3H), 7.45-7.40 (m, 2H), 7.30-7.09 (m, 7H), 6.56 (s, 1H), 2.27 (s, 3H) | 388 ([M + H]+) |
| 4 | (2,5-diphenyl-2-methylpyrrol-1-yl)-methoxy-benzoic acid structure | 1,4-diphenyl-pentane-1,3-dione | 3-amino-4-methoxybenzoic acid | CDCl3: 8.12 (dd, J = 2.2, 8.6 Hz, 1H), 7.91 (d, J = 2.4 Hz, 1H), 7.55-7.50 (m, 2H), 7.44-7.38 (m, 2H), 7.27-7.21 (m, 1H), 7.18-7.07 (m, 5H), 7.02 (d, J = 8.8 Hz, 1H), 6.57 (s, 1H), 3.77 (s, 3H), 2.19 (s, 3H) | 384 ([M + H]+) |

TABLE 2-continued

Starting Materials and Example Compounds Synthesized

| Cmpd. No. | Compound Structure | Ketone/Aldehyde starting material | Aniline | 1H NMR, δ | MS |
|---|---|---|---|---|---|
| 5 | (2,4-diphenyl-5-methyl-pyrrol-1-yl)phenyl propanoic acid structure | 1,4-diphenyl-2-methyl-pentane-1,4-dione | 3-(3-aminophenyl)propanoic acid | CDCl3: 7.53-7.49 (m, 2H), 7.44-7.38 (m, 2H), 7.32 (m, 1H), 7.28-7.06 (m, 8H), 7.03 (m, 1H), 6.56 (s, 1H), 2.92 (t, J = 7.4 Hz, 2H), 2.56 (t, J = 7.6 Hz, 2H), 2.25 (s, 3H) | 380 ([M − H]−) |
| 6 | 3-(2,4-diphenylpyrrol-1-yl)benzoic acid structure | 4-oxo-2,4-diphenylbutanal | 3-aminobenzoic acid | CDCl3: 8.07 (m, 1H), 8.02 (m, 1H), 7.61 (m, 2H), 7.43-7.16 (m, 11H), 6.77 (d, J = 1.6 Hz, 1H) | 340 ([M + H]+) |

TABLE 2-continued

Starting Materials and Example Compounds Synthesized

| Cmpd. No. | Compound Structure | Ketone/Aldehyde starting material | Aniline | 1H NMR, δ | MS |
|---|---|---|---|---|---|
| 7 | (2,4-diphenylpyrrol-1-yl)phenyl butanoic acid structure | 2-phenyl-4-oxo-4-phenylbutanal | 4-aminophenyl propanoic acid (NH₂-C₆H₄-CH₂CH₂CH₂-COOH) | CDCl3: 7.62-7.57 (m, 2H), 7.40-7.34 (m, 2H), 7.25-7.11 (m, 11H), 6.74 (d, J = 2.0 Hz, 1H), 2.69 (t, J = 7.6 Hz, 2H), 2.39 (t, J = 7.2 Hz, 2H), 1.98 (m, 2H) | 382.17974 (TOF; [M + H]+) |
| 8 | 3-[2-methyl-5-phenyl-3-(3-trifluoromethylphenyl)pyrrol-1-yl]benzoic acid structure | 3-(3-trifluoromethylphenyl)-1-phenyl-pentane-1,4-dione | 3-aminobenzoic acid | CDCl3: 8.11 (m, 1H), 8.04 (m, 1H), 7.75 (m, 1H), 7.67 (m, 1H), 7.56-7.47 (m, 3H), 7.41 (m, 1H), 7.22-7.08 (m, 5H), 6.58 (s, 1H), 2.26 (s, 3H) | 420 ([M − H]−) |

TABLE 2-continued

Starting Materials and Example Compounds Synthesized

| Cmpd. No. | Compound Structure | Ketone/Aldehyde starting material | Aniline | 1H NMR, δ | MS |
|---|---|---|---|---|---|
| 9 | 3-[3-[2-methyl-5-phenyl-4-[3-(trifluoromethyl)phenyl]pyrrol-1-yl]phenyl]propanoic acid | 1-phenyl-3-[3-(trifluoromethyl)phenyl]-pentane-1,4-dione | 3-aminophenylpropanoic acid (NH₂-C₆H₄-CH₂CH₂COOH, meta) | CDCl3: 7.75 (m, 1H), 7.67 (m, 1H), 7.54-7.46 (m, 2H), 7.33 (m, 1H), 7.22-7.02 (m, 8H), 6.56 (s, 1H), 2.92 (t, J = 7.4 Hz, 2H), 2.56 (t, J = 7.4 Hz, 2H), 2.24 (s, 3H) | 450.16704 (TOF; [M + H]+) |
| 10 | 4-[4-[2-methyl-5-phenyl-4-[3-(trifluoromethyl)phenyl]pyrrol-1-yl]phenyl]butanoic acid | 1-phenyl-3-[3-(trifluoromethyl)phenyl]-pentane-1,4-dione | 4-aminophenylbutanoic acid (NH₂-C₆H₄-CH₂CH₂CH₂COOH, para) | CDCl3: 7.75 (m, 1H), 7.67 (m, 1H), 7.54-7.46 (m, 2H), 7.24-7.08 (m, 9H), 6.56 (s, 1H), 2.72 (t, J = 7.6 Hz, 2H), 2.40 (t, J = 7.4 Hz, 2H), 2.24 (s, 3H), 2.00 (m, 2H) | 462 ([M − H]−) |

TABLE 2-continued

Starting Materials and Example Compounds Synthesized

| Cmpd. No. | Compound Structure | Ketone/Aldehyde starting material | Aniline | 1H NMR, δ | MS |
|---|---|---|---|---|---|
| 11 | (2,5-diphenyl-3-phenyl-N-aryl-pyrrole with ethyl and benzoic acid) | 1,2-diphenyl-pentane-1,4-dione | 3-aminobenzoic acid | CDCl3: 8.14-8.08 (m, 2H), 7.53-7.38 (m, 6H), 7.30-7.24 (m, 1H), 7.19-7.06 (m, 5H), 6.55 (s, 1H), 2.71 (q, J = 7.2 Hz, 2H), 0.92 (t, J = 7.6 Hz, 3H) | 368.16533 (TOF; [M + H]+) |
| 12 | (2,5-diphenyl-3-phenyl-N-aryl-pyrrole with ethyl and phenylpropanoic acid) | 1,2-diphenyl-pentane-1,4-dione | 3-(3-aminophenyl)propanoic acid | CDCl3: 7.53-7.48 (m, 2H), 7.43-7.37 (m, 2H), 7.32 (m, 1H), 7.28-7.18 (m, 2H), 7.16-7.04 (m, 7H), 6.53 (s, 1H), 2.92 (t, J = 7.6 Hz, 2H), 2.71 (q, J = 7.5 Hz, 2H), 2.57 (t, J = 7.6 Hz, 2H), 0.90 (t, J = 7.6 Hz, 3H) | 396.19522 (TOF; [M + H]+) |

TABLE 2-continued

Starting Materials and Example Compounds Synthesized

| Cmpd. No. | Compound Structure | Ketone/Aldehyde starting material | Aniline | 1H NMR, δ | MS |
|---|---|---|---|---|---|
| 13 | (pyrrole with 2,5-diphenyl, 3-phenyl, 2-ethyl substituents; N-linked to 4-(3-carboxypropyl)phenyl) | 1,3-diphenyl-2-(propanoyl)propan-1-one derivative | 4-(3-aminophenyl)butanoic acid (4-aminophenylpropyl-COOH) | CDCl3: 7.53-7.49 (m, 2H), 7.43-7.37 (m, 2H), 7.28-7.06 (m, 10H), 6.54 (s, 1H), 2.76-2.66 (m, 4H), 2.39 (t, J = 7.4 Hz, 2H), 2.00 (m, 2H), 0.92 (t, J = 7.4 Hz, 3H) | 432.19283 (TOF; [M + Na]+) |
| 14 | (pyrrole with 5-(4-trifluoromethylphenyl), 3-phenyl, 2-methyl; N-linked to 3-carboxyphenyl) | 1-(4-trifluoromethylphenyl)-3-phenyl-4-oxopentan-1-one | 3-aminobenzoic acid | CDCl3: 8.14 (m, 1H), 8.05 (m, 1H), 7.56-7.38 (m, 8H), 7.31-7.25 (m, 1H), 7.20-7.15 (m, 2H), 6.65 (s, 1H), 2.26 (s, 3H) | 422.13646 (TOF; [M + H]+) |

TABLE 2-continued

Starting Materials and Example Compounds Synthesized

| Cmpd. No. | Compound Structure | Ketone/Aldehyde starting material | Aniline | 1H NMR, δ | MS |
|---|---|---|---|---|---|
| 15 | 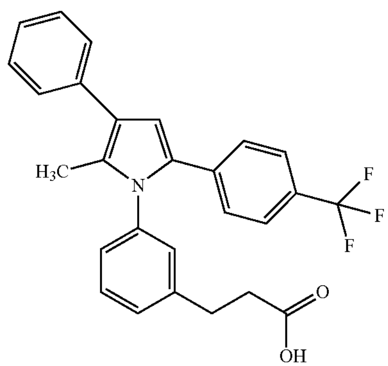 | | | CDCl3: 7.52-7.47 (m, 2H), 7.44-7.31 (m, 5H), 7.29-7.20 (m, 2H), 7.18-7.14 (m, 2H), 7.09-7.07 (m, 2H), 6.64 (s, 1H), 2.95 (t, J = 7.4 Hz, 2H), 2.60 (t, J = 7.4 Hz, 2H), 2.24 (s, 3H) | 450.16678 (TOF; [M + H]+) |
| 16 | 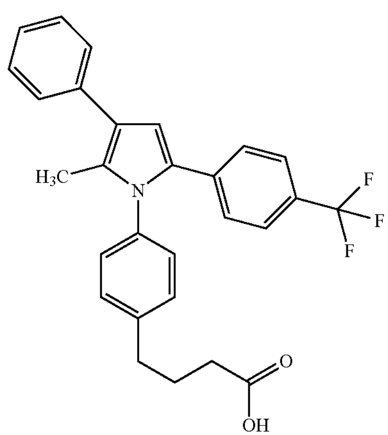 | | | CDCl3: 7.52-7.47 (m, 2H), 7.45-7.36 (m, 4H), 7.29-7.21 (m, 3H), 7.19-7.13 (m, 4H), 6.64 (s, 1H), 2.74 (t, J = 8.0 Hz, 2H), 2.41 (t, J = 7.6 Hz, 2H), 2.24 (s, 3H), 2.02 (m, 2H) | 486.16389 (TOF; [M + Na]+) |

TABLE 2-continued

Starting Materials and Example Compounds Synthesized

| Cmpd. No. | Compound Structure | Ketone/Aldehyde starting material | Aniline | 1H NMR, δ | MS |
|---|---|---|---|---|---|
| 17 | [structure: 2-(3,4-dichlorophenyl)-5-methyl-4-phenyl-pyrrole N-substituted with 3-carboxyphenyl] | [structure: 1-(3,4-dichlorophenyl)-2-phenyl-pentane-1,4-dione] | [structure: 3-aminobenzoic acid] | CDCl3: 8.14 (m, 1H), 8.01 (m, 1H), 7.55 (m, 1H), 7.50–7.40 (m, 5H), 7.31–7.25 (m, 2H), 7.18 (d, J = 8.4 Hz, 1H), 6.79 (dd, J = 2.4, 8.4 Hz, 1H), 6.59 (s, 1H), 2.24 (s, 3H) | 422.07034 (TOF; [M + H]+) |
| 18 | [structure: 2-(3,4-dichlorophenyl)-5-methyl-4-phenyl-pyrrole N-substituted with 3-(2-carboxyethyl)phenyl] | [structure: 1-(3,4-dichlorophenyl)-2-phenyl-pentane-1,4-dione] | [structure: 3-(3-aminophenyl)propanoic acid] | CDCl3: 7.50–7.46 (m, 2H), 7.44–7.32 (m, 3H), 7.28–7.22 (m, 2H), 7.20–7.15 (m, 2H), 7.10–7.04 (m, 2H), 6.81 (dd, J = 2.0, 8.4 Hz, 1H), 6.58 (s, 1H), 2.97 (t, J = 7.6 Hz, 2H), 2.64 (t, J = 7.4 Hz, 2H), 2.22 (s, 3H) | 450.10227 (TOF; [M + H]+) |

TABLE 2-continued

Starting Materials and Example Compounds Synthesized

| Cmpd. No. | Compound Structure | Ketone/Aldehyde starting material | Aniline | 1H NMR, δ | MS |
|---|---|---|---|---|---|
| 19 | (3,4-dichlorophenyl, phenyl, methyl pyrrole with N-phenyl-propanoic acid) | 1-(3,4-dichlorophenyl)-4-phenyl-pentane-1,4-dione | 4-(3-aminophenyl)propyl...  (4-aminophenyl propanoic acid derivative) | CDCl3: 7.52-7.46 (m, 2H), 7.44-7.38 (m, 2H), 7.28-7.23 (m, 3H), 7.20-7.11 (m, 4H), 6.86 (dd, J = 2.0, 8.4 Hz, 1H), 6.58 (s, 1H), 2.75 (t, J = 7.6 Hz, 2H), 2.41 (t, J = 7.6 Hz, 2H), 2.24 (s, 3H), 2.02 (m, 2H) | 462 ([M − H]−) |
| 20 | (CO2Et, diphenyl pyrrole with N-phenyl-benzoic acid, phenethyl) | ethyl 2-(3-oxo-5-phenylpentanoyl)-3-oxo-3-phenylpropanoate | 3-aminobenzoic acid | CDCl3: 7.99 (m, 1H), 7.79 (m, 1H), 7.35 (m, 1H), 7.26-7.20 (m, 2H), 7.20-7.11 (m, 7H), 7.04 (m, 2H), 6.69 (m, 1H), 4.17 (q, J = 7.2 Hz, 2H), 2.86 (t, J = 7.8 Hz, 2H), 2.69 (m, 2H), 1.17 (t, J = 7.2 Hz, 3H) | 440 ([M + H]+) |

TABLE 2-continued

Starting Materials and Example Compounds Synthesized

| Cmpd. No. | Compound Structure | Ketone/Aldehyde starting material | Aniline | 1H NMR, δ | MS |
|---|---|---|---|---|---|
| 21 | 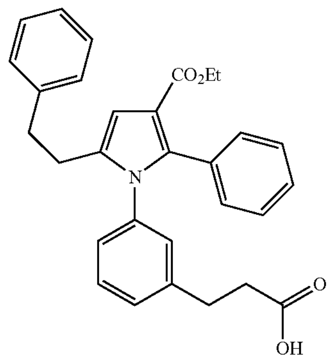 | | | CDCl3: 7.26-7.10 (m, 9H), 7.08 (m, 1H), 7.03 (m, 2H), 6.88 (m, 1H), 6.76 (m, 1H), 6.66 (m, 1H), 4.16 (q, J = 7.1 Hz, 2H), 2.86-2.76 (m, 4H), 2.69 (m, 2H), 2.43 (t, J = 7.6 Hz, 2H), 1.17 (t, J = 7.2 Hz, 3H) | 468 ([M + H]+) |
| 22 | 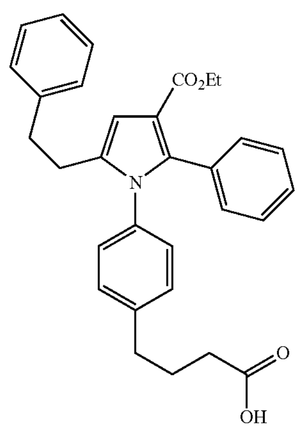 | | | CDCl3: 7.26-7.20 (m, 2H), 7.19-7.12 (m, 6H), 7.08-7.01 (m, 4H), 6.90 (m, 2H), 6.65 (m, 1H), 2.83 (m, 2H), 2.68 (m, 2H), 2.62 (m, 2H), 2.31 (t, J = 7.2 Hz, 2H), 1.91 (m, 2H), 1.17 (t, J = 7.2 Hz, 3H) | 482 ([M + H]+) |

TABLE 2-continued

Starting Materials and Example Compounds Synthesized

| Cmpd. No. | Compound Structure | Ketone/Aldehyde starting material | Aniline | 1H NMR, δ | MS |
|---|---|---|---|---|---|
| 23 | (2,5-diphenyl-pyrrolyl with phenethyl and 3-carboxyphenyl substituents) | ethyl 2-(3-oxo-5-phenylpentanoyl)-3-oxo-3-phenylpropanoate | 3-aminobenzoic acid | CDCl3 + CD3OD: 8.03 (m, 1H), 7.93 (m, 1H), 7.40 (m, 1H), 7.26-7.01 (m, 11H), 6.39 (d, J = 3.2 Hz, 1H), 6.19 (d, J = 3.6 Hz, 1H), 2.83-2.72 (m, 4H) | 368.16386 (TOF; [M + H]+) |
| 24 | (2,5-diphenyl-pyrrolyl with phenethyl and 3-(2-carboxyethyl)phenyl substituents) | ethyl 2-(3-oxo-5-phenylpentanoyl)-3-oxo-3-phenylpropanoate | 3-(3-aminophenyl)propanoic acid | CDCl3: 7.31-7.00 (m, 13H), 6.92 (m, 1H), 6.39 (d, J = 3.6 Hz, 1H), 6.16 (d, J = 3.2 Hz, 1H), 2.86 (t, J = 7.6 Hz, 2H), 2.84-2.72 (m, 4H), 2.50 (t, J = 7.6 Hz, 2H) | 396.19502 (TOF; [M + H]+) |

TABLE 2-continued

Starting Materials and Example Compounds Synthesized

| Cmpd. No. | Compound Structure | Ketone/Aldehyde starting material | Aniline | 1H NMR, δ | MS |
|---|---|---|---|---|---|
| 25 | 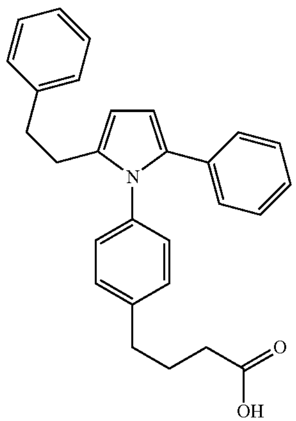 | | | CDCl3: 7.26-7.20 (m, 14H), 6.39 (d, J = 3.6 Hz, 1H), 6.17 (m, 1H), 2.84-2.73 (m, 4H), 2.70 (t, J = 7.6 Hz, 2H), 2.38 (t, J = 7.4 Hz, 2H), 1.98 (m, 2H) | 410.21222 (TOF; [M + H]+) |
| 26 | 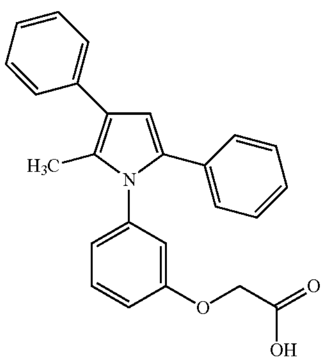 | | | CDCl3: 7.52-7.48 (m, 2H), 7.41 (m, 2H), 7.33 (m, 1H), 7.28-7.08 (m, 6H), 6.96-6.91 (m, 2H), 6.74 (m, 1H), 6.55 (s, 1H), 4.58 (s, 2H), 2.26 (s, 3H) | 384.16033 (TOF; [M + H]+) |

TABLE 2-continued
Starting Materials and Example Compounds Synthesized
| Cmpd. No. | Compound Structure | Ketone/Aldehyde starting material | Aniline | 1H NMR, δ | MS |
|---|---|---|---|---|---|
| 27 | 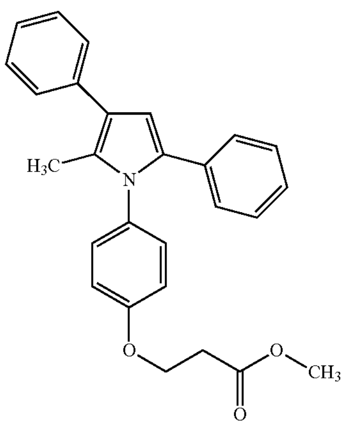 | 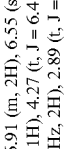 | 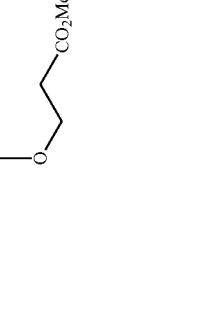 | CDCl3: 7.53-7.49 (m, 2H), 7.41 (m, 2H), 7.24 (m, 1H), 7.20-7.08 (m, 7H), 6.90 (m, 2H), 6.55 (s, 1H), 4.27 (t, J = 6.4 Hz, 2H), 3.75 (s, 3H), 2.83 (t, J = 6.0 Hz, 2H), 2.23 (s, 3H) | <cmpd did not ionize for electrospray MS> |
| 28 | 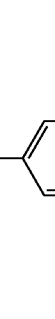 | 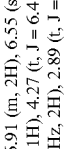 | 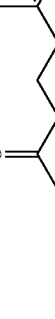 | CDCl3: 7.53-7.48 (m, 2H), 7.41 (m, 2H), 7.24 (m, 1H), 7.20-7.08 (m, 7H), 6.91 (m, 2H), 6.55 (s, 1H), 4.27 (t, J = 6.4 Hz, 2H), 2.89 (t, J = 6.2 Hz, 2H), 2.23 (s, 3H) | 396 ([M − H]−) |

TABLE 2-continued

Starting Materials and Example Compounds Synthesized

| Cmpd. No. | Compound Structure | Ketone/Aldehyde starting material | Aniline | 1H NMR, δ | MS |
|---|---|---|---|---|---|
| 29 | (2-cyclohexyl-4,5-diphenyl-pyrrol-1-yl)phenyl butanoic acid structure | 1-cyclohexyl-2,4-diphenyl-butane-1,4-dione | 4-(4-aminophenyl)butanoic acid | CD3OD 7.42-7.00 (m, 14H), 6.26 (s, 1H), 2.72 (t, J = 7.6 Hz, 2H), 2.58 (m, 1H), 2.28 (t, J = 7.6 Hz, 2H), 1.93 (m, 2H), 1.73-0.82 (m, 10H). | 462 ([M − H]−) |
| 30 | (2-isopropyl-4,5-diphenyl-pyrrol-1-yl)benzoic acid structure | 2-benzyl-5-methyl-1-phenyl-hexane-1,4-dione | 3-aminobenzoic acid | DMSO-d6 7.98 (m, 1H), 7.78 (m, 1H), 7.64-7.54 (m, 2H), 7.46-7.38 (m, 4H), 7.29 (m, 1H), 7.20-7.04 (m, 5H), 6.39 (s, 1H), 2.95 (m, 1H), 1.02 (d, J = 7.2 Hz, 3H), 0.99 (d, J = 7.2 Hz, 3H). | 380 ([M − H]−) |

TABLE 2-continued

Starting Materials and Example Compounds Synthesized

| Cmpd. No. | Compound Structure | Ketone/Aldehyde starting material | Aniline | 1H NMR, δ | MS |
|---|---|---|---|---|---|
| 31 | 2,4-diphenyl-5-isopropyl-1-(3-(2-carboxyethyl)phenyl)pyrrole | 1,3-diphenyl-2-benzyl-4-methyl-1,3-pentanedione analog | 3-aminohydrocinnamic acid | CD3OD 7.43-7.22 (m, 7H), 7.19 (m, 1H), 7.12-7.01 (m, 6H), 6.27 (s, 1H), 3.00 (m, 1H), 2.91 (m, 2H), 2.53 (m, 2H), 1.06 (d, J = 7.2 Hz, 3H), 1.05 (d, J = 7.2 Hz, 3H). | 408 ([M − H]−) |
| 32 | 2,4-diphenyl-5-isopropyl-1-(4-(3-carboxypropyl)phenyl)pyrrole | 1,3-diphenyl-2-benzyl-4-methyl-1,3-pentanedione analog | 4-aminophenylbutyric acid | CD3OD 7.41 (m, 2H), 7.35 (m, 2H), 7.28-7.17 (m, 3H), 7.19 (m, 2H), 7.12-7.00 (m, 5H), 6.27 (s, 1H), 3.00 (m, 1H), 2.71 (t, J = 7.6 Hz, 2H), 2.29 (t, J = 7.4 Hz, 2H), 1.93 (m, 2H), 1.06 (d, J = 7.2 Hz, 6H). | 422 ([M − H]−) |

TABLE 2-continued

Starting Materials and Example Compounds Synthesized

| Cmpd. No. | Compound Structure | Ketone/Aldehyde starting material | Aniline | 1H NMR, δ | MS |
|---|---|---|---|---|---|
| 33 | [structure: 1-(3-carboxyphenyl)-2-cyclopropyl-3,5-diphenylpyrrole] | [structure: 1-cyclopropyl-2,4-diphenyl-1,4-butanedione] | [structure: 3-aminobenzoic acid] | CD3OD 8.02 (m, 1H), 7.94 (m, 1H), 7.62 (m, 2H), 7.51 (m, 1H), 7.45 (m, 1H), 7.38 (m, 2H), 7.25-7.09 (m, 6H), 6.49 (s, 1H), 1.95 (m, 1H), 0.56 (m, 2H), 0.01 (m, 2H). | 378 ([M − H]−) |
| 34 | [structure: 3-[3-(2-cyclopropyl-3,5-diphenylpyrrol-1-yl)phenyl]propanoic acid] | [structure: 1-cyclopropyl-2,4-diphenyl-1,4-butanedione] | [structure: 3-(3-aminophenyl)propanoic acid] | CD3OD 7.61 (m, 2H), 7.37 (m, 2H), 7.30 (m, 1H), 7.25-7.07 (m, 8H), 7.04 (m, 1H), 6.46 (s, 1H), 2.93 (t, J = 7.4 Hz, 2H), 2.54 (t, J = 7.4 Hz, 2H), 1.94 (m, 1H), 0.54 (m, 2H), 0.01 (m, 2H). | 406 ([M − H]−) |

TABLE 2-continued

Starting Materials and Example Compounds Synthesized

| Cmpd. No. | Compound Structure | Ketone/Aldehyde starting material | Aniline | 1H NMR, δ | MS |
|---|---|---|---|---|---|
| 35 | 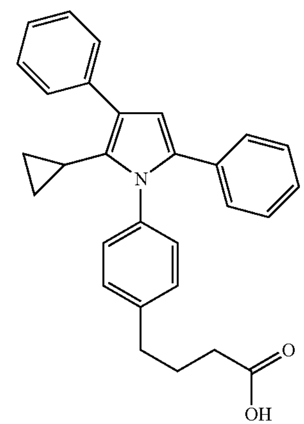 | | | CD3OD 7.60 (m, 2H), 7.36 (m, 2H), 7.27-7.06 (m, 10H), 6.45 (s, 1H), 2.72 (t, J = 7.6 Hz, 2H), 2.31 (t, J = 7.4 Hz, 2H), 2.02-1.86 (m, 3H), 0.53 (m, 2H), 0.02 (m, 2H). | 420 ([M − H]−) |
| 36 | 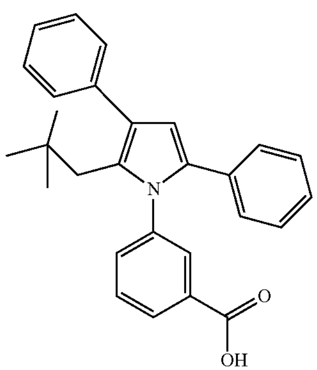 | | | CD3OD 8.00 (m, 1H), 7.81 (m, 1H), 7.53-7.46 (m, 3H), 7.39-7.34 (m, 3H), 7.21 (m, 1H), 7.17-7.06 (m, 3H), 7.02 (m, 2H), 6.40 (s, 1H), 2.91 (s, 2H), 0.41 (s, 9H). | 408 ([M − H]−) |

TABLE 2-continued

Starting Materials and Example Compounds Synthesized

| Cmpd. No. | Compound Structure | Ketone/Aldehyde starting material | Aniline | 1H NMR, δ | MS |
|---|---|---|---|---|---|
| 37 | 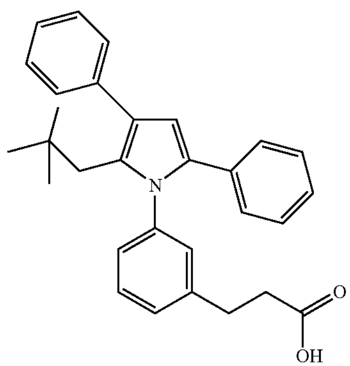 | | | CD3OD 7.49 (m, 2H), 7.35 (m, 2H), 7.29 (m, 1H), 7.21 (m, 2H), 7.15-7.04 (m, 4H), 7.03-6.96 (m, 3H), 6.37 (s, 1H), 2.92 (s, 2H), 2.88 (t, J = 7.4 Hz, 2H), 2.48 (t, J = 7.4 Hz, 2H), 0.41 (s, 9H). | 436 ([M − H]−) |
| 38 | 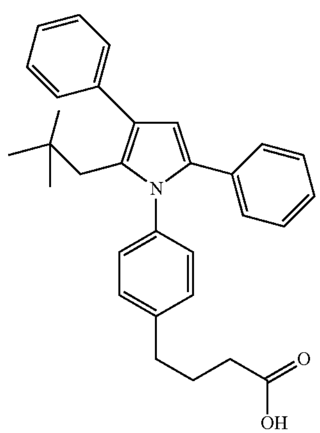 | | | CD3OD 7.49 (m, 2H), 7.35 (m, 2H), 7.26-7.17 (m, 3H), 7.14-7.04 (m, 5H), 7.01 (m, 2H), 6.37 (s, 1H), 2.91 (s, 2H), 2.71 (t, J = 7.4 Hz, 2H), 2.28 (t, J = 7.4 Hz, 2H), 1.93 (m, 2H), 0.42 (s, 9H). | 450 ([M − H]−) |

TABLE 2-continued

Starting Materials and Example Compounds Synthesized

| Cmpd. No. | Compound Structure | Ketone/Aldehyde starting material | Aniline | 1H NMR, δ | MS |
|---|---|---|---|---|---|
| 39 | ![2-methyl-3,5-diphenyl-1-(4-carboxyphenyl)pyrrole] | ![1,4-diphenyl-pentane-1,4-dione] | ![4-aminobenzoic acid] | DMSO-d6 7.99 (m, 2H), 7.50 (m, 2H), 7.42 (m, 2H), 7.39 (m, 2H), 7.28-7.18 (m, 3H), 7.13 (m, 1H), 7.08 (m, 2H), 6.63 (s, 1H), 2.19 (s, 3H). | 354 ([M + H]+) |

Example 7

Detection of Amyloid Beta Peptides with Biosource ELISA Kit (Camarillo, Calif.)

The present invention provides compositions and methods for lowering $A\beta_{42}$ levels. To test whether compounds and compositions are capable of modulating $A\beta$ levels in cultured cells, sandwich enzyme-linked immunosorbent assays (ELISAs) are employed to measure secreted $A\beta$ ($A\beta_{42}$ and/or $A\beta_{40}$ levels). In this example, H4 cells expressing wide type APP695 are seeded at 200,000 cells per well in 6 well plates, and incubated at 37° C. with 5% CO2 overnight. Cells are treated with 1.5 ml medium containing vehicle (DMSO) or a test compound at 1.25 µM, 2.5 µM, 5.0 µM and 10.0 µM (as well as other concentration if desirable) for 24 hours or 48 hours. The supernatant from treated cells is collected into eppendorf tubes and frozen at −80° C. for future analysis.

The amyloid peptide standard is reconstituted and frozen samples are thawed. The samples and standards are diluted with appropriate diluents and the plate is washed 4 times with Working Wash Buffer and patted dry on a paper towel. 100 µL per well of peptide standards, controls, and dilutions of samples to be analyzed is added. The plate is incubated for 2 hours while shaking on an orbital plate shaker at RT. The plate is then washed 4 times with Working Wash Buffer and patted dry on a paper towel. Detection Antibody Solution is poured into a reservoir and 100 µL/well of Detection Antibody Solution is immediately added to the plate. The plate is incubated at RT for 2 hours while shaking and then washed four times with Working Wash Buffer and patted dry on a paper towel. Secondary Antibody Solution is then poured into a reservoir and 100 µL/well of Secondary Antibody Solution is immediately added to the plate. The plate is incubated at RT for 2 hours with shaking, washed 5 times with Working Wash Buffer, and patted dry on a paper towel.

100 µL of stabilized chromogen is added to each well and the liquid in the wells begins to turn blue. The plate is incubated for 30 minutes at room temperature and in the dark. 100 µL of stop solution is added to each well and the plate is tapped gently to mix resulting in a change of solution color from blue to yellow. The absorbance of each well is read at 450 nm having blanked the plate reader against a chromogen blank composed of 100 µL each of stabilized chromogen and stop solution. The plate is read within 2 hours of adding the stop solution. The absorbance of the standards is plotted against the standard concentration and the concentrations of unknown samples and controls are calculated.

Example 8

Detection of Amyloid Beta Peptides with Info Genetic ELISA Kit (Gent, Belgium)

The present invention provides compositions and methods for lowering $A\beta_{42}$ levels. To test whether compounds and compositions are capable of modulating $A\beta$ levels, sandwich enzyme-linked immunosorbent assays (ELISAs) is employed to measure secreted $A\beta_{42}$ and/or $A\beta_{40}$ levels. In this example, H4 cells expressing wide type APP695 are seeded at 200,000 cells per well in 6 well plates, and incubated at 37° C. with 5% CO2 overnight. Cells are treated with 1.5 mL medium containing vehicle (DMSO) or a test compound at 1.25 µM, 2.5 µM, 5.0 µM and 10.0 µM concentration for 24 hours or 48 hours. The supernatant from treated cells is collected into eppendorf tubes and frozen at −80° C. for future analysis.

130 µL per well of samples, standards, and blanks is added to a 96-well polypropylene plate. 200 µL of samples, standards, and blanks from the polypropylene plate is added to the antibody-coated plates. The strip-holder with the appropriate number of strips is applied to the antibody-coated plates and the strips are covered with an adhesive sealer. The plate is then incubated 3 hours at room temperature while shaking on an orbital plate shaker.

The first antibody solution is prepared with Conjugate Diluent 1 at 1:100 ratio. Each well of the antibody-coated plates is washed 5 times with 400 µL washing solution and 100 µL of the prepared first antibody solution is added to each well. The strips are applied to the plate, covered with an adhesive sealer, and the plate is incubated for 1 hour at room temperature while shaking on an orbital plate shaker.

The second antibody (conjugate 2) solution is prepared with Conjugate Diluent 2 at 1:100 ratio. Each well of the antibody-coated plates are washed for 5 times with 400 µL washing solution and 100 µL of the prepared second antibody solution is added to each well. The strips are applied, covered with an adhesive sealer, and the plate is incubated 30 min at room temperature while shaking on an orbital plate shaker. Each well of the antibody-coated plates is then are washed for 5 times with 400 µL washing solution.

A substrate solution is prepared by diluting substrate 100× with HRP Substrate Buffer. 100 µL of the prepared substrate solution is added to each well of the antibody-coated plate. The strips are applied, covered with an adhesive sealer, and the plate is incubated for 30 min at room temperature. 100 µL Stop Solution is then added to each well to stop the reaction. The strip-holder is carefully taped to ensure through mixing. The reader is blanked and the absorbance of the solution in the wells is read at 450 nm. The absorbance of the standards is plotted against the standard concentration and the concentration of samples is calculated using the standard curve.

Example 9

Specific Detection of Amyloid Beta 1-40 ($A\beta_{40}$) with Antibodies from Signet Laboratories (Dedham, Mass.)

Secreted $A\beta_{40}$ levels were also measured with sandwich ELISAs using antibodies from Signet Laboratories. Typically, Maxisorp plates (Nalge Nunc International. Rochester, N.Y.) were coated with a mouse monoclonal antibody (clone 6E10) directed against human amyloid beta protein (Catalog No. 9320-10; Signet Laboratories, Dedham, Mass.), as recommended by the supplier. The amyloid antigen from the cell culture supernatants was captured on the plate by incubating appropriate dilutions of the sample. The bound amyloid peptide $A\beta_{40}$ was detected by incubating with an affinity purified rabbit polyclonal antibody directed against $A\beta_{40}$ (Catalog No. 9130-005; Signet Laboratories, Dedham, Mass.). The amount of antibody bound was then measured with a peroxidase-conjugated, affinity purified donkey anti-rabbit IgG (Catalog No. 711-035-152; Jackson ImmunoResearch Laboratories, West Grove, Pa.). In some instances the affinity purified rabbit polyclonal antibody directed against $A\beta_{40}$ was biotinylated (Catalog No. 9133-005; Signet Laboratories, Dedham, Mass.). In these cases the bound antibody was detected with streptavidin conjugated with horseradish peroxidase (Catalog. No. RPN1231, Amersham Biosciences, GE Healthcare, Piscataway, N.J.). In both cases the amount of bound peroxidase was determined with a QuantaBlu fluorogenic peroxidase substrate kit (Catalog No. 15169; Pierce Biotechnology, Rockford, Ill.).

Example 10

Specific Detection of Amyloid Beta 1-42 ($A\beta_{42}$) with with Antibodies from Signet Laboratories (Dedham, Mass.)

Secreted $A\beta_{42}$ levels were also measured with sandwich ELISAs using antibodies from Signet Laboratories. Typically, Maxisorp plates (Nalge Nunc International. Rochester, N.Y.) were coated with a mouse monoclonal antibody (clone 6E10) directed against human amyloid beta protein (Catalog No. 9320-10; Signet Laboratories, Dedham, Mass.) as recommended by the supplier. The amyloid antigen from the cell culture supernatants was captured on the plate by incubating appropriate dilutions of the sample. The bound amyloid peptide $A\beta_{42}$ was detected by incubating with an affinity purified rabbit polyclonal antibody directed against $A\beta_{42}$ (Catalog No. 9136-005; Signet Laboratories, Dedham, Mass.). The amount of antibody bound was then measured with a peroxidase-conjugated, affinity purified donkey anti-rabbit IgG (Catalog No. 711-035-152; Jackson ImmunoResearch Laboratories, West Grove, Pa.). The amount of bound peroxidase was determined with a QuantaBlu fluorogenic peroxidase substrate kit (Catalog No. 15169; Pierce Biotechnology, Rockford, Ill.).

Example 11

Modulation of Amyloid Beta Peptide Secretion by Compounds of the Present Invention Modulation of amyloid beta peptide ($A\beta_{40}$ and $A\beta_{42}$) secretion was examined using the methods described in Examples 4, 5, 6, and 7, above. Generally, for determining % inhibition of secretion, H4 test cells were contacted with test compound at a concentration of 100 μM, and H4 control cells were contacted with an equivalent volume of the solvent in which the compounds were dissolved (DMSO). Test cells and control cells were treated, and conditioned cell culture medium was collected from the cell cultures at 24 or 48 hours, and assayed for secreted amyloid peptides. Experiments were done in triplicate and the % inhibition of $A\beta_{40}$ and $A\beta_{42}$ secretion was determined by comparison of the experimental samples with the control samples. For determining IC50 values, H4 cells were treated with test compound over a range of concentrations, from about 1 μM to about 100 μM (and higher concentrations if needed), and matched control cells were were contacted with an equivalent volume of the solvent in which the compounds were dissolved (DMSO). Conditioned cell culture medium was collected from the cell cultures at 24 or 48 hours, and assayed for secreted amyloid peptides. Experiments were also generally done in triplicate and the IC50 of $A\beta_{40}$ and $A\beta_{42}$ secretion was determined by comparison of the experimental samples with the control samples using standard methods. The results of these assays for the compounds of the present invention are presented in Table 3, below. For those compounds where multiple results are reported, each number represents the results of an independent set of assays.

TABLE 3

| | | Amyloid Beta Modulating Activity of Example Compounds | | | |
|---|---|---|---|---|---|
| Cmpd. No. | Compound Structure | % Inhibition of Aβ42 Secretion @ 100 μM | Aβ42 Secretion IC50 (μM) | % Inhibition of Aβ40 Secretion @ 100 μM | Aβ40 Secretion IC50 (μM) |
| 1 | 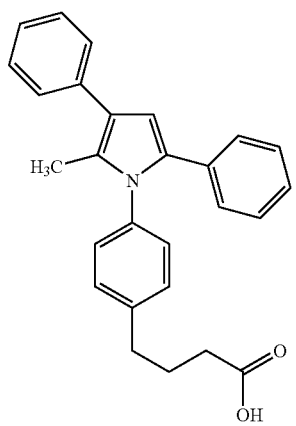 | 101, 99, 78 | 6, 8, 17 | 5, 78, 19 | >100, 67, >100 |

TABLE 3-continued

Amyloid Beta Modulating Activity of Example Compounds

| Cmpd. No. | Compound Structure | % Inhibition of Aβ42 Secretion @ 100 μM | Aβ42 Secretion IC50 (μM) | % Inhibition of Aβ40 Secretion @ 100 μM | Aβ40 Secretion IC50 (μM) |
|---|---|---|---|---|---|
| 2 | 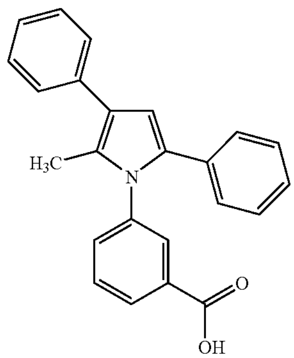 | 76 | 48 | 36 | >100 |
| 3 | 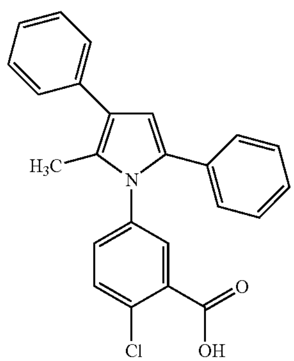 | 89 | 37 | 52 | 98 |
| 4 | 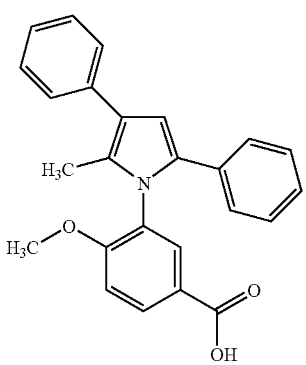 | 84 | 29 | 22 | >100 |
| 5 | 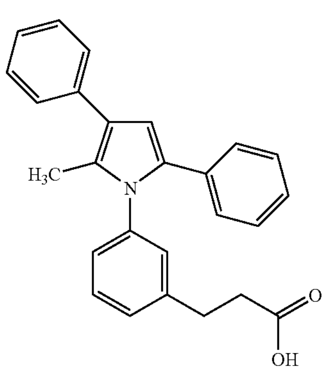 | 55 | 100 | 31 | >100 |

TABLE 3-continued

Amyloid Beta Modulating Activity of Example Compounds

| Cmpd. No. | Compound Structure | % Inhibition of Aβ42 Secretion @ 100 μM | Aβ42 Secretion IC50 (μM) | % Inhibition of Aβ40 Secretion @ 100 μM | Aβ40 Secretion IC50 (μM) |
|---|---|---|---|---|---|
| 6 | 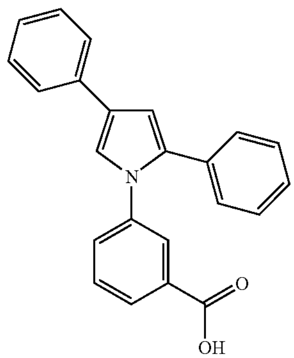 | 74 | 30 | 32 | >100 |
| 7 | 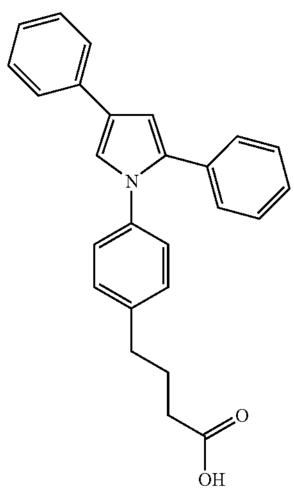 | 76 | 52 | 7 | >100 |
| 8 | 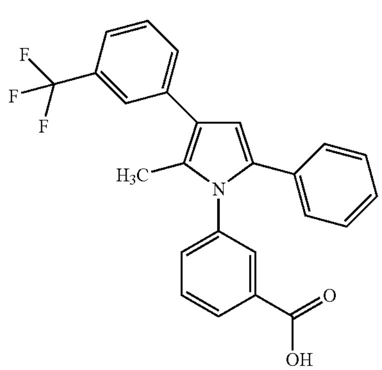 | 94, 80 | 9, 24 | 88, 64 | 38, 78 |

TABLE 3-continued
Amyloid Beta Modulating Activity of Example Compounds
| Cmpd. No. | Compound Structure | % Inhibition of Aβ42 Secretion @ 100 μM | Aβ42 Secretion IC50 (μM) | % Inhibition of Aβ40 Secretion @ 100 μM | Aβ40 Secretion IC50 (μM) |
|---|---|---|---|---|---|
| 9 | 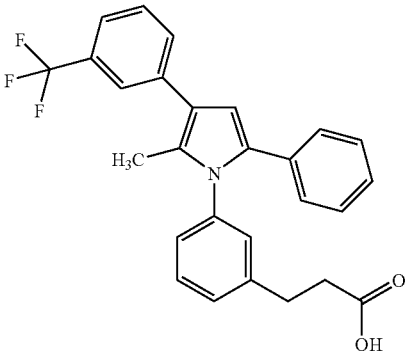 | 82 | 15 | 86 | 28 |
| 10 | 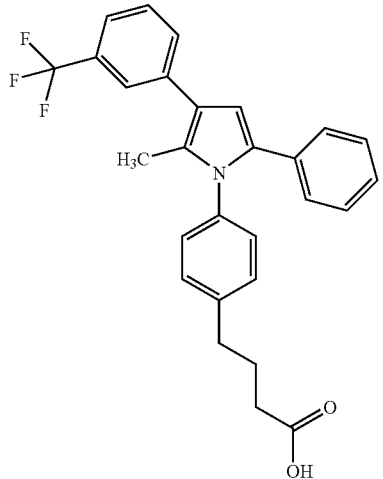 | 79 | 15 | 97 | 11 |
| 11 | 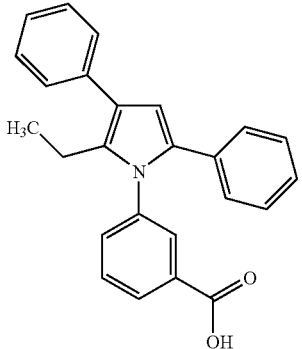 | 92, 94, 78 | 17, 44, 21 | 31, 91, 74 | >100, 69, 68 |

TABLE 3-continued
Amyloid Beta Modulating Activity of Example Compounds
| Cmpd. No. | Compound Structure | % Inhibition of Aβ42 Secretion @ 100 μM | Aβ42 Secretion IC50 (μM) | % Inhibition of Aβ40 Secretion @ 100 μM | Aβ40 Secretion IC50 (μM) |
|---|---|---|---|---|---|
| 12 | 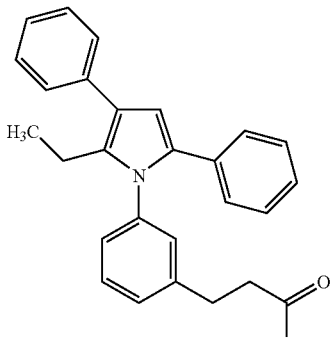 | 85 | 34 | 27 | >100 |
| 13 | 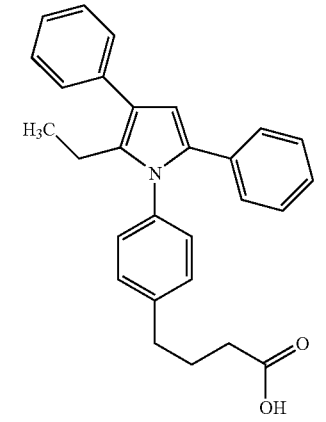 | 83 | 12 | 14 | >100 |
| 14 | 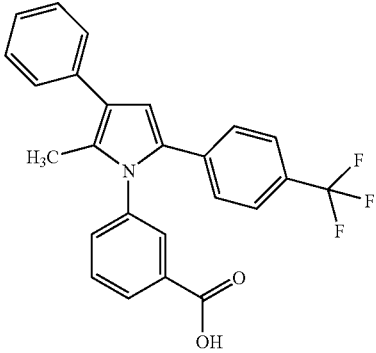 | 96, 101, 99, 92 | 5, 12, 14, 15 | 44, 100, 96, 87 | >100, 38, 22, 28 |
| 15 | 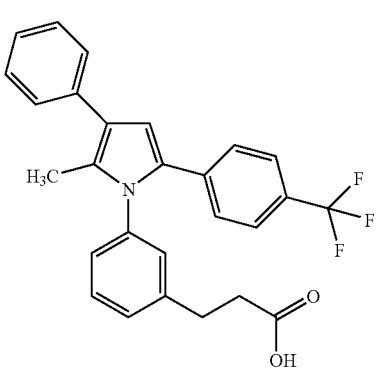 | 96 | 21 | 63 | 82 |

TABLE 3-continued

Amyloid Beta Modulating Activity of Example Compounds

| Cmpd. No. | Compound Structure | % Inhibition of Aβ42 Secretion @ 100 μM | Aβ42 Secretion IC50 (μM) | % Inhibition of Aβ40 Secretion @ 100 μM | Aβ40 Secretion IC50 (μM) |
|---|---|---|---|---|---|
| 16 | 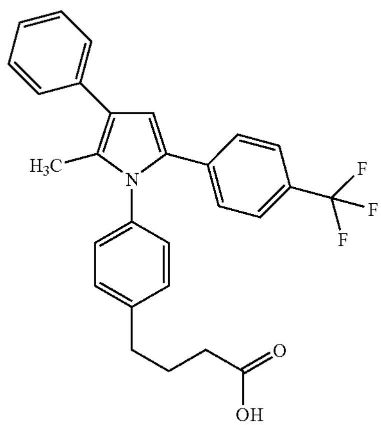 | 97, 102 | 5, 10 | 78, 93 | 70, 23 |
| 17 | 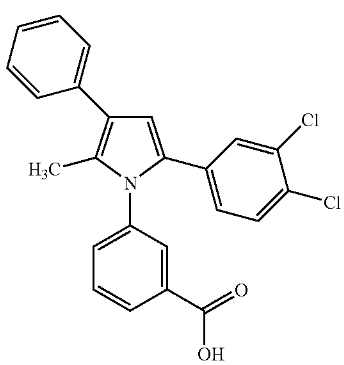 | 83 | 10 | 10 | >100 |
| 18 | 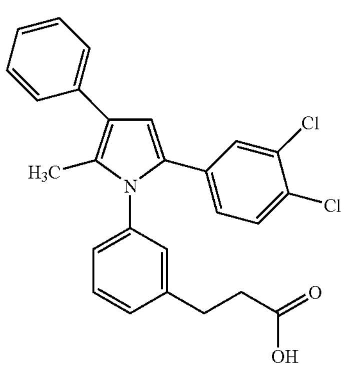 | 94 | 10 | 41 | >100 |

TABLE 3-continued
Amyloid Beta Modulating Activity of Example Compounds
| Cmpd. No. | Compound Structure | % Inhibition of Aβ42 Secretion @ 100 μM | Aβ42 Secretion IC50 (μM) | % Inhibition of Aβ40 Secretion @ 100 μM | Aβ40 Secretion IC50 (μM) |
|---|---|---|---|---|---|
| 19 | 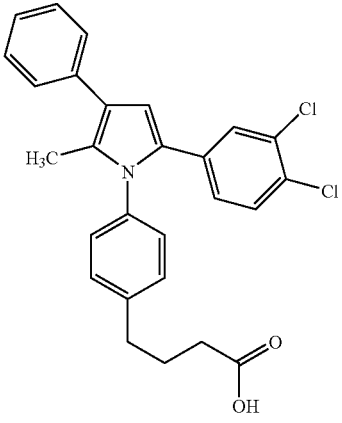 | 95, 109 | 2, 10 | 42, 78 | >100, 65 |
| 20 | 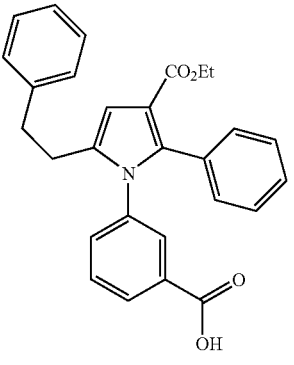 | 95 | 21 | 49 | >100 |
| 21 | 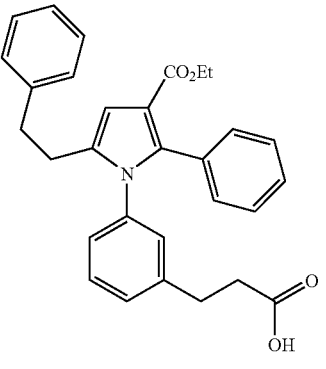 | 66 | 55 | 38 | >100 |

TABLE 3-continued

Amyloid Beta Modulating Activity of Example Compounds

| Cmpd. No. | Compound Structure | % Inhibition of Aβ42 Secretion @ 100 μM | Aβ42 Secretion IC50 (μM) | % Inhibition of Aβ40 Secretion @ 100 μM | Aβ40 Secretion IC50 (μM) |
|---|---|---|---|---|---|
| 22 | 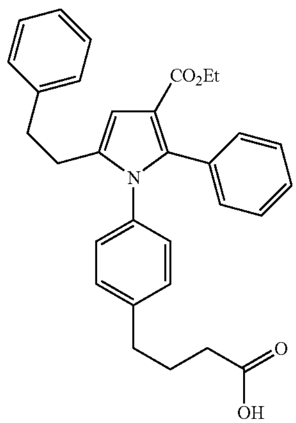 | 68 | 55 | 65 | 40 |
| 23 | 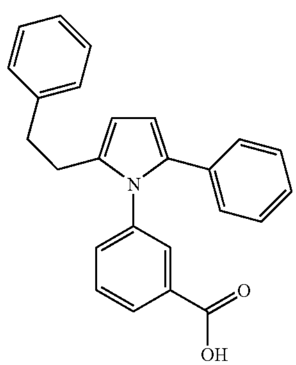 | 77 | 23 | 67 | 70 |
| 24 | 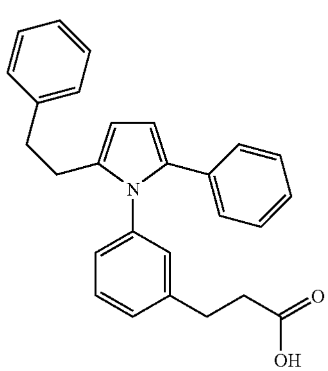 | 73 | 52 | 52 | 100 |

TABLE 3-continued

Amyloid Beta Modulating Activity of Example Compounds

| Cmpd. No. | Compound Structure | % Inhibition of Aβ42 Secretion @ 100 μM | Aβ42 Secretion IC50 (μM) | % Inhibition of Aβ40 Secretion @ 100 μM | Aβ40 Secretion IC50 (μM) |
|---|---|---|---|---|---|
| 25 | 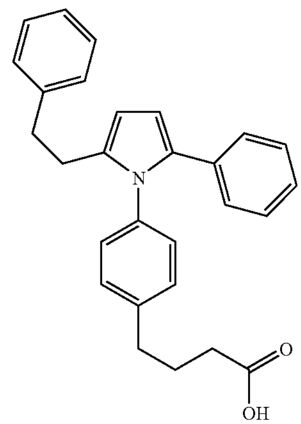 | 40 | >100 | 30 | >100 |
| 26 | 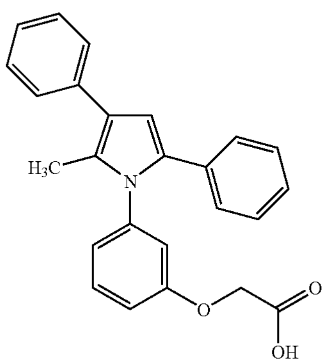 | 147 | 21 | 94 | 42 |
| 27 | 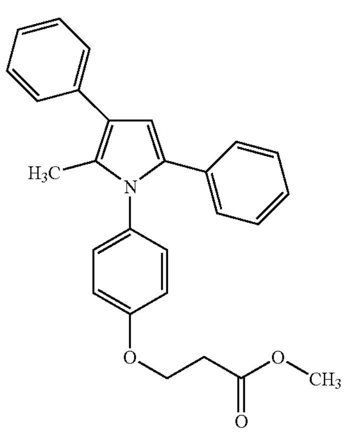 | nd | nd | nd | nd |

TABLE 3-continued

Amyloid Beta Modulating Activity of Example Compounds

| Cmpd. No. | Compound Structure | % Inhibition of Aβ42 Secretion @ 100 μM | Aβ42 Secretion IC50 (μM) | % Inhibition of Aβ40 Secretion @ 100 μM | Aβ40 Secretion IC50 (μM) |
|---|---|---|---|---|---|
| 28 | 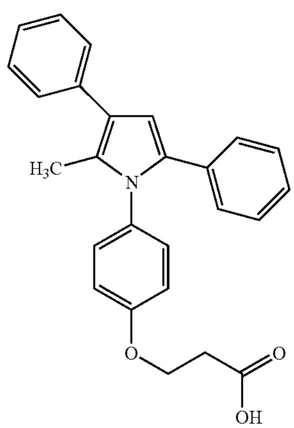 | 55 | 80 | 32 | >32 |
| 29 | 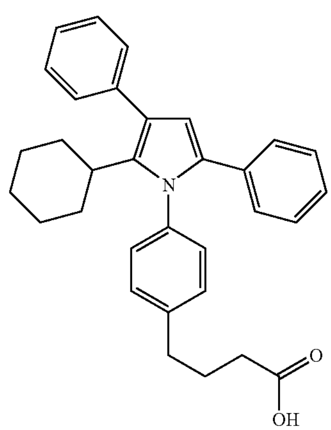 | 102 | 14 | 103 | 33 |
| 30 | 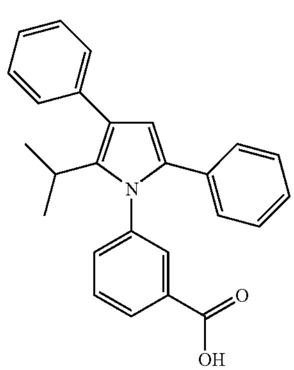 | 99 | 15 | 101 | 22 |

TABLE 3-continued

Amyloid Beta Modulating Activity of Example Compounds

| Cmpd. No. | Compound Structure | % Inhibition of Aβ42 Secretion @ 100 μM | Aβ42 Secretion IC50 (μM) | % Inhibition of Aβ40 Secretion @ 100 μM | Aβ40 Secretion IC50 (μM) |
|---|---|---|---|---|---|
| 31 | 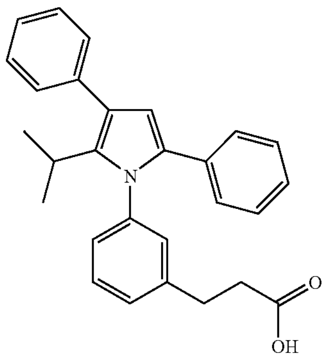 | 95 | 21 | 106 | 23 |
| 32 | 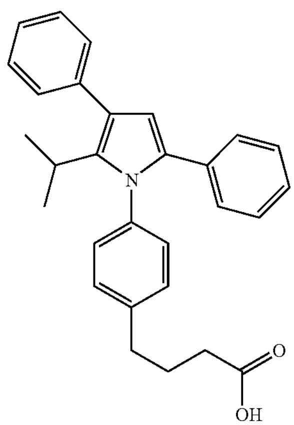 | 98 | 22 | 103 | 41 |
| 33 | 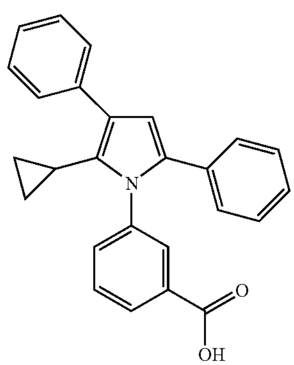 | 89, 86 | 21, 24 | 73, 73 | 74, 79 |
| 34 | 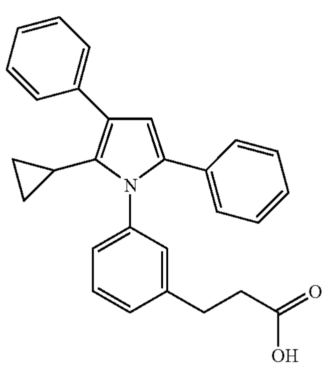 | 95 | 30 | 100 | 48 |

TABLE 3-continued
Amyloid Beta Modulating Activity of Example Compounds
| Cmpd. No. | Compound Structure | % Inhibition of Aβ42 Secretion @ 100 μM | Aβ42 Secretion IC50 (μM) | % Inhibition of Aβ40 Secretion @ 100 μM | Aβ40 Secretion IC50 (μM) |
|---|---|---|---|---|---|
| 35 | 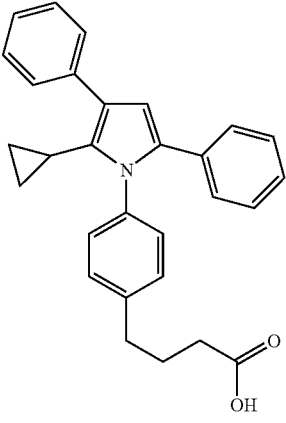 | 83, 93 | 29, 24 | 73, 96 | 79, 68 |
| 36 | 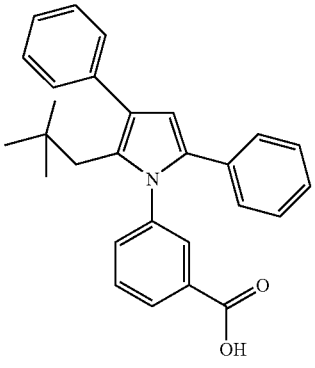 | 99, 101 | 8, 7 | 103, 96 | 29, 19 |
| 37 | 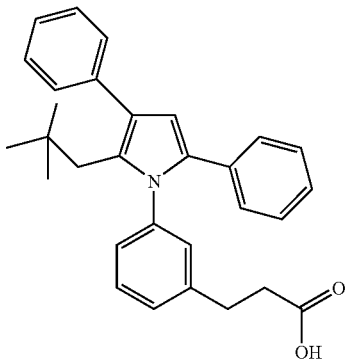 | 100, 99 | 9, 7 | 98, 104 | 30, 32 |

TABLE 3-continued

Amyloid Beta Modulating Activity of Example Compounds

| Cmpd. No. | Compound Structure | % Inhibition of Aβ42 Secretion @ 100 μM | Aβ42 Secretion IC50 (μM) | % Inhibition of Aβ40 Secretion @ 100 μM | Aβ40 Secretion IC50 (μM) |
|---|---|---|---|---|---|
| 38 | *(structure)* | 94, 101 | 10, 7 | 88, 104 | 63, 37 |
| 39 | *(structure)* | 86 | 50 | 92 | 54 |

Example 12

Neuroprotection Assay

The present invention provides compositions and methods for slowing the death or decline of neurons. To test the ability of compositions of the present invention to protect against neurotoxicity, adult female Sprague Dawley rats are obtained and injected intraperitoneally with various doses of a composition of the present invention. At the same time, the test animals also receive a subcutaneous injection of MK-801 (0.5 mg/kg), which has been shown to consistently induce, in all treated rats, a fully developed neurotoxic reaction consisting of acute vacuole formation in the majority of pyramidal neurons in layers III and IV of the posterior cingulate and retrosplenial (PC/RS) cortices.

Control animals are administered the liquid which was used to dissolve the test agent and the same dosage of MK-801 (0.5 mg/kg sc). The animals are sacrificed four hours after treatment and the number of vacuolated PC/RS neurons are counted on each side of the brain, at a rostrocaudal level immediately posterior to where the corpus callosum ceases decussating across the midline (approximately 5.6 mm caudal to bregma). The toxic reaction approaches maximal severity at this level and shows very little variability between different animals.

Percentage reduction in neurotoxicity is calculated by dividing the mean number of vacuolated neurons in a given treatment group, by the mean number of vacuolated neurons in control animals that were treated with MK-801 but not the protective agent. The result is subtracted from one and multiplied by 100, to calculate a percentage. Linear regression analysis can be used to determine an ED50 (i.e., the dosage of a given compound that reduces the mean number of vacuolated neurons to 50% of the value in control animals), with the 25th and 75th percentiles defining the confidence limits.

Example 13

Treatment of Animals with a Compound to Determine the Compound's Effect on Levels of Aβ$_{42}$ and Alzheimer's Disease To determine the effect of a composition of the present invention on levels of Aβ$_{42}$ and AD, an animal is treated with the compound and the levels of Aβ$_{42}$ in the brain are measured. Three month-old TG2576 mice that overexpress APP (695) with the "Swedish" mutation (APP695NL) are used. Mice overexpressing APP(695) with the "Swedish" mutation have high levels of soluble Aβ in the their brains and develop memory deficits and plaques with age, making them suitable for examining the effect of compounds on levels of Aβ$_{42}$ and AD. "Test" TG25276 mice are treated with the compound and "control" TG25276 mice are not. The brain levels of SDS-soluble A$\beta_{40}$ and A$\beta_{42}$ for "test" mice are compared to "control" mice using ELISA. Test mice that have a reduction in A$\beta_{42}$ levels suggest that treatment with the compound could prevent amyloid pathology by decreasing the ratio of A$\beta_{42}$ to A$\beta_{40}$ in the brain.

Example 14

Treatment of Animals with a Compound to Determine the Compound's Effect on Memory and Alzheimer's Disease The present invention provides compositions and methods for treating or preventing AD. To test the effect of compositions of the present invention on memory and AD, TG2576 mice that overexpress APP(695) with the "Swedish" mutation (APP695NL) are used. Mice overexpressing APP(695) with the "Swedish" mutation develop memory deficits and plaques with age, making them suitable for examining the effect of compounds on memory and AD. The test compound is administered daily for two weeks to test groups of the TG2576 mice in age groups of: 1) 4-5 months, 2) 6-11 months, 3) 12-18 months, and 4) 20-25 months. Groups of control TG2576 mice of corresponding ages are not administered the compound. Both control and test groups then have memory tested in a version of the Morris water maze (Morris, *J. Neurosci. Methods* 11:47-60 (1984)) that is modified for mice. The water maze contains a metal circular pool of about 40 cm in height and 75 cm in diameter. The walls of the pool have fixed spatial orientation clues of distinct patterns or shelves containing objects. The pool is filled with room temperature water to a depth of 25 cm and an escape platform is hidden 0.5 cm below the surface of the 25-cm-deep water at a fixed position in the center of one of the southwest quadrant of pool. The test and control mice are trained for 10 days in daily sessions consisting of four trials in which the mouse starts in a different quadrant of the pool for each trial. The mice are timed and given 60 seconds to find the escape platform in the pool. If the mice have not found the escape platform after 60 seconds, they are guided into it. The mice are then allowed to rest on the platform for 30 seconds and the amount of time it takes the mice to find the platform is recorded. Probe trials are run at the end of the trials on the 4th, 7th, and 10th days of training, in which the platform is removed and the mice are allowed to search for the platform for 60 sec. The percentage of time spent in the quadrant where the platform was in previous trials is calculated.

In training trials, the time it takes test group mice to reach the escape platform is compared to the time taken by control group mice of corresponding ages. In probe trials, the percentage of time spent by test group mice in the quadrant where the platform was in previous trials is compared to the percentage time spent by control mice. Quicker location of the escape platform in training trials and/or an increased percentage time spent in the previous quadrant of the maze during probe trials is indicative of spatial learning and memory. Because memory loss is a hallmark of AD, test mice that have better learning and memory when compared to control mice indicate that the compound may be effecting in treating or slowing AD and/or its symptoms.

Example 15

Treatment of MCI with a Compound of Formulae I-VI

A therapeutic compound of Formulae I-VI can be used to treat MCI by administering tablets containing 50 mg of the compound, and/or oral gel capsules containing 50 mg of the compound. The typical dosage may be 50, 100, 300 or 600 mg of active ingredients daily. A typical dosage regimen may have 100 mg of the compound taken daily (50 mg twice daily). Another typical dosage may have 50 mg of the compound taken once daily. These dosages can also be divided or modified, and taken with or without food.

Example 16

Treatment of Alzheimer's Disease with a Compound of Formulae I-VI

The therapeutic compound of Formulae I-VI can be administered once daily as a tablet containing 1-200 mg of active ingredient or as a capsule containing 1-200 mg of the active ingredient. Typically, for the treatment of mild-to-moderate AD, an individual is diagnosed by a doctor as having the disease using a suitable combination of observations. One criterion indicating a likelihood of mild-to-moderate AD is a score of about 15 to about 26 on the MMSE test. Another criteria indicating mild-to-moderate AD is an observed decline in cognitive function. The compound can also be administered in liquid or other dosage forms. The dosages can also be divided or modified, and taken with or without food. For example, the 200 mg dose can be divided into two 100 mg tablets or capsules.

Depending on the stage of the disease, the therapeutic compound of Formulae I-VI can also be administered once daily in liquid, capsule, or tablet dosage forms where the dose has various amounts of compound (i.e., 300 mg, 250 mg, 200 mg, 175 mg, 150 mg, 125 mg, 100 mg, 75 mg, 50 mg, 40 mg, 30 mg, 25 mg, 15 mg, 10 mg and 1 mg). Again, the dosages can also be divided or modified, and taken with or without food. The doses can be taken during treatment with other medications for treating AD or symptoms thereof. For example, the compound of Formulae I-VI can be administered in the morning as a tablet containing 100 mg of active ingredient and an acetylcholine esterase inhibitor (i.e., tacrine (Cognex®), donepezil (Aricept®), rivastigmine (Exelon®), and galantamine (Reminyl®)), and/or an NMDA antagonist (i.e., memantine). It may be desirable to lower the amount of acetylcholine esterase inhibitor (and/or NMDA antagonist) to avoid adverse side effects associated with higher doses of these compounds. Alternatively, the acetylcholine esterase inhibitor (and/or NMDA antagonist) can be co-formulated into a single dosage form, i.e., liquid, tablet, capsule, etc.

Patients having mild-to-moderate AD undergoing the treatment regimen of this example with a therapeutic compound of Formulae I-VI in doses of about 1 mg to 400 mg can experience a lessening in decline of cognitive function (as measured by the ADAS-cog or CDR sum of boxes), plaque pathology, and/or biochemical disease marker progression.

Example 17

Prevention of Alzheimer's Disease

Prior to the onset of symptoms of AD or just at the very beginning stages of the disease, patients desiring prophylaxis against AD can be treated with a prophylactically effective amount of a therapeutic compound of Formulae I-VI. Those needing prophylaxis can be assessed by monitoring assayable disease markers, detection of genes conferring a predisposition to the disease, other risks factors such as age, diet, other disease conditions associated with AD. The patient can also be treated with a combination of NMDA, and a therapeutic compound of Formulae I-VI to delay or prevent the onset of AD or symptoms thereof.

The patient desiring prophylaxis against AD or prophylaxis of a worsening of the symptoms of AD can be treated with a therapeutic compound of Formulae I-VI in an amount sufficient to delay the onset or progression of symptoms of AD. For example, a patient can be treated with 100 mg of a compound of Formulae I-VI once daily. Another preventive regimen involves administering to the patient 50 mg of compound of Formulae I-VI once daily. These amounts of these active ingredients can be modified to lessen side-effects and/or produce the most therapeutic benefit. For example, 25 mg of a therapeutic compound of Formulae I-VI twice daily can be administered to reduce side-effects associated with the use of higher levels of the active ingredient. The preventive treatment can also be, e.g., treatment on alternating days with compound of Formulae I-VI or alternating weeks. Other preventive treatment regimens include, but are not limited to, treatment with compound of Formulae I-VI for 3 weeks out of every 4 weeks, or for several months followed by no treatment for a month and then treatment for several months in an alternating on/off schedule to reduce side effects or toxicity problems.

Patients desiring or in need of prophylaxis against AD undergoing the preventive regimen of this example with a therapeutic compound of Formulae I-VI doses of about 1 mg to 400 mg can decelerate or delay the onset of AD or prevent the occurrence of AD. It can be advantageous to utilize a low dosage prevention regimen that involves administration of pharmaceutical doses of 50 mg compound of Formulae I-VI once daily.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference. The mere mentioning of the publications and patent applications does not necessarily constitute an admission that they are prior art to the instant application.

Although the foregoing invention has been described in some detail by way of illustration and example for purposes of clarity of understanding, it will be obvious that certain changes and modifications may be practiced within the scope of the appended claims.

What is claimed is:
1. A compound having a structure according to Formula I:

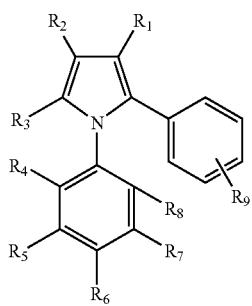

(I)

or a pharmaceutically acceptable salt thereof, wherein:
$R_1$ is a hydrogen atom, halogen, hydroxyl, $C_{1-6}$ alkyl optionally substituted with 1, 2, or 3 halogens or hydroxyls, $C_{1-6}$ alkoxy or $-(CH)_qCO_2R_{10}$, wherein $R_{10}$ is a hydrogen atom or $C_{1-6}$ alkyl, and q is the integer 0, 1, 2, 3, or 4;

$R_2$ is a hydrogen atom, halogen, hydroxyl, $C_{1-6}$ alkyl optionally substituted with 1, 2, or 3 halogens or hydroxyls, $C_{1-6}$ alkoxy optionally substituted with 1, 2, or 3 halogens, hydroxyls or amino groups, or phenyl, optionally substituted with 1, 2, 3, 4, or 5 of the same or different substituents chosen from halogen, $C_{1-6}$ alkyl optionally substituted with 1, 2, or 3 halogens or hydroxyls, or $-(CH)_qCO_2R_{10}$ wherein $R_{10}$ is a hydrogen atom or a $C_{1-6}$ alkyl and q is the integer 0, 1, 2, 3, or 4;

$R_3$ is a hydrogen atom, halogen, hydroxyl, $C_{1-6}$ alkyl optionally substituted with 1, 2, or 3 halogens or hydroxyls, $C_{1-6}$ alkoxy optionally substituted with 1, 2, or 3 halogens, hydroxyls or amino groups, when $R_2$ is an optionally substituted phenyl; or, when $R_2$ is not an optionally substituted phenyl, $R_3$ is $-CH_2CH_2$-phenyl, optionally substituted with 1, 2, 3, 4, or 5 of the same or different substituents chosen from halogen, $C_{1-6}$ alkyls optionally substituted with 1, 2, or 3 halogens or hydroxyls, or $-(CH)_qCO_2R_{10}$, wherein $R_{10}$ is a hydrogen atom or a $C_{1-6}$ alkyl, and q is the integer 0, 1, 2, 3, or 4;

$R_4$ is a hydrogen atom, halogen, hydroxyl, $C_{1-6}$ alkyl optionally substituted with 1, 2, or 3 halogens or hydroxyls, or $C_{1-6}$ alkoxy optionally substituted with 1, 2, or 3 halogens, hydroxyls or amino groups;

$R_5$ is a hydrogen atom, halogen, hydroxyl, $C_{1-6}$ alkyl optionally substituted with 1, 2, or 3 halogens or hydroxyls, or $C_{1-6}$ alkoxy optionally substituted with 1, 2, or 3 halogens, hydroxyls or amino groups;

one of $R_6$ and $R_7$ is $-(CH_2)_nCO_2R_{11}$, $-O(CH_2)_nCO_2R_{11}$, or $-(CH_2)_mO(CH_2)_pCO_2R_{11}$, wherein n is the integer 0, 1, 2, 3, 4, 5, or 6, wherein m is the integer 0, 1, 2, 3, or 4, and p is the integer from 0, 1, 2, 3, 4, 5, or 6, and $R_{11}$ is a hydrogen atom or $C_{1-6}$ alkyl optionally substituted with 1, 2, or 3 halogens, or one of $R_6$ and $R_7$ is -L-C(=O)OH, -L-CH=CHC(=O)OH, -L-C(=)NH$_2$, -L-C(=)NH(C$_{1-3}$ alkyl), -L-C(=O)N(C$_{1-3}$ alkyl)$_2$, -L-C(=O)NHOH, -L-C(=O)CH$_2$NH$_2$, -LC(=O)CH$_2$OH, L-C(=O)CH$_2$SH, -L-C(=O)NHCN, -L-sulfo, -L-(2,6 difluorophenol), -L-phosphono, and -L-tetrazolyl, wherein L is saturated, partially saturated, or unsaturated, and is selected from the group consisting of $-(CH_2)_n-(CH2)_n-$, $-(CH_2)_nC(=O)(CH_2)_n-$, $-(CH_2)_nNH(CH_2)_n-$, $-(CH2)_nO(CH_2)_n-$, and $-(CH_2)_nS(CH_2)_n-$, wherein each n is an integer independently selected from 0, 1, 2, 3, 4, 5, 6, 7, and 8, wherein each carbon is optionally substituted with one or more $C_{1-3}$ alkyl or $C_{3-6}$ cycloalkyl;

while the other of $R_6$ and $R_7$ is a hydrogen atom, halogen, hydroxyl, $C_{1-6}$ alkyl optionally substituted with 1, 2, or 3 halogens, $C_{1-6}$ alkoxy optionally substituted with 1, 2, or 3 halogens, hydroxyls, or amino groups;

$R_8$ is a hydrogen atom, halogen, hydroxyl, $C_{1-6}$ alkyl optionally substituted with 1, 2, or 3 halogens or hydroxyls, or $C_{1-6}$ alkoxy optionally substituted with 1, 2, or 3 halogens, hydroxyls or amino groups; and $R_9$ is independently 0, 1, 2, 3, 4, or 5 substituents, which are independently selected from a hydrogen atom, halogen, hydroxyl, $C_{1-6}$ alkyl (optionally substituted with 1, 2, or 3 halogens or hydroxyl groups), $C_{1-6}$ haloalkyl, aryl, heteroaryl, heterocycle, $-OR$, $-C(=O)R$, $-C(=O)OR$, $-C(=O)NRR$, $-NRR$, $-NRC(=O)R$, $-NRC(=O)OR$, $-NRC(=O)NRR$, $-OC(=O)R$, $-OC$ (=O)OR, —OC(=O)NRR, —SH, —SR, —SOR, —SO$_2$R, —SO$_2$NR$_2$, —NRSO$_2$R, —NR$_2$SO$_2$R, —Si(R)$_3$, or —OP(OR)$_3$, wherein each occurrence of R is the same or different and independently a hydrogen atom, C$_{1-6}$ alkyl, substituted alkyl, aryl, substituted aryl, arylalkyl, substituted arylalkyl, heterocycle, substituted heterocycle, heterocyclealkyl or substituted heterocyclealkyl, or wherein any two R groups attached to the same nitrogen atom, taken together with the nitrogen atom to which they are attached, form a heterocyclic ring or a substituted heterocyclic ring.

2. A compound of claim 1, wherein R$_1$, R$_5$ and R$_8$ are hydrogen atoms, and the compound has a structure according to Formula II:

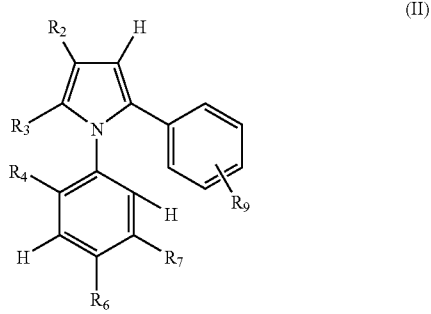

(II)

or a pharmaceutically acceptable salt thereof, wherein:
R$_2$ is a hydrogen atom, halogen, hydroxyl, C$_{1-6}$ alkyl optionally substituted with 1, 2, or 3 halogens or hydroxyls, C$_{1-6}$ alkoxy optionally substituted with 1, 2, or 3 halogens, hydroxyls or amino groups, or phenyl, optionally substituted with 1, 2, 3, 4, or 5 of the same or different substituents chosen from halogen, C$_{1-6}$ alkyl optionally substituted with 1, 2, or 3 halogens or hydroxyls, or —(CH)$_q$CO$_2$R$_{10}$ wherein R$_{10}$ is a hydrogen atom or a C$_{1-6}$ alkyl and q is the integer 0, 1, 2, 3, or 4;

R$_3$ is a hydrogen atom, halogen, hydroxyl, C$_{1-6}$ alkyl optionally substituted with 1, 2, or 3 halogens or hydroxyls, C$_{1-6}$ alkoxy optionally substituted with 1, 2, or 3 halogens, hydroxyls or amino groups, when R$_2$ is an optionally substituted phenyl; or, when R$_2$ is not an optionally substituted phenyl, R$_3$ is —CH$_2$CH$_2$—phenyl, optionally substituted with 1, 2, 3, 4, or 5 of the same or different substituents chosen from halogen, C$_{1-6}$ alkyls optionally substituted with 1, 2, or 3 halogens or hydroxyls, or —(CH)$_q$CO$_2$R$_{10}$, wherein R$_{10}$ is a hydrogen atom or a C$_{1-6}$ alkyl, and q is the integer 0, 1, 2, 3, or 4;

R$_4$ is a hydrogen atom, halogen, hydroxyl, C$_{1-6}$ alkyl optionally substituted with 1, 2, or 3 halogens or hydroxyls, or C$_{1-6}$ alkoxy optionally substituted with 1, 2, or 3 halogens, hydroxyls or amino groups;

one of R$_6$ and R$_7$ is —(CH$_2$)$_n$CO$_2$R$_{11}$, —$_{O(CH2)_n}$CO$_2$R$_{11}$, or —(CH$_{2m}$O(CH$_2$)$_p$CO$_2$R$_{11}$, wherein n is the integer 0, 1, 2, 3, 4, 5, or 6, wherein m is the integer 0, 1, 2, 3, or 4, and p is the integer from 0, 1, 2, 3, 4, 5, or 6, and R$_{11}$ is a hydrogen atom or C$_{1-6}$ alkyl optionally substituted with 1, 2, or 3 halogens, or one of R$_6$ and R$_7$ is -L-C(=O)OH, -L-CH=CHC(=O)OH, -L-C(=O)NH$_2$, -L-C (=O)NH(C$_{1-3}$ alkyl), -L-C(=O)N(C$_{1-3}$ alkyl)$_2$, -L-C(=O)NHOH, -L-C(=O)CH$_2$NH$_2$, -LC(=O)CH$_2$OH, L-C(=O)CH$_2$SH, -L-C(=O)NHCN, -L-sulfo, -L-(2,6 difluorophenol), -L-phosphono, and -L-tetrazolyl, wherein L is saturated, partially saturated, or unsaturated, and is selected from the group consisting of —(CH$_2$)$_n$—(CH2)$_n$——(CH$_2$)$_n$C(=O)(CH$_2$)$_n$—, —(CH$_2$)$_n$NH(CH$_2$)$_n$—, —(CH2)$_n$O(CH$_2$)$_n$—, and —(CH$_2$)$_n$S(CH$_2$)$_n$—, wherein each n is an integer independently selected from 0, 1, 2, 3, 4, 5, 6, 7, and 8, wherein each carbon is optionally substituted with one or more C$_{1-3}$ alkyl or C$_{3-6}$ cycloalkyl;

while the other of R$_6$ and R$_7$ is a hydrogen atom, halogen, hydroxyl, C$_{1-6}$ alkyl optionally substituted with 1, 2, or 3 halogens, C$_{1-6}$ alkoxy optionally substituted with 1, 2, or 3 halogens, hydroxyls, or amino groups;

R$_9$ is independently 0, 1, 2, 3, 4, or 5 substituents, which are independently selected from a hydrogen atom, halogen, hydroxyl, C$_{1-6}$ alkyl (optionally substituted with 1, 2, or 3 halogens or hydroxyl groups), C$_{1-6}$ haloalkyl, aryl, heteroaryl, heterocycle, —OR, —C(=O)R, —C(=O)OR, —C(=O)NRR, —NRR, —NRC(=O)R, —NRC(=O)OR, —NRC(=O)NRR, —OC(=O)OR, —OC(=O)OR, —OC(=O)NRR, —SH, —SR, —SOR, —SO$_2$R, —SO$_2$NR$_2$, —NRSO$_2$R, —NR$_2$SO$_2$R, —Si(R)$_3$, or —OP(OR)$_3$, wherein each occurrence of R is the same or different and independently a hydrogen atom, C$_{1-6}$ alkyl, substituted alkyl, aryl, substituted aryl, arylalkyl, substituted arylalkyl, heterocycle, substituted heterocycle, heterocyclealkyl or substituted heterocyclealkyl, or wherein any two R groups attached to the same nitrogen atom, taken together with the nitrogen atom to which they are attached, form a heterocyclic ring or a substituted heterocyclic ring.

3. A compound of claim 1, having a structure according to Formula III:

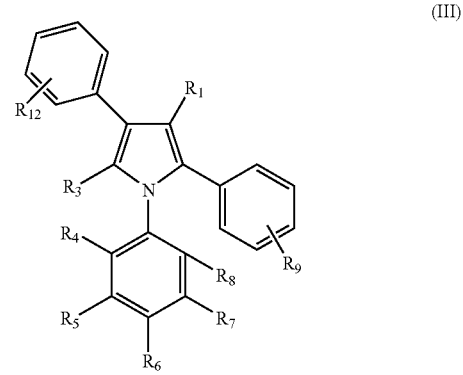

(III)

or a pharmaceutically acceptable salt thereof, wherein:
R$_1$ is a hydrogen atom, halogen, hydroxyl, C$_{1-6}$ alkyl optionally substituted with 1, 2, or 3 halogens or hydroxyls, C$_{1-6}$ alkoxy or —(CH)$_q$CO$_2$R$_{10}$, wherein R$_{10}$ is a hydrogen atom or C$_{1-6}$ alkyl, and q is the integer 0, 1, 2, 3, or 4;

R$_3$ is a hydrogen atom, halogen, hydroxyl, C$_{1-6}$ alkyl optionally substituted with 1, 2, or 3 halogens or hydroxyls, C$_{1-6}$ alkoxy optionally substituted with 1, 2, or 3 halogens, hydroxyls or amino groups, when R$_2$ is an optionally substituted phenyl; or, when R$_2$ is not an optionally substituted phenyl, R$_3$ is —CH$_2$CH$_2$-phenyl, optionally substituted with 1, 2, 3, 4, or 5 of the same or different substituents chosen from halogen, C$_{1-6}$ alkyls optionally substituted with 1, 2, or 3 halogens or hydroxyls, or —(CH)$_q$CO$_2$R$_{10}$, wherein R$_{10}$ is a hydrogen atom or a C$_{1-6}$ alkyl, and q is the integer 0, 1, 2, 3, or 4;

R$_4$ is a hydrogen atom, halogen, hydroxyl, C$_{1-6}$ alkyl optionally substituted with 1, 2, or 3 halogens or hydroxyls, or C$_{1-6}$ alkoxy optionally substituted with 1, 2, or 3 halogens, hydroxyls or amino groups;

R$_5$ is a hydrogen atom, halogen, hydroxyl, C$_{1-6}$ alkyl optionally substituted with 1, 2, or 3 halogens or hydroxyls, or C$_{1-6}$ alkoxy optionally substituted with 1, 2, or 3 halogens, hydroxyls or amino groups;

one of R$_6$ and R$_7$ is —(CH$_2$)$_n$CO$_2$R$_{11}$, —O(CH$_2$)$_n$CO$_2$R$_{11}$, or —(CH$_2$)$_m$O(CH$_2$)$_p$CO$_2$R$_{11}$, wherein n is the integer 0, 1, 2, 3, 4, 5, or 6, wherein m is the integer 0, 1, 2, 3, or 4, and p is the integer from 0, 1, 2, 3, 4, 5, or 6, and R$_{11}$ is a hydrogen atom or C$_{1-6}$ alkyl optionally substituted with 1, 2, or 3 halogens, or one of R$_6$ and R$_7$ is -L-C(=O)OH, -L-CH=CHC(=O)OH, -L-C(=O)NH$_2$, -L-C(=O)NH(C$_{1-3}$ alkyl), -L-C(=O)N(C$_{1-3}$ alkyl)$_2$, -L-C(=O)NHOH, -L-C(=O)CH$_2$NH$_2$, -LC(=O)CH$_2$OH, L-C(=O)CH$_2$SH, -L-C(=O)NHCN, -L-sulfo, -L-(2,6 difluorophenol), -L-phosphono, and -L-tetrazolyl, wherein L is saturated, partially saturated, or unsaturated, and is selected from the group consisting of —(CH$_2$)$_n$—(CH2)$_n$—, —(CH$_2$)$_n$C(=O)(CH$_2$)$_n$—, —(CH$_2$)$_n$NH(CH$_2$)$_n$—, —(CH2)$_n$O(CH$_2$)$_n$—, and —(CH$_2$)$_n$S(CH$_2$)$_n$—, wherein each n is an integer independently selected from 0, 1, 2, 3, 4, 5, 6, 7, and 8, wherein each carbon is optionally substituted with one or more C$_{1-3}$ alkyl or C$_{3-6}$cycloalkyl;

while the other of R$_6$ and R$_7$ is a hydrogen atom, halogen, hydroxyl, C$_{1-6}$ alkyl optionally substituted with 1, 2, or 3 halogens, C$_{1-6}$ alkoxy optionally substituted with 1, 2, or 3 halogens, hydroxyls, or amino groups;

R$_8$ is a hydrogen atom, halogen hydroxyl C$_{1-6}$ alkyl optionally substituted with 1, 2, or 3 halogens or hydroxyls or C$_{1-6}$ alkoxy optionally substitued with 1, 2, or 3 halogens hydroxyls Or amino groups; and R$_9$ and R$_{12}$ are independently 0, 1, 2, 3, 4, or 5 substituents, which are independently selected from a hydrogen atom, halogen, hydroxyl, C$_{1-6}$ alkyl (optionally substituted with 1, 2, or 3 halogens or hydroxyl groups), C$_{1-6}$ haloalkyl, aryl, heteroaryl, heterocycle, —OR, —C(=O)R, —C(=O)OR, —C(=O)NRR, —NRR, —NRC(=O)R, —NRC(=O)OR, —NRC(=O)NRR, —OC(=O)R, —OC(=O)OR, —OC(=O)NRR, —SH, —SR, —SOR, —SO$_2$R, —SO$_2$NR$_2$, —NRSO$_2$R, —NR$_2$SO$_2$R, —Si(R)$_3$, or —OP(OR)$_3$, wherein each occurrence of R is the same or different and independently a hydrogen atom, C$_{1-6}$ alkyl, substituted alkyl, aryl, substituted aryl, arylalkyl, substituted arylalkyl, heterocycle, substituted heterocycle, heterocyclealkyl or substituted heterocyclealkyl, or wherein any two R groups attached to the same nitrogen atom, taken together with the nitrogen atom to which they are attached, form a heterocyclic ring or a substituted heterocyclic ring.

4. A compound of claim 3, wherein R$_1$, R$_5$ and R$_8$ are hydrogen atoms, and the compound has a structure according to Formula IV:

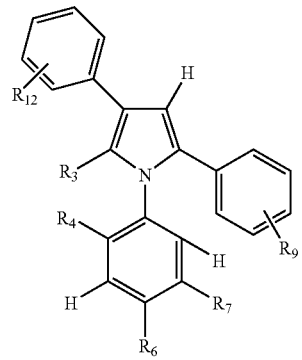

(IV)

or a pharmaceutically acceptable salt thereof, wherein:

R$_3$ is a hydrogen atom, halogen, hydroxyl, C$_{1-6}$ alkyl optionally substituted with 1, 2, or 3 halogens or hydroxyls, C$_{1-6}$ alkoxy optionally substituted with 1, 2, or 3 halogens, hydroxyls or amino groups, when R$_2$ is an optionally substituted phenyl; or, when R$_2$ is not an optionally substituted phenyl, R$_3$ is —CH$_2$CH$_2$—phenyl, optionally substituted with 1, 2, 3, 4, or 5 of the same or different substituents chosen from halogen, C$_{1-6}$ alkyls optionally substituted with 1, 2, or 3 halogens or hydroxyls, or —(CH)$_q$CO$_2$R$_{10}$, wherein R$_{10}$ is a hydrogen atom or a C$_{1-6}$ alkyl, and q is the integer 0, 1, 2, 3, or 4;

R$_4$ is a hydrogen atom, halogen, hydroxyl, C$_{1-6}$ alkyl optionally substituted with 1, 2, or 3 halogens or hydroxyls, or C$_{1-6}$ alkoxy optionally substituted with 1, 2, or 3 halogens, hydroxyls or amino groups;

one of R$_6$ and R$_7$ is —(CH$_2$)$_n$CO$_2$R$_{11}$, —O(CH$_2$)$_n$CO$_2$R$_{11}$, or —(CH$_2$)$_m$O(CH$_2$)$_p$CO$_2$R$_{11}$, wherein n is the integer 0, 1, 2, 3, 4, 5, or 6, wherein m is the integer 0, 1, 2, 3, or 4, and p is the integer from 0, 1, 2, 3, 4, 5, or 6, and R$_{11}$ is a hydrogen atom or C$_{1-6}$ alkyl optionally substituted with 1, 2, or 3 halogens, or one of R$_6$ and R$_7$ is -L-C(=O)OH, -L-CH=CHC(=O)OH, -L-C(=O)NH$_2$, -L-C(=O)NH(C$_{1-3}$ alkyl), -L-C(=O)N(C$_{1-3}$ alkyl)$_2$, -L-C(=O)CH$_2$NH$_2$, -LC(=O)CH$_2$OH, L-C(=O)CH$_2$SH, -L-C(=O)NHCN, -L-sulfo, -L-(2,6 difluorophenol), -L-phosphono, and -L-tetrazolyl, wherein L is saturated, partially saturated, or unsaturated, and is selected from the group consisting of —(CH$_2$)$_n$—(CH2)$_n$—, —(CH$_2$)$_n$C(=O)(CH$_2$)$_n$—, —(CH$_2$)$_n$O(CH$_2$)$_n$—, —(CH2)$_n$O(CH$_2$)$_n$—, and —(CH$_2$)$_n$S(CH$_2$)$_n$—, wherein each n is an integer independently selected from 0, 1, 2, 3, 4, 5, 6, 7, and 8, wherein each carbon is optionally substituted with one or more C$_{1-3}$ alkyl or C$_{3-6}$ cycloalkyl;

while the other of R$_6$ and R$_7$ is a hydrogen atom, halogen, hydroxyl, C$_{1-6}$ alkyl optionally substituted with 1, 2, or 3 halogens, C$_{1-6}$ alkoxy optionally substituted with 1, 2, or 3 halogens, hydroxyls, or amino groups;

R$_9$ and R$_{12}$ are independently 0, 1, 2, 3, 4, or 5 substituents, which are independently selected from a hydrogen atom, halogen, hydroxyl, C$_{1-6}$ alkyl (optionally substituted with 1, 2, or 3 halogens or hydroxyl groups), C$_{1-6}$ haloalkyl, aryl, heteroaryl, heterocycle, —OR, —C(=O)R, —C(=O)OR, —C(=O)NRR, —NRR, —NRC(=O)R, —NRC(=O)OR, —NRC(=O)NRR, —OC(=O)R, —OC(=O)OR, —OC(=O)NRR, —SH, —SR, —SOR, —SO$_2$R, —SO$_2$NR$_2$, —NRSO$_2$R, —NR$_2$SO$_2$R, —Si(R)$_3$, or —OP(OR)$_3$, wherein each occurrence of R is the same or different and independently a hydrogen atom, $C_{1-6}$ alkyl, substituted alkyl, aryl, substituted aryl, arylalkyl, substituted arylalkyl, heterocycle, substituted heterocycle, heterocyclealkyl or substituted heterocyclealkyl, or wherein any two R groups attached to the same nitrogen atom, taken together with the nitrogen atom to which they are attached, form a heterocyclic ring or a substituted heterocyclic ring.

5. A compound of claim 1, having a structure according to Formula V:

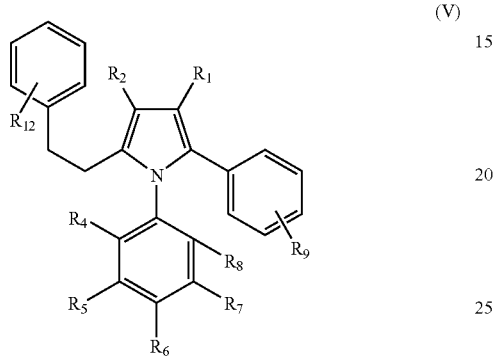

(V)

or a pharmaceutically acceptable salt thereof, wherein:
$R_1$ is a hydrogen atom, halogen, hydroxyl, $C_{1-6}$ alkyl optionally substituted with 1, 2, or 3 halogens or hydroxyls, $C_{1-6}$ alkoxy or —(CH)$_q$CO$_2$R$_{10}$, wherein R$_{10}$ is a hydrogen atom or $C_{1-6}$ alkyl, and q is the integer 0, 1, 2, 3, or 4;

$R_2$ is a hydrogen atom, halogen, hydroxyl, $C_{1-6}$ alkyl optionally substituted with 1, 2, or 3 halogens or hydroxyls, $C_{1-6}$ alkoxy optionally substituted with 1, 2, or 3 halogens, hydroxyls or amino groups, or phenyl, optionally substituted with 1, 2, 3, 4, or 5 of the same or different substituents chosen from halogen, $C_{1-6}$ alkyl optionally substituted with 1, 2, or 3 halogens or hydroxyls, or —(CH)$_q$CO$_2$R$_{10}$ wherein R$_{10}$ is a hydrogen atom or a $C_{1-6}$ alkyl and q is the integer 0, 1, 2, 3, or 4;

$R_4$ is a hydrogen atom, halogen, hydroxyl, $C_{1-6}$ alkyl optionally substituted with 1, 2, or 3 halogens or hydroxyls, or $C_{1-6}$ alkoxy optionally substituted with 1, 2, or 3 halogens, hydroxyls or amino groups;

$R_5$ is a hydrogen atom, halogen, hydroxyl, $C_{1-6}$ alkyl optionally substituted with 1, 2, or 3 halogens or hydroxyls, or $C_{1-6}$ alkoxy optionally substituted with 1, 2, or 3 halogens, hydroxyls or amino groups;

one of $R_6$ and $R_7$ is —(CH$_2$)$_n$CO$_2$R$_{11}$, —O(CH$_2$)$_n$CO$_2$R$_{11}$, or —(CH$_2$)$_m$O(CH$_2$)$_p$CO$_2$R$_{11}$, wherein n is the integer 0, 1, 2, 3, 4, 5, or 6, wherein m is the integer 0, 1, 2, 3, or 4, and p is the integer from 0, 1, 2, 3, 4, 5, or 6, and R$_{11}$ is a hydrogen atom or $C_{1-6}$ alkyl optionally substituted with 1, 2, or 3 halogens, or one of $R_6$ and $R_7$ is -L-C(=O)OH, -L-CH=CHC(=O)OH, -L-C(=O)NH$_2$, -L -C(=O)NH(C$_{1-3}$ alkyl), -L-C(=O)N(C$_{1-3}$ alkyl)$_2$, -L-C(=O)NHOH, -L-C(=O)CH$_2$NH$_2$-LC(=O)CH$_2$OH, L-C(=O)CH$_2$SH, -L-C(=O)NHCN, -L-sulfo, -L-(2,6 difluorophenol), -L-phosphono, and -L-tetrazolyl, wherein L is saturated, partially saturated, or unsaturated, and is selected from the group consisting of —(CH$_2$)$_n$—(CH2)$_n$—, —(CH$_2$)$_n$C(=O)(CH$_2$)$_n$NH(CH$_2$)$_n$—, —(CH2)$_n$—, and —(CH$_2$)$_n$S(CH$_2$)$_n$—, wherein each n is an integer independently selected from 0, 1, 2, 3, 4, 5, 6, 7, and 8, wherein each carbon is optionally substituted with one or more $C_{1-3}$ alkyl or $C_{3-6}$ cycloalkyl;

while the other of $R_6$ and $R_7$ is a hydrogen atom, halogen, hydroxyl, $C_{1-6}$ alkyl optionally substituted with 1, 2, or 3 halogens, $C_{1-6}$ alkoxy optionally substituted with 1, 2, or 3 halogens, hydroxyls, or amino groups;

$R_8$ is a hydrogen atom, halogen, hydroxyl, $C_{1-6}$ alkyl optionally substituted with 1, 2, or 3 halogens or hydroxyls, or $C_{1-6}$ alkoxy optionally substituted with 1, 2, or 3 halogens, hydroxyls or amino groups; and $R_9$ and $R_{12}$ are independently 0, 1, 2, 3, 4, or 5 substituents, which are independently selected from a hydrogen atom, halogen, hydroxyl, $C_{1-6}$ alkyl (optionally substituted with 1, 2, or 3 halogens or hydroxyl groups), $C_{1-6}$ haloalkyl, aryl, heteroaryl, heterocycle, —OR, —C(=O)R, —C(=O)OR, —C(=O)NRR, —NRR, —NRC(=O)R, —NRC(=O)OR, —NRC(=O)NRR, —OC(=O)R, —OC(=O)OR, —OC(=O)NRR, —SH, —SR, —SOR, —SO$_2$R, —SO$_2$NR$_2$, —NRSO$_2$R, —NR$_2$SO$_2$R, —Si(R)$_3$, or —OP(OR)$_3$, wherein each occurrence of R is the same or different and independently a hydrogen atom, $C_{1-6}$ alkyl, substituted alkyl, aryl, substituted aryl, arylalkyl, substituted arylalkyl, heterocycle, substituted heterocycle, heterocyclealkyl or substituted heterocyclealkyl, or wherein any two R groups attached to the same nitrogen atom, taken together with the nitrogen atom to which they are attached, form a heterocyclic ring or a substituted heterocyclic ring.

6. A compound of claim 5, wherein $R_1$, $R_5$ and $R_8$ are hydrogen atoms, and the compound has a structure according to Formula VI:

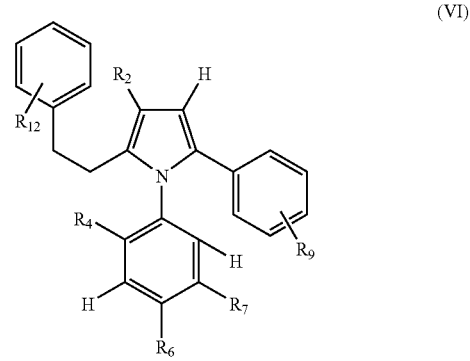

(VI)

or a pharmaceutically acceptable salt thereof, wherein:
$R_2$ is a hydrogen atom, halogen, hydroxyl, $C_{1-6}$ alkyl optionally substituted with 1, 2, or 3 halogens or hydroxyls, $C_{1-6}$ alkoxy optionally substituted with 1, 2, or 3 halogens, hydroxyls or amino groups, or phenyl, optionally substituted with 1, 2, 3, 4, or 5 of the same or different substituents chosen from halogen, $C_{1-6}$ alkyl optionally substituted with 1, 2, or 3 halogens or hydroxyls, or —(CH)$_q$CO$_2$R$_{10}$ wherein R$_{10}$ is a hydrogen atom or a $C_{1-6}$ alkyl and q is the integer 0, 1, 2, 3, or 4;

$R_4$ is a hydrogen atom, halogen, hydroxyl, $C_{1-6}$ alkyl optionally substituted with 1, 2, or 3 halogens or hydroxyls, or $C_{1-6}$ alkoxy optionally substituted with 1, 2, or 3 halogens, hydroxyls or amino groups;

one of $R_6$ and $R_7$ is —$(CH_2)_nCO_2R_{11}$, —$O(CH_2)_nCO_2R_{11}$, or —$(CH_2)_mO(CH_2)_pCO_2R_{11}$, wherein n is the integer 0, 1, 2, 3, 4, 5, or 6, wherein m is the integer 0, 1, 2, 3, or 4, and p is the integer from 0, 1, 2, 3, 4, 5, or 6, and $R_{11}$ is a hydrogen atom or $C_{1-6}$ alkyl optionally substituted with 1, 2, or 3 halogens, or one of $R_6$ and $R_7$ is -L-C(=O)OH, -L-CH=CHC(=O)OH, -L-C(=O)NH_2, -L-C(=O)NH(C_{1-3} alkyl), -L-C(=O)N(C_{1-3} alkyl)_2, -L-C(=O)NHOH, -L-C(=O)CH_2NH_2, -LC(=O)CH_2OH, L-C(=O)CH_2SH, -L-C(=O)NHCN, -L-sulfo, -L-(2,6 difluorophenol), -L-phosphono, and -L-tetrazolyl, wherein L is saturated, partially saturated, or unsaturated, and is selected from the group consisting of -$(CH_2)_n$—$(CH2)_n$—, —$(CH_2)_nC(=O)(CH_2)_n$—, —$(CH_2)_nNH(CH_2)_n$—, —$(CH2)_nO(CH_2)_n$—, and —$(CH_2)_nS(CH_2)_n$—, wherein each n is an integer independently selected from 0, 1, 2, 3, 4, 5, 6, 7, and 8, wherein each carbon is optionally substituted with one or more $C_{1-3}$ alkyl or $C_{3-6}$ cycloalkyl;

while the other of $R_6$ and $R_7$ is a hydrogen atom, halogen, hydroxyl, $C_{1-6}$ alkyl optionally substituted with 1, 2, or 3 halogens, $C_{1-6}$ alkoxy optionally substituted with 1, 2, or 3 halogens, hydroxyls, or amino groups;

$R_9$ and $R_{12}$ are independently 0, 1, 2, 3, 4, or 5 phenyl substituents, which are independently selected from a hydrogen atom, halogen, hydroxyl, $C_{1-6}$ alkyl (optionally substituted with 1, 2, or 3 halogens or hydroxyl groups), $C_{1-6}$ haloalkyl, aryl, heteroaryl, heterocycle, —OR, —C(=O)R, —C(=O)OR, —C(=O)NRR, —NRR, —NRC(=O)R, —NRC(=O)OR, —NRC(=O)NRR, —OC(=O)R, —OC(=O)OR, —OC(=O)NRR, —SH, —SR, —SOR, —SO_2R, —SO_2NR_2, —NRSO_2R, —NR_2SO_2R, —Si(R)_3, or —OP(OR)_3, wherein each occurrence of R is the same or different and independently a hydrogen atom, $C_{1-6}$ alkyl, substituted alkyl, aryl, substituted aryl, arylalkyl, substituted arylalkyl, heterocycle, substituted heterocycle, heterocyclealkyl or substituted heterocyclealkyl, or wherein any two R groups attached to the same nitrogen atom, taken together with the nitrogen atom to which they are attached, form a heterocyclic ring or a substituted heterocyclic ring.

7. A pharmaceutical composition comprising a compound according to claim 1 in combination with a pharmaceutically acceptable carrier or excipient.

8. A method of making a compound of Formula III, comprising providing a compound having a Formula (VII)

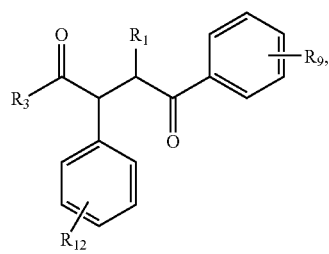

(VII)

and a compound having a Formula (VIII)

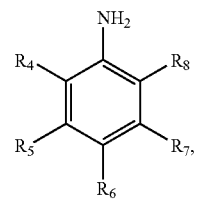

(VIII)

and reacting the two compounds under conditions to form a compound of Formula (III)

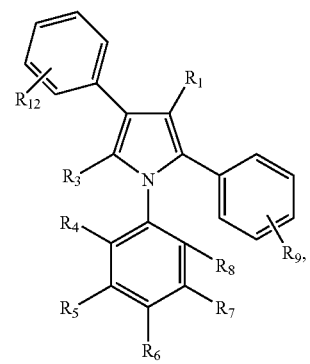

(III)

wherein
$R_1$ is a hydrogen atom, halogen, hydroxyl, $C_{1-6}$ alkyl optionally substituted with 1, 2, or 3 halogens or hydroxyls, $C_{1-6}$ alkoxy or —$(CH)_qCO_2R_{10}$, wherein $R_{10}$ is a hydrogen atom or $C_{1-6}$ alkyl, and q is the integer 0, 1, 2, 3, or 4;

$R_3$ is a hydrogen atom, halogen, hydroxyl, $C_{1-6}$ alkyl optionally substituted with 1, 2, or 3 halogens or hydroxyls, $C_{1-6}$ alkoxy optionally substituted with 1, 2, or 3 halogens, hydroxyls or amino groups, when $R_2$ is an optionally substituted phenyl; or, when $R_2$ is not an optionally substituted phenyl, $R_3$ is —$CH_2CH_2$-phenyl, optionally substituted with 1, 2, 3, 4, or 5 of the same or different substituents chosen from halogen, $C_{1-6}$ alkyls optionally substituted with 1, 2, or 3 halogens or hydroxyls, or —$(CH)_qCO_2R_{10}$, wherein $R_{10}$ is a hydrogen atom or a $C_{1-6}$ alkyl, and q is the integer 0, 1, 2, 3, or 4;

$R_4$ is a hydrogen atom, halogen, hydroxyl, $C_{1-6}$ alkyl optionally substituted with 1, 2, or 3 halogens or hydroxyls, or $C_{1-6}$ alkoxy optionally substituted with 1, 2, or 3 halogens, hydroxyls or amino groups;

$R_5$ is a hydrogen atom, halogen, hydroxyl, $C_{1-6}$ alkyl optionally substituted with 1, 2, or 3 halogens or hydroxyls, or $C_{1-6}$ alkoxy optionally substituted with 1, 2, or 3 halogens, hydroxyls or amino groups;

one of $R_6$ and $R_7$ is —$(CH_2)_nCO_2R_{11}$, —$O(CH_2)_nCO_2R_{11}$, or —$(CH_2)_mO(CH_2)_pCO_2 R_{11}$, wherein n is the integer 0, 1, 2, 3, 4, 5, or 6, wherein m is the integer 0, 1, 2, 3, or 4, and p is the integer from 0, 1, 2, 3, 4, 5, or 6, and $R_{11}$ is a hydrogen atom or $C_{1-6}$ alkyl optionally substituted with 1, 2, or 3 halogens, or one of $R_6$ and $R_7$ is -L-C(=O)OH, -L-CH=CHC(=O)OH, -L-C(=O)NH_2, -L-C(=O)NH(C_{1-3} alkyl), -L-C(=O)N(C_{1-3} alkyl)_2, -L-C(=O)NHOH, -L-C(=O)CH_2NH_2, -LC(=O)

CH$_2$OH, L-C(=O)CH$_2$SH, -L-C(=O)NHCN, -L-sulfo, -L-(2,6 difluorophenol), -L-phosphono, and -L-tetrazolyl, wherein L is saturated, partially saturated, or unsaturated, and is selected from the group consisting of -(CH$_2$)$_n$-(CH2)$_n$—, —(CH$_2$)$_n$C(=O)(CH$_2$)$_n$—, —(CH$_2$)$_n$NH(CH$_2$)$_n$—, —(CH2)$_n$O(CH$_2$)$_n$—, and —(CH$_2$)$_n$S(CH$_2$)$_n$—, wherein each n is an integer independently selected from 0, 1, 2, 3, 4, 5, 6, 7, and 8, wherein each carbon is optionally substituted with one or more C$_{1-3}$ alkyl or C$_{3-6}$ cycloalkyl;

while the other of R$_6$ and R$_7$ is a hydrogen atom, halogen, hydroxyl, C$_{1-6}$ alkyl optionally substituted with 1, 2, or 3 halogens, C$_{1-6}$ alkoxy optionally substituted with 1, 2, or 3 halogens, hydroxyls, or amino groups;

R$_8$ is a hydrogen atom, halogen, hydroxyl, C$_{1-6}$ alkyl optionally substituted with 1, 2, or 3 halogens or hydroxyls, or C$_{1-6}$ alkoxy optionally substituted with 1, 2, or 3 halogens, hydroxyls or amino groups; and R$_9$ and R$_{12}$ are independently 0, 1, 2, 3, 4, or 5 substituents, which are independently selected from a hydrogen atom, halogen, hydroxyl, C$_{1-6}$ alkyl (optionally substituted with 1, 2, or 3 halogens or hydroxyl groups), C$_{1-6}$ haloalkyl, aryl, heteroaryl, heterocycle, —OR, —C(=O)R, —C(=O)OR, —C(=O)NRR, —NRR, —NRC(=O)R, —NRC(=O)OR, —NRC(=O)NRR, —OC(=O)R, —OC(=O)OR, —OC(=O)NRR, —SH, —SR, —SOR, —SO$_2$R, —SO$_2$NR$_2$, —NRSO$_2$R, —NR$_2$SO$_2$R, —Si(R)$_3$, or —OP(OR)$_3$, wherein each occurrence of R is the same or different and independently a hydrogen atom, C$_{1-6}$ alkyl, substituted alkyl, aryl, substituted aryl, arylalkyl, substituted arylalkyl, heterocycle, substituted heterocycle, heterocyclealkyl or substituted heterocyclealkyl, or wherein any two R groups attached to the same nitrogen atom, taken together with the nitrogen atom to which they are attached, form a heterocyclic ring or a substituted heterocyclic ring.

9. A method of making a compound of Formula V, comprising providing a compound having a Formula (IX),

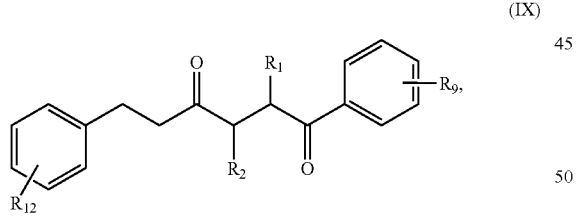

(IX)

and a compound having a Formula (VIII)

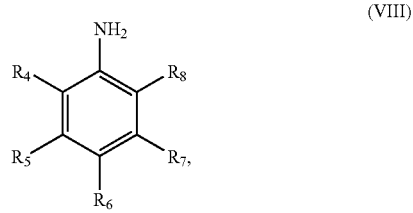

(VIII)

and reacting the two compounds under conditions to form a compound of Formula (V),

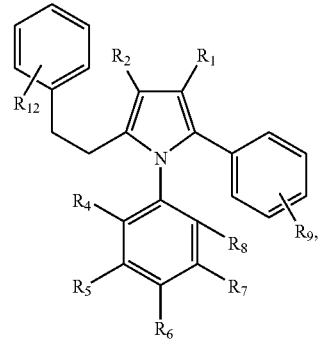

(V)

wherein R$_1$ is a hydrogen atom, halogen, hydroxyl, C$_{1-6}$ alkyl optionally substituted with 1, 2, or 3 halogens or hydroxyls, C$_{1-6}$ alkoxy —(CH)$_q$CO$_2$R$_{10}$, wherein R$_{10}$ is a hydrogen atom or C$_{1-6}$ alkyl, and q is the integer 0, 1, 2, 3, or 4;

R$_2$ is a hydrogen atom, halogen, hydroxyl, C$_{1-6}$ alkyl optionally substituted with 1, 2, or 3 halogens or hydroxyls, C$_{1-6}$ alkoxy optionally substituted with 1, 2, or 3 halogens, hydroxyls or amino groups, or phenyl, optionally substituted with 1, 2, 3, 4, or 5 of the same or different substituents chosen from halogen, C$_{1-6}$ alkyl optionally substituted with 1, 2, or 3 halogens or hydroxyls, or —(CH)$_q$CO$_2$R$_{10}$ wherein R$_{10}$ is a hydrogen atom or a C$_{1-6}$ alkyl and q is the integer 0, 1, 2, 3, or 4;

R$_4$ is a hydrogen atom, halogen, hydroxyl, C$_{1-6}$ alkyl optionally substituted with 1, 2, or 3 halogens or hydroxyls, or C$_{1-6}$ alkoxy optionally substituted with 1, 2, or 3 halogens, hydroxyls or amino groups;

R$_5$ is a hydrogen atom, halogen, hydroxyl, C$_{1-6}$ alkyl optionally substituted with 1, 2, or 3 halogens or hydroxyls, or C$_{1-6}$ alkoxy optionally substituted with 1, 2, or 3 halogens, hydroxyls or amino groups;

one of R$_6$ and R$_7$ is —(CH$_2$)$_n$CO$_2$R$_{11}$, —O(CH$_2$)$_n$CO$_2$R$_{11}$, or —(CH$_2$)$_m$O(CH$_2$)$_p$CO$_2$R$_{11}$, wherein n is the integer 0, 1, 2, 3, 4, 5, or 6, wherein m is the integer 0, 1, 2, 3, or 4, and p is the integer from 0, 1, 2, 3, 4, 5, or 6, and R$_{11}$ is a hydrogen atom or C$_{1-6}$ alkyl optionally substituted with 1, 2, or 3 halogens, or one of R$_6$ and R$_7$ is -L-C(=O)OH, -L-CH=CHC(=O)OH, -L-C(=O)NH$_2$, -L-C(=O)NH(C$_{1-3}$ alkyl), -L-C(=O)N(C$_{1-3}$ alkyl)$_2$, -L-C(=O)NHOH, -L-C(=O)CH$_2$NH$_2$-LC(=O)CH$_2$OH, L-C(=O)CH$_2$SH, -L-C(=O)NHCN, -L-sulfo, -L-(2,6 difluorophenol), -L-phosphono, and -L-tetrazolyl, wherein L is saturated, partially saturated, or unsaturated, and is selected from the group consisting of —(CH$_2$)$_n$—(CH2)$_n$—(CH$_2$)$_n$C(=O)(CH$_2$)$_n$—, —(CH$_2$)$_n$NH(CH$_2$)$_n$—, —(CH2)$_n$O(CH$_2$)$_n$—, and —(CH$_2$)$_n$S(CH$_2$)$_n$—, wherein each n is an integer independently selected from 0, 1, 2, 3, 4, 5, 6, 7, and 8, wherein each carbon is optionally substituted with one or more C$_{1-3}$ alkyl or C$_{3-6}$ cycloalkyl;

while the other of R$_6$ and R$_7$ is a hydrogen atom, halogen, hydroxyl, C$_{1-6}$ alkyl optionally substituted with 1, 2, or 3 halogens, C$_{1-6}$ alkoxy optionally substituted with 1, 2, or 3 halogens, hydroxyls, or amino groups;

R$_8$ is a hydrogen atom, halogen, hydroxyl, C$_{1-6}$ alkyl optionally substituted with 1, 2, or 3 halogens or hydroxyls, or C$_{1-6}$ alkoxy optionally substituted with 1, 2, or 3 halogens, hydroxyls or amino groups; and R$_9$ and R$_{12}$ are independently 0, 1, 2, 3, 4, or 5 substituents, which are independently selected from a hydrogen atom, halogen, hydroxyl, C$_{1-6}$ alkyl (optionally substituted with 1, 2, or 3 halogens or hydroxyl groups), C$_{1-6}$ haloalkyl, aryl, heteroaryl, heterocycle, —OR, —C(=O)R, —C(=O)OR, —C(=O)NRR, —NRR, —NRC(=O)R, —NRC(=O)OR, —NRC(=O)NRR, —OC(=O)R, —OC(=O)OR, —OC(=O)NRR, —SH, —SR, —SOR, —SO$_2$R, —SO$_2$NR$_2$, —NRSO$_2$R, —NR$_2$SO$_2$R, —Si(R)$_3$, or —OP(OR)$_3$, wherein each occurrence of R is the same or different and independently a hydrogen atom, C$_{1-6}$ alkyl, substituted alkyl, aryl, substituted aryl, arylalkyl, substituted arylalkyl, heterocycle, substituted heterocycle, heterocyclealkyl or substituted heterocyclealkyl, or wherein any two R groups attached to the same nitrogen atom, taken together with the nitrogen atom to which they are attached, form a heterocyclic ring or a substituted heterocyclic ring.

10. A compound chosen from:
4-[4-(2-Methyl-3,5-diphenyl-pyrrol-1-yl)-phenyl]-butyric acid;
3-(2-Methyl-3,5-diphenyl-pyrrol-1-yl)-benzoic acid;
2-Chloro-5-(2-methyl-3,5-diphenyl-pyrrol-1-yl)-benzoic acid;
4-Methoxy-3-(2-methyl-3,5-diphenyl-pyrrol-1-yl)-benzoic acid;
3-[3-(2-Methyl-3,5-diphenyl-pyrrol-1-yl)-phenyl]-propionic acid;
3-(2,4-Diphenyl-pyrrol-1-yl)-benzoic acid;
4-[4-(2,4-Diphenyl-pyrrol-1-yl)-phenyl]-butyric acid;
3-[2-Methyl-5-phenyl-3-(3-trifluoromethyl-phenyl)-pyrrol-1-yl]-benzoic acid;
3-{3[2-Methyl-5-phenyl-3-(3-trifluoromethyl-phenyl)-pyrrol-1-yl]-phenyl}-propionic acid;
4-{4[2-Methyl-5-phenyl-3-(3-trifluoromethyl-phenyl)-pyrrol-1-yl]-phenyl}-butyric acid;
3-(2-Ethyl-3,5-diphenyl-pyrrol-1-yl)-benzoic acid;
3-[3-(2-Ethyl-3,5-diphenyl-pyrrol-1-yl)-phenyl]-propionic acid;
4-[4-(2-Ethyl-3,5-diphenyl-pyrrol-1-yl)-phenyl]-butyric acid;
3-[2-Methyl-3-phenyl-5-(4-trifluoromethyl-phenyl)-pyrrol-1-yl]-benzoic acid;
3-{3[2-Methyl-3-phenyl-5-(4-trifluoromethyl-phenyl)-pyrrol-1-yl]-phenyl}-propionic acid;
4-{4[2-Methyl-3-phenyl-5-(4-trifluoromethyl-phenyl)-pyrrol-1-yl]-phenyl}-butyric acid;
3-[5-(3,4-Dichloro-phenyl)-2-methyl-3-phenyl-pyrrol-1-yl]-benzoic acid;
3-{3-[5-(3,4-Dichloro-phenyl)-2-methyl-3-phenyl-pyrrol-1-yl]-phenyl}-propionic acid;
4-{4-[5-(3,4-Dichloro-phenyl)-2-methyl-3-phenyl-pyrrol-1-yl]-phenyl}-butyric acid;
1-(3-Carboxy-phenyl)-5-phenethyl-2-phenyl-1H-pyrrole-3-carboxylic acid ethyl ester;
1[3-(2—Carboxy-ethyl)-phenyl]-5-phenethyl-2-phenyl-1H-pyrrole-3-carboxylic acid ethyl ester;
1-[4-(3-Carboxy-propyl)-phenyl]-5-phenethyl-2-phenyl-1H-pyrrole-3-carboxylic acid ethyl ester;
3-(2-Phenethyl-5-phenyl-pyrrol-1-yl)-benzoic acid;
3-[3-(2-Phenethyl-5-phenyl-pyrrol-1-yl)-phenyl]-propionic acid;
4-[4-(2-Phenethyl-5-phenyl-pyrrol-1-yl)-phenyl]-butyric acid;
[3-(2-Methyl-3,5-diphenyl-pyrrol-1-yl)-phenoxy]-acetic acid;
3-[4-(2-Methyl-3,5-diphenyl-pyrrol-1-yl)-phenoxy]-propionic acid methyl ester;
3-[4-(2-Methyl-3,5-diphenyl-pyrrol-1-yl)-phenoxy]-propionic acid;
4-[4-(2-Cyclohexyl-3,5-diphenyl-pyrrol-1-yl)-phenyl]-butyric acid;
3-(2-Isopropyl-3,5-diphenyl-pyrrol-1-yl)-benzoic acid;
3-[3-(2-Isopropyl-3,5-diphenyl-pyrrol-1-yl)-phenyl]-propionic acid;
4-[4-(2-Isopropyl-3,5-diphenyl-pyrrol-1-yl)-phenyl]-butyric acid;
3-(2-Cyclopropyl-3,5-diphenyl-pyrrol-1-yl)-benzoic acid;
3-[3-(2-Cyclopropyl-3,5-diphenyl-pyrrol-1-yl)-phenyl]-propionic acid;
4-[4-(2-Cyclopropyl-3,5-diphenyl-pyrrol-1-yl)-phenyl]-butyric acid;
3-[2-(2,2-Dimethyl-propyl)-3,5-diphenyl-pyrrol-1-yl]-benzoic acid;
3-{3-[2-(2,2-Dimethyl-propyl)-3,5-diphenyl-pyrrol-1-yl]-phenyl}-propionic acid;
4-{4[2-(2,2-Dimethyl-propyl)-3,5-diphenyl-pyrrol-1-yl]-phenyl}-butyric acid; or 4-(2-Methyl-3,5-diphenyl-pyrrol-1-yl)-benzoic acid.

* * * * *